US011472837B2

(12) United States Patent
Moks et al.

(10) Patent No.: US 11,472,837 B2
(45) Date of Patent: Oct. 18, 2022

(54) PROCESS OF MANUFACTURE OF ANNEXIN V

(71) Applicant: ANNEXIN PHARMACEUTICALS AB, Stockholm (SE)

(72) Inventors: Toomas Moks, Taby (SE); Jan Christoph Reich, Heide (DE)

(73) Assignee: ANNEXIN PHARMACEUTICALS AB, Stockholm (SE)

( * ) Notice: Subject to any disclaimer, the term of this patent is extended or adjusted under 35 U.S.C. 154(b) by 0 days.

(21) Appl. No.: 17/332,968

(22) Filed: May 27, 2021

(65) Prior Publication Data
US 2021/0347819 A1  Nov. 11, 2021

Related U.S. Application Data

(62) Division of application No. 15/760,641, filed as application No. PCT/EP2016/072066 on Sep. 16, 2016.

(30) Foreign Application Priority Data

Sep. 17, 2015 (GB) .................................... 1516516

(51) Int. Cl.
| C07K 1/36 | (2006.01) |
| C07K 1/18 | (2006.01) |
| C07K 1/22 | (2006.01) |
| C07K 1/34 | (2006.01) |
| A61K 38/17 | (2006.01) |

(52) U.S. Cl.
CPC ............ *C07K 1/36* (2013.01); *A61K 38/1709* (2013.01); *C07K 1/18* (2013.01); *C07K 1/22* (2013.01); *C07K 1/34* (2013.01)

(58) Field of Classification Search
CPC ............... C07K 1/36; C07K 1/18; C07K 1/22
See application file for complete search history.

(56) References Cited

U.S. PATENT DOCUMENTS

| 2003/0003048 A1* | 1/2003 | Li ...................... A61K 47/6883 536/123 |
| 2004/0005599 A1* | 1/2004 | Schoenbrunner .... C12N 9/1252 435/6.11 |
| 2005/0054823 A1 | 3/2005 | Saitou |
| 2006/0024308 A1* | 2/2006 | Crea ..................... C07K 16/241 424/145.1 |
| 2006/0029545 A1* | 2/2006 | Kasina ................. A61K 51/088 530/395 |
| 2006/0216777 A1* | 9/2006 | Huang .................... A61P 29/00 435/18 |
| 2011/0060131 A1* | 3/2011 | Barile ................... C12N 9/1241 530/389.8 |
| 2012/0108513 A1 | 5/2012 | Miterer |
| 2012/0219538 A1* | 8/2012 | Borchard ............. A61K 9/0019 560/33 |
| 2013/0224235 A1* | 8/2013 | Jarvekulg .............. A61K 39/12 424/186.1 |
| 2014/0134193 A1* | 5/2014 | Subramanyam ..... A61K 31/351 424/181.1 |

FOREIGN PATENT DOCUMENTS

| EP | 0 430 121 A1 | 6/1991 |
| EP | 0 441 274 A2 | 8/1991 |
| EP | 0 452 849 A1 | 10/1991 |
| EP | 0 457 371 A1 | 11/1991 |
| EP | 1 599 578 B1 | 7/2011 |
| EP | 2 687 539 B1 | 5/2017 |
| JP | 2008-502592 | 1/2008 |
| JP | 2012-505837 | 3/2012 |
| JP | 2012-521977 | 9/2012 |
| JP | 2015-519339 | 7/2015 |
| WO | WO 86/04094 | 7/1986 |
| WO | WO 2002/050112 | 6/2002 |
| WO | WO 2002/067857 | 9/2002 |
| WO | WO 2005/086955 | 9/2005 |
| WO | WO 2005/099744 | 10/2005 |
| WO | WO 2009/077764 | 6/2009 |
| WO | WO 2009/103977 | 8/2009 |
| WO | WO 2010/043045 | 4/2010 |

(Continued)

OTHER PUBLICATIONS

"Hydrophobic Interaction Chromatography, Principles and Methods", Amersham Pharmacia Biotech, 1993, ISBN 91-970490-4-2.
Abdullah, N., and H. A. Chase. "Removal of poly-histidine fusion tags from recombinant proteins purified by expanded bed adsorption." *Biotechnology and bioengineering* 92.4 (2005): 501-513.
Aon, Juan C., et al. "Suppressing posttranslational gluconoylation of heterologous proteins by metabolic engineering of *Escherichia coli*." *Appl. Environ. Microbiol.* 74.4 (2008): 950-958.
Beveridge, Terry J. "Structures of gram-negative cell walls and their derived membrane vesicles." *Journal of bacteriology* 181.16 (1999): 4725-4733.

(Continued)

*Primary Examiner* — Daniel E Kolker
*Assistant Examiner* — James L Rogers
(74) *Attorney, Agent, or Firm* — ParkerHighlander PLLC

(57) ABSTRACT

The present invention provides a process for the recovery and/or purification of a recombinantly expressed intracellular protein comprising the sequence of Annexin A5 (AnxA5) from an endotoxin-producing host cell with a cell wall, wherein the process comprises releasing the intracellular protein from the host cell, characterised in that the step of releasing the intracellular AnxA5 protein is conducted in the presence of a homogenisation buffer comprising non-ionic detergent, and preferably wherein the process does not include any centrifugation steps for the recovery and/or purification of the AnxA5 protein after its release from the host cell and/or in which the AnxA5 protein remains in solution throughout the process except when temporarily bound to any chromatographic resins.

22 Claims, 9 Drawing Sheets
Specification includes a Sequence Listing.

(56) References Cited

FOREIGN PATENT DOCUMENTS

| | | |
|---|---|---|
| WO | WO 2010/069605 | 6/2010 |
| WO | WO 2010/109212 | 9/2010 |
| WO | WO 2010/140886 | 12/2010 |
| WO | WO 2011/135071 | 11/2011 |
| WO | WO 2012/136819 | 10/2012 |
| WO | WO 2013/053888 | 4/2013 |
| WO | WO 2013/170272 | 11/2013 |

OTHER PUBLICATIONS

Burger, A., et al. "A rapid and efficient purification method for recombinant annexin V for biophysical studies." *FEBS letters*329. 1-2 (1993): 25-28.

Capila, Ishan, et al. "Annexin V-heparin oligosaccharide complex suggests heparan sulfate-mediated assembly on cell surfaces." *Structure* 9.1 (2001): 57-64.

Capila, Ishan, et al. "Interaction of heparin with annexin V." *FEBS letters* 446.2-3 (1999): 327-330.

Cederholm, Anna, and Johan Frostegård. "Annexin A5 multitasking: a potentially novel antiatherothrombotic agent?." *Drug news & perspectives* 20.5 (2007): 321-326.

Cohen, Stanley N., Annie CY Chang, and Leslie Hsu. "Nonchromosomal antibiotic resistance in bacteria: genetic transformation of *Escherichia coli* by R-factor DNA." *Proceedings of the National Academy of Sciences* 69.8 (1972): 2110-2114.

Frej et al., "Pilot scale recovery and recombinant annexin V from unclarified *Escherichia coli* homegenate using expanded bed adsorption." *Biotech.& Bioengineering* 44(1994): 922-929.

Gerke, Volker, Carl E. Creutz, and Stephen E. Moss. "Annexins: linking Ca 2+ signalling to membrane dynamics." *Nature reviews Molecular cell biology* 6.6 (2005): 449.

Hawthorne, T. R., et al. "Isolation and characterization of recombinant annexin V expressed in *Saccharomyces cerevisiae*." *Journal of biotechnology* 36.2 (1994): 129-143.

Huber, Robert, et al. "Crystal and molecular structure of human annexin V after refinement: implications for structure, membrane binding and ion channel formation of the annexin family of proteins." *Journal of molecular biology* 223.3 (1992): 683-704.

Ichimura, Takaharu, et al. "Kidney injury molecule-1 (KIM-1), a putative epithelial cell adhesion molecule containing a novel immunoglobulin domain, is up-regulated in renal cells after injury." *Journal of Biological Chemistry* 273.7 (1998): 4135-4142.

International Preliminary Report on Patentability issued in International Application No. PCT/EP2016/072066, dated Sep. 6, 2017.

Jin, Xianbo, et al. "Electrochemical preparation of silicon and its alloys from solid oxides in molten calcium chloride." *Angewandte Chemie International Edition* 43.6 (2004): 733-736.

Kobayashi, Norimoto, et al. "TIM-1 and TIM-4 glycoproteins bind phosphatidylserine and mediate uptake of apoptotic cells." *Immunity* 27.6 (2007): 927-940.

Kumar, "Expression, Purification and Large-Scale Production of the Human Recombinant Annexin-V Protein," Undergraduate thesis, University of Arkansas, 1991.

Lennox, E. S. "Transduction of linked genetic characters of the host by bacteriophage P1." *Virology* 1.2 (1955): 190-206.

Lewit-Bentley, Anita, et al. "The effect of metal binding on the structure of annexin V and implications for membrane binding." *European journal of biochemistry* 210.1 (1992): 73-77.

Li, Xin, et al. "Annexin A5 protein expression is associated with the histological differentiation of uterine cervical squamous cell carcinoma in patients with an increased serum concentration." *Molecular Medicine Reports* 6.6 (2012): 1249-1254.

Liemann, S., and R. Huber. "Three-dimensional structure of annexins." *Cellular and Molecular Life Sciences CMLS* 53.6 (1997): 516-521.

Liu, I. R. I. S., M. A. R. T. H. A. Liu, and K. A. R. E. N. Shergill. "The effect of spheroplast formation on the transformation efficiency in *Escherichia coli* DH5α." *J. Exp. Microbiol. Immunol* 9 (2006): 81-85.

Logue, Susan E., Mohamed Elgendy, and Seamus J. Martin. "Expression, purification and use of recombinant annexin V for the detection of apoptotic cells." *Nature protocols* 4.9 (2009): 1383.

Marder, Laura S., et al. "Production of recombinant human annexin V by fed-batch cultivation." *BMC biotechnology* 14.1 (2014): 33.

Mizokami, Hiroshi, et al. "A convenient method for preparation of the calcium ion-binding protein annexin V." *Journal of bioscience and bioengineering* 97.2 (2004): 95-98.

Moller-Tank, Sven, et al. "Role of the phosphatidylserine receptor TIM-1 in enveloped-virus entry." *Journal of virology*87.15 (2013): 8327-8341.

Noll, Stephan, et al. "Gezielte Optimierung von *Escherichia coli* BL21 (DE3)." *BIOspektrum* 19.2 (2013): 211-213.

Park, Jung Hwa, et al. "Annexin A5 increases survival in murine sepsis model by inhibiting HMGB1-mediated proinflammation and coagulation." *Molecular Medicine* 22.1 (2016): 424-436.

Production of Recombinant Annexin V from plasmid pET12a-PAPI, 2008, available online at https://depts.washington.edu/labweb/Faculty/Tait/108.pdf.

Rand, Jacob H., et al. "Annexin A5 binds to lipopolysaccharide and reduces its endotoxin activity." *MBio* 3.2 (2012): e00292-11.

Saijo, Masayuki, et al. "Laboratory diagnostic systems for Ebola and Marburg hemorrhagic fevers developed with recombinant proteins." *Clin. Vaccine Immunol.* 13.4 (2006): 444-451.

Santiago, César, et al. "Structures of T Cell immunoglobulin mucin receptors 1 and 2 reveal mechanisms for regulation of immune responses by the TIM receptor family." *Immunity* 26.3 (2007): 299-310.

Shurtleff, Amy, et al. "Standardization of the filovirus plaque assay for use in preclinical studies." *Viruses* 4.12 (2012): 3511-3530.

Smither, Sophie J., et al. "Comparison of the plaque assay and 50% tissue culture infectious dose assay as methods for measuring filovirus infectivity." *Journal of virological methods*193.2 (2013): 565-571.

Sonar, Sanchaita Sriwal, et al. "Antagonism of TIM-1 blocks the development of disease in a humanized mouse model of allergic asthma." *The Journal of clinical investigation* 120.8 (2010): 2767-2781.

Thiagarajan, Perumal, and Claude R. Benedict. "Inhibition of arterial thrombosis by recombinant annexin V in a rabbit carotid artery injury model." *Circulation* 96.7 (1997): 2339-2347.

Trotter, Patrick J., Margaret A. Orchard, and John H. Walker. "Ca2+ concentration during binding determines the manner in which annexin V binds to membranes." *Biochemical Journals*308.2 (1995): 591-598.

Vermes, István, et al. "A novel assay for apoptosis flow cytometric detection of phosphatidylserine expression on early apoptotic cells using fluorescein labelled annexin V." *Journal of immunological methods* 184.1 (1995): 39-51.

Wang, Fang, et al. "Non-fusion expression in *Escherichia coli*: Single-step purification of recombinant human annexin A5 for detection of apoptosis." *Protein expression and purification*45.1 (2006): 80-87.

Zaki, Sherif R. et al. "A novel immunohistochemical assay for the detection of Ebola virus in skin: implications for diagnosis, spread, and surveillance of Ebola hemorrhagic fever." *The Journal of infectious diseases* 179.Supplement_1 (1999): S36-S47.

Zhang, L. N., X. Yang, and Z. C. Hua. "Expression and purification of recombinant human annexin V in *Escherichia coli*." (2000): 305-312.

Zhang, Youming, et al. "A new logic for DNA engineering using recombination in *Escherichia coli*." *Nature genetics* 20.2 (1998): 123.

Aida & Pabst, "Removal of endotoxin from protein solutions by phase separation using Triton X-114," Journal of Immunological Methods, 1322:191-195, 1990.

Kheifets et al., "Protein Kinase C δ (δPKC)-Annexin V Interaction: a Required Step in δPKC Translocation and Function" *The Journal of Biological Chemistry*, vol. 281, No. 32:23218-23226, 2006.

Kumar et al., "Optimization and efficient purification of recombinant Omp28 protein of *Brucella melitensis* using Triton X-100 and b-mercaptoethanol", *Protein Expression and Purification* 83:226-232, 2012.

\* cited by examiner

Fig. 1

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
                35                  40                  45

Gln Arg Gln Glu Ile Ser Ala Ala Phe Lys Thr Leu Phe Gly Arg Asp
                50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
                100                 105                 110

Ile Ile Ala Ser Arg Thr Pro Glu Glu Leu Arg Ala Ile Lys Gln Val
                115                 120                 125

Tyr Glu Glu Glu Tyr Gly Ser Ser Leu Glu Asp Asp Val Val Gly Asp
                130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
                180                 185                 190

Lys Phe Ile Thr Ile Phe Gly Thr Arg Ser Val Ser His Leu Arg Lys
                195                 200                 205
```

Fig. 1 con't

```
Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
            245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
        290                 295                 300

Ser Gly Asp Tyr Lys Lys Ala Leu Leu Leu Leu Cys Gly Glu Asp Asp
305                 310                 315                 320
```

Fig. 3

| Process Step | Parameter | 3 L process | 100 L process |
|---|---|---|---|
| AX | Resin:<br>Column:<br>Column diameter (cm):<br>Bed height (cm):<br>Column volume (L):<br>Flow rate:<br>Buffer temperature:<br>Pump: | Q Sepharose XL<br>XK 50<br>5<br>13.5<br>0.265<br>200 cm/h<br>Ambient temperature<br>with WATSON-MARLOW Tubing pump 323S | Q Sepharose XL<br>BPG 300<br>30<br>13.5<br>9.5<br>170 cm/h<br>Ambient temperature<br>BioProcess system |
| EQ | Buffer A:<br>Vol: | 20 mM Tris pH 7.4, 0.1 % Tween80, 25 mM NaCl<br>2 CV | 20 mM Tris pH 7.4, 0.1 % Tween80, 25 mM NaCl<br>3 CV |
| Load | | | Online dilution (1+1) with 1% (v/v) Tween 80, 4 mM EDTA, pH 8.0 |
| Wash | Buffer:<br>Vol: | 20 mM Tris pH 7.4, 0.1 % Tween80, 25 mM NaCl<br>10 CV | 20 mM Tris pH 7.4, 0.1 % Tween80, 25 mM NaCl<br>10 CV |
| Step Elution | 100 % Buffer B:<br>Vol: | 20 mM Tris pH 7.4, 0.1 % Tween80, 300 mM NaCl<br>9 CV | 20 mM Tris pH 7.4, 0.1 % Tween80, 300 mM NaCl<br>9 CV |
| Pooling | Criteria: | Main peak<br>Pool (0.1 AU-0.2 AU) | Main peak<br>Pool (target 0.2 AU-0.4 AU ; 5 mm light path)<br>(within 3 weeks) |
| CIP | Step 1:<br>Vol:<br>Step 2:<br>Vol:<br>Incubation: | 2 M NaCl<br>3 CV<br>1 M NaOH<br>3 CV<br>15 h | 2 M NaCl<br>3 CV<br>1 M NaOH<br>3 CV<br>15 h |
| Storage | Storage: | 20 mM NaOH | 10 mM NaOH |

Fig. 4

| Process Step | Parameter | 3 L Process | 100 L Process |
|---|---|---|---|
| AF | Resin: | Heparin HyperD | Heparin HyperD |
|  | Column: | XK 50 | BPG300 |
|  | Column diameter (cm): | 5 | 30 |
|  | Bed height (cm): | 25 | 25 |
|  | Column volume (L): | 0.491 | 17.7 |
|  | Flow rate: | 60-100 cm/h | 60-100 cm/h |
|  | Buffer temperature: | Ambient temperature | Ambient temperature |
| EQ | Buffer A: | 20 mM Tris pH 7.4; 0.1 % Tween80; 2 mM $CaCl_2$, 25 mM NaCl | 20 mM Tris pH 7.4; 0.1 % Tween80; 2 mM $CaCl_2$, 25 mM NaCl |
|  | Vol: | 2 CV | 3 CV |
| Load | Flow rate: | 100 cm/h | 60-100 cm/h; online 1:8 dilution of AX eluate with buffer A |
| Wash 1 | Buffer: | 20 mM Tris pH 7.4; 0.1 % Tween80; 2 mM $CaCl_2$, 25 mM NaCl | 20 mM Tris pH 7.4; 0.1 % Tween80; 2 mM $CaCl_2$, 25 mM NaCl |
|  | Vol: | 15 CV | 15 CV |
|  | Flow rate: | 100 cm/h | 60-100 cm/h |
| Wash 2 | Buffer: | 20 mM Tris pH 7.4; 0.1 % Tween80, 25 mM NaCl | 20 mM Tris pH 7.4; 0.1 % Tween80, 25 mM NaCl |
|  | Vol: | 2 CV | 2 CV |
|  | Flow rate: | 100 cm/h | 60-100 cm/h |
| Step Elution | 100 % Buffer B: | 20 mM Tris pH 7.4; 0.1 % Tween80; 10 mM EDTA; 25 mM NaCl | 20 mM Tris pH 7.4; 0.1 % Tween80; 10 mM EDTA; 25 mM NaCl |
|  | Vol: | 2-3 CV | 2-3 CV |
|  | Flow rate: | 40-60 cm/h | 40-60 cm/h |
| Pooling | Criteria: | Complete peak Pool (0.1 AU-0.1 AU) | Complete peak Pool (0.2 AU-0.2 AU ; 5 mm light path) |
| CIP | Step 1: | 2 M NaCl | (within 3 weeks) 2 M NaCl |
|  | Vol: | 3 CV | 3 CV |
|  | Step 2: | 0.1 M NaOH | 0.1 M NaOH |
|  | Vol: | 3 CV | 3 CV |
|  | Incubation: | 15 h | ≥15 h (contact time, no pumping) |
| Storage | Storage: | 1 M NaCl, 25% EtOH | 1 M NaCl, 25% EtOH |

Fig. 5

| Process Step | Parameter | 3 L process | 100 L process |
|---|---|---|---|
| AX | Resin: | Source15 Q | Source15 Q |
| | Column: | - | Fineline200 |
| | Column diameter (cm): | - | 20 |
| | Bed height (cm): | 15 | 15 |
| | Column volume (L): | 0.4 | 4.7 |
| | Flow rate: | 100 cm/h | 100 cm/h |
| | Buffer temperature: | Ambient temperature | Ambient temperature |
| EQ | Buffer A:<br>Vol: | 20 mM Bis-Tris pH 7; 25 mM NaCl<br>2 CV | 20 mM Bis-Tris pH 7; 25 mM NaCl<br>3 CV |
| Load | Flow rate: | 100 cm/h | 100 cm/h<br>AF pool splitting (1/4-1/5) |
| Wash | Buffer:<br>Vol:<br>Flow rate: | 20 mM Bis-Tris pH 7; 25 mM NaCl<br>3 CV<br>100 cm/h | 20 mM Bis-Tris pH 7; 25 mM NaCl<br>3 CV<br>100 cm/h |
| Gradient Elution | Buffer B:<br>Gradient: | 20 mM Bis-Tris pH 7; 180 mM NaCl 0-100% B in 33 CV | 20 mM Bis-Tris pH 7; 180 mM NaCl 0-100% B in 33 CV |
| Pooling | Criteria: | major peak starting at 0.05 AU to the valley between peak 1 and peak 2 | major peak starting at 0.1 AU to the valley between peak 1 and peak 2 (5 mm light path) |
| CIP | Step 1:<br>Vol: | 2 M NaCl<br>3 CV | (within 3 weeks)<br>2 M NaCl<br>3 CV |
| | Step 2:<br>Vol:<br>Incubation: | 1 M NaOH<br>3 CV<br>15 h | 1 M NaOH<br>3 CV<br>≥15 h (contact time, no pumping) |
| Storage | Storage: | 25 mM NaOH | 10 mM NaOH |

Fig. 6

| Process Step | Parameter | 3 L process | 100 L process |
|---|---|---|---|
| Concentration | cassette: | Hydrosart 10 K | Hydrosart 10 K |
| | area: | 0.1 m² | 2.4 m² |
| | Target concentration: | 5 g/L | 5 g/L |
| | Processing time: | ~ 2h | - |
| | Parameter: | TMP 0.9-1.1 | TMP 0.9-1.1 |
| | | Entrance pressure 1 bar | Entrance pressure 1 bar |
| | | Retentate back pressure 0.8 bar | Retentate back pressure 0.8 bar |
| | Concentration factor | ~ 6 | 6-8 |
| Buffer change | Dilution buffer: | 20 mM Bis-Tris, 150 mM NaCl, 1mM CaCl$_2$ pH 7 | 20 mM Bis-Tris, 150 mM NaCl, 1mM CaCl$_2$ pH 7 |
| | Diafiltration volumes: | 10 | 10 |
| | Concentration factor | ~ 6 | ~ 6 |
| | Target concentration: | 12 g/L | 12 g/L |
| | Dilution | Addition of cassette wash | Addition of cassette wash |
| Addition of Tween80 | Buffer: | 20 mM Bis-Tris, 150 mM NaCl, 1mM CaCl2, 10 % Tween80 pH 7 | 20 mM Bis-Tris, 150 mM NaCl, 1mM CaCl2, 10 % Tween80 pH 7 |
| | Target concentration Tween80: | 0.05 % | 0.05 % |
| | Target concentration bulk: | 10 g/L | 10 g/L |
| Sterile filtration | Device: | Sartopore2 | Sartopore2 |
| | Cut off: | 0.45-0.2 μm | 0.45-0.2 μm |
| | Target concentration bulk: | 10 g/L | 10 g/L |
| Storage of bulk | Temperature: | 2-8°C | 2-8°C |

SEQUENCE LISTING

<160> NUMBER OF SEQ ID NOS: 2

<210> SEQ ID NO 1
<211> LENGTH: 320
<212> TYPE: PRT
<213> ORGANISM: Homo sapiens

<400> SEQUENCE: 1

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95
```

```
Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Tyr Gly Ser Ser Leu Glu Asp Val Val Gly Asp
130                 135                 140

Thr Ser Gly Tyr Tyr Gln Arg Met Leu Val Val Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320

<210> SEQ ID NO 2
<211> LENGTH: 362
<212> TYPE: PRT
<213> ORGANISM: Homo sapiens

<400> SEQUENCE: 2

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Arg
        35                  40                  45

Gly Ser Cys Ser Leu Phe Thr Cys Gln Asn Gly Ile Val Trp Thr Asn
    50                  55                  60

Gly Thr His Val Thr Tyr Arg Lys Asp Thr Arg Tyr Lys Leu Leu Gly
65                  70                  75                  80

Asp Leu Ser Arg Arg Asp Val Ser Leu Thr Ile Glu Asn Thr Ala Val
                85                  90                  95

Ser Asp Ser Gly Val Tyr Cys Cys Arg Val Glu His Arg Gly Trp Phe
            100                 105                 110

Asn Asp Met Lys Ile Thr Val Ser Leu Glu Ile Val Pro Pro Lys Val
        115                 120                 125

Thr Thr Thr Pro Ile Val Thr Thr Val Pro Thr Val Thr Thr Val Arg
    130                 135                 140

Thr Ser Thr Thr Val Pro Thr Thr Thr Thr Val Pro Met Thr Thr Val
```

```
145                 150                 155                 160
Pro Thr Thr Thr Val Pro Thr Thr Met Ser Ile Pro Thr Thr Thr Thr
                165                 170                 175

Val Leu Thr Thr Met Thr Val Ser Thr Thr Thr Ser Val Pro Thr Thr
                180                 185                 190

Thr Ser Ile Pro Thr Thr Thr Ser Val Pro Val Thr Thr Thr Val Ser
            195                 200                 205

Thr Phe Val Pro Pro Met Pro Leu Pro Arg Gln Asn His Glu Pro Val
        210                 215                 220

Ala Thr Ser Pro Ser Ser Pro Gln Pro Ala Glu Thr His Pro Thr Thr
225                 230                 235                 240

Leu Gln Gly Ala Ile Arg Arg Glu Pro Thr Ser Ser Pro Leu Tyr Ser
                245                 250                 255

Tyr Thr Thr Asp Gly Asn Asp Thr Val Thr Glu Ser Ser Asp Gly Leu
                260                 265                 270

Trp Asn Asn Gln Thr Gln Leu Phe Leu Glu His Ser Leu Leu Thr Ala
                275                 280                 285

Asn Thr Thr Lys Gly Ile Tyr Ala Gly Val Cys Ile Ser Val Leu Val
            290                 295                 300

Leu Leu Ala Leu Leu Gly Val Ile Ile Ala Lys Lys Tyr Phe Phe Lys
305                 310                 315                 320

Lys Glu Val Gln Gln Leu Ser Val Ser Phe Ser Ser Leu Gln Ile Lys
                325                 330                 335

Ala Leu Gln Asn Ala Val Glu Lys Glu Val Gln Ala Glu Asp Asn Ile
            340                 345                 350

Tyr Ile Glu Asn Ser Leu Tyr Ala Thr Asp
            355                 360
```

PROCESS OF MANUFACTURE OF ANNEXIN V

This application is a divisional of U.S. patent application Ser. No. 15/760,641, filed Mar. 16, 2018, as a national phase application under 35 U.S.C. § 371 of International Application No. PCT/EP2016/072066, filed Sep. 16, 2016, which claims priority to United Kingdom Patent Application No. 1516516.0, filed Sep. 17, 2015. The entire text of each of the above referenced disclosures is specifically incorporated herein by reference.

FIELD OF THE INVENTION

The present application relates to processes for the manufacture of protein comprising the sequence of Annexin A5 (AnxA5). More particularly, the process is for the recovery and/or purification of the AnxA5 protein, especially from a recombinant host cell, such as bacterial host cell. The processes described herein are highly efficient and cost effective, and can be used on a commercial scale (e.g. with recombinant host cell cultures having a culture volume of about 1000 L or more) to rapidly and conveniently produce pharmaceutical grade AnxA5 protein product.

BACKGROUND OF THE INVENTION

The listing or discussion of an apparently prior-published document in this specification should not necessarily be taken as an acknowledgement that the document is part of the state of the art or is common general knowledge.

Atherothrombosis, formed on an underlying atherosclerotic plaque, is the key pathogenic mechanism behind the majority of clinically evident cardiovascular ischemic diseases including acute coronary artery disease, cerebrovascular and peripheral arterial occlusion. As discussed in Cederholm and Frostegård, 2007, *Drug News Perspect.*, 20(5): 321-6, Annexin A5 (previously known as annexin V), a member of the annexin superfamily, is a protein with potent and unique antithrombotic properties. The antithrombotic effect exerted by Annexin A5 is thought to be mediated mainly by mechanical shielding of phospholipids, phosphatidylserine in particular, thereby reducing their availability for coagulation reactions. However, other intriguing properties of Annexin A5 potentially contributing to its antithrombotic function, especially downregulation of surface expressed tissue factor, or interaction with additional ligands involved in hemostasis such as sulfatide and heparin, as well as upregulation of urokinase-type plasminogen activator were reported. The biological significance of Annexin A5 as a member of endogenous antithrombotic system in vivo has also been suggested for the large vasculature and for placental microcirculation.

Indeed, it is known that Annexin A5 has a wide range of utilities in medicine, in providing direct therapeutic effects. Examples include the use of Annexin A5:

for prevention of atherothrombosis and/or plaque rupture as described in WO 2005/099744 (the contents of which are incorporated herein by reference);

for the treatment of vascular dysfunction, reducing ischemic pain and/or treatment of a vascular disease rupture as described in WO 2009/077764 (the contents of which are incorporated herein by reference);

for the prophylaxis or treatment of restenosis as described in WO 2009/103977 (the contents of which are incorporated herein by reference);

for use in inhibiting the activity of oxidised cardiolipin (oxCL) and for treating, preventing and/or reducing the risk of developing a cardiovascular disease, an auto-immune disease or inflammatory condition as described in WO 2010/069605 (the contents of which are incorporated herein by reference); and for the prevention and/or reduction of peri- or postoperative complications following surgical intervention, such as complications following vascular surgery, especially peripheral vascular surgery as described in WO 2012/136819 (the contents of which are incorporated herein by reference).

As such, Annexin A5 represents a protein of high therapeutic interest and potential. Therefore, there is a pressing need for an effective method to produce therapeutic grade Annexin A5 protein by an efficient and cost-effective process that can be scaled up and conveniently applied to commercial scale production (e.g. to collect Annexin A5 protein from recombinant host cell cultures having a culture volume of about 1000 L or more).

A particular challenge, when recombinantly expressing Annexin A5 in standard bacterial host cells such as *E. coli*, is contamination with host cell derived components, and in particular with endotoxin. Endotoxin is a lipopolysaccharide (LPS), which is formed of a lipid and a polysaccharide composed of 0-antigen, outer core and inner core joined by a covalent bond; LPS is found in the outer membrane of Gram-negative bacteria, and elicit strong immune responses in animals. Annexin A5 is characterised by its strong binding to biological membranes containing negatively charged phospholipids, and so has a particularly high affinity to endotoxin. This makes large, commercial scale, production of Annexin A5 from endotoxin-producing hosts even more challenging.

To date, no such process has been provided to produce therapeutic grade Annexin A5 protein by an efficient and cost-effective process that can be scaled up and conveniently applied to commercial scale production (e.g. to collect Annexin A5 protein from recombinant host cell cultures having a culture volume of about 1000 L or more) at all, much less in a way that addresses endotoxin contamination.

In 1991, Kumar reported on the development of a process for the production and purification of Annexin A5 (An Undergraduate Honors College Thesis entitled "*Expression, Purification, and Large-Scale Production of the Human Recombinant Annexin-V Protein*" as presented to Department of Chemical Engineering College of Engineering University of Arkansas, Fayetteville, Ark., available online at https://uarkive.uark.edu/xmlui/handle/10826/981). Kumar's process involved the expression of the Annexin A5 in recombinant *E. coli* host cells in 100 mL culture flasks, pelleting the cells, resuspending the cells in presence of a homogenisation/lysis buffer consisting of 50 mM Tris HCl, 10 mM $CaCl_2$) at pH 7.2, and then breaking the cells via sonication to release the Annexin A5 protein. The added $CaCl_2$) caused the Annexin A5 to bind, in a calcium-dependent manner, to the cell membranes in the debris, and then the mixture was subjected to a first purification centrifugation step of 20 minutes, after which the supernatant was discarded and the pellet containing the cell debris and the bound Annexin A5 was recovered. Annexin A5 was released from the pellet using EDTA, and this was followed by a second purification centrifugation step of 20 minutes and collection of the Annexin A5 in the supernatant. Then followed an overnight dialysis to change the buffer for Annexin A5 to Tris HCl at pH 8.0, before the further step of anion exchange on a DEAE-sepharose column, and elution of Annexin A5 using a salt gradient.

The present applicant has realised that there are numerous limitations and shortcomings in the method of Kumar. First, it is only demonstrated on a small scale, using 100 mL cultures, and requires two separate centrifugation steps during the purification process. This is not scalable to commercial processes that use high volume cultures (e.g. 1000 L or greater) in an efficient way. As discussed further below, the centrifugation of such high volumes of fluid would be extremely time-consuming and costly. Yet, centrifugation is necessitated by Kumar's approach which relies on using calcium-induced binding of Annexin A5 to the membranes in cell debris as a preliminary capture step. Second, the applicant has realised that the method of Kumar leads to high losses of Annexin A5 protein, for example, by disposing of soluble Annexin A5 that is unbound in the supernatant of the product of the first purification centrifugation step. Third, the method of Kumar is completely unable to remove endotoxin to a level suitable for a therapeutic use, and it is notable that there are no checks on endotoxin levels in the final product. As such, Kumar's method is not scalable to commercial production in an efficient and time-effective manner, leads to high losses of Annexin A5 protein (i.e. low yields) and results in a low grade of protein purification that is not suitable for therapeutic use.

In 2008, the Department of Laboratory Medicine at University of Washington Medical Center, Tait Research Laboratory published a document entitled "Production of Recombinant Annexin V from plasmid pET12a-PAPI". It is available online at: https://depts.washington.edu/labweb/Faculty/Tait/108.pdf. The method described is highly similar to the methodology proposed by Kumar. The method expresses Annexin A5 in recombinant *E. coli* host cells in 1 L cultures, pelleting the cells, resuspending the cells in presence of a homogenisation/lysis buffer consisting of 50 mM Tris HCl, 10 mM $CaCl_2$) at pH 7.2, and then breaking the cells via sonication to release the Annexin A5 protein. The added $CaCl_2$) causes the Annexin A5 to bind, in a calcium-dependent manner, to the cell membranes in the debris, and then the mixture is subjected to a first purification centrifugation step of 20 minutes, after which the supernatant was discarded and the pellet containing the cell debris and the bound Annexin A5 was recovered. Annexin A5 was released from the pellet using EDTA, and followed by a second purification centrifugation step of 20 minutes and collection of the Annexin A5 in the supernatant. Then followed a dialysis step to change the buffer for Annexin A5 to Tris HCl at pH 8.0, before the further step of anion exchange on a Mono Q column, and elution of Annexin A5 using a salt gradient. The present applicant has realised that the numerous limitations and shortcomings in the method of Kumar also applies to this method.

In 2014, a further method for the purification of Annexin A5 was proposed in Marder et al., 2014, *BMC Biotechnology*, 14:33 entitled "Production of recombinant human annexin V by fed-batch cultivation". Marder et al., reports that its method is a fed-batch method to produce recombinant human annexin V in large scale, and it is proposed that this method may expand the commercial utilities for recombinant human Annexin A5 to applications such as in vivo imaging studies.

Yet again, the method of Marder et al, is highly similar to the 1991 method of Kumar and the 2008 method of the Department of Laboratory Medicine at University of Washington Medical Center. Marder et al expresses Annexin A5 in recombinant *E. coli* host cells in 1 L cultures, held in 2 L tanks. As discussed (in the Purification section of the Methods of Marder et al), the collected cells were resuspended in presence of a homogenisation/lysis buffer (buffer A) consisting of 50 mM Tris HCl, 10 mM $CaCl_2$) at pH 7.2, and then the cells were broken via sonication to release the Annexin A5 protein. The added $CaCl_2$) causes the Annexin A5 to bind, in a calcium-dependent manner, to the cell membranes in the debris, and then the mixture is subjected to a first purification centrifugation step of 30 minutes, after which the supernatant was discarded and the pellet containing the cell debris and the bound Annexin A5 was recovered. Annexin A5 was released from the pellet using EDTA, and followed by a second purification centrifugation step of 30 minutes and collection of the Annexin A5 in the supernatant. Then followed a dialysis step to change the buffer for Annexin A5 to Tris HCl at pH 8.0, before a third purification centrifugation step of 20 minutes to remove residual precipitate and then the further step of anion exchange on a Mono Q column, and elution of Annexin A5 using a salt gradient. Again, the present applicant has realised that the numerous limitations and shortcomings in the method of Kumar also applies to this method.

The 1997 method of Kumar, the 2008 method of the Department of Laboratory Medicine at University of Washington Medical Center, and the 2014 method of Marder et al, clearly show that the art had developed and established an approach to the production and purification of Annexin A5 products for commercial purposes, although the limitation and shortcomings of these methods were unappreciated in the art, with no readily available alternative.

All of these prior art methods for Annexin A5 recovery have been demonstrated only at a lab-scale process and are incapable of being adopted for scale-up or taking into account industry standards or equipment available at larger scale. The processes have inherent drawbacks making them unsuitable for large scale manufacturing. In particular, a highly limiting features of these prior art processes are the two or (in the case of 2014 method of Marder et al.) the three high G-force centrifugations that the processes require where the Annexin A5 is alternatively in solution or as precipitate. Applying just two centrifugation steps to the processing of one 1000 L batch can be reasonably estimated to result in a process that would take about 12 weeks with 12 hour daily shift in any well-equipped bio-manufacturing facility, resulting in unacceptably high production costs. See Comparative Example 1.

Accordingly, it is an object of the present invention to provide methodological steps for the purification and recovery of Annexin A5 that are efficient and cost-effective for the a manufacturing process that is operated on a commercial scale (e.g. recombinant host cell cultures having a culture volume of about 1000 L or more), and further to overcome the drawback of loss of yield and low purity (including endotoxin contamination) suffered by the prior art processes.

It is also an object of the invention to provide pharmaceutical grade Annexin A5 products that are produced by methods of the present invention.

SUMMARY OF THE INVENTION

The applicant has made numerous developments and improvements to a process for the production of a protein comprising the sequence of Annexin A5 (AnxA5), and has devised several highly efficient purification steps, which may be used independently and/or used in combination to improve existing processes. Most preferably, the process for production of Annexin A5 contains all of the developed process steps.

In particular, the applicant's developments provide the possibility of a highly efficient process for the recovery of the AnxA5 protein thorough a method in which the AnxA5 protein preferably remains in solution throughout the process (except when temporarily bound to chromatographic resins). That is to say, the applicant's developments provide a process for the recovery of the AnxA5 protein that can be performed preferably without the requirement to apply any purification centrifugation steps to AnxA5 protein following the release of the AnxA5 protein from a host cell. This has a huge industrial benefit as high G-force centrifugations to collect precipitates are difficult, slow and expensive to apply in large scale biopharmaceutical manufacturing plants. Further, this means that the processes of the present invention can all be performed without relying on the ability of Annexin A5 to bind to membranes (e.g. host cells membranes and/or liposomes) which can often cause the Annexin A5 to co-purify with undesirable contaminants such as endotoxin.

Accordingly, the process can be applied to the processing of high volume (e.g. about 100 L, 500 L, 1,000 L, 5,000 L, 10,000 L, 50,000 L, 100,000 L or higher) cultures of host cells in a highly time-efficient way without the bottleneck caused by one or more purification centrifugation steps. For example, it may be preferred that the purification process is conducted in, or in less than, 5, 4, 3, 2 weeks and most typically less than 1 weeks per 1,000 L of host cell culture processed. Yet further, the process can be used, surprisingly, to provide improved yield and/or improved purity (including, for example, improved endotoxin removal) compared to the slower, less efficient, prior art processes.

Accordingly, a first aspect of the present invention provides an improved step of protein release from a host cell. More specifically, it provides a process for the recovery and/or purification of a recombinantly expressed intracellular protein comprising the sequence of Annexin A5 (AnxA5) from an endotoxin-producing host cell with a cell wall, wherein the process comprises releasing the intracellular protein from the host cell, characterised in that the step of releasing the intracellular AnxA5 protein is conducted in the presence of a homogenisation buffer comprising non-ionic detergent. Preferably, the non-ionic detergent is a polysorbate, more preferably a polysorbate selected from Tween20 and Tween80, and most preferably Tween80.

The applicant has also discovered (as discussed further in Example 2, below), contrary to conventional methods in which the successive addition of purification steps leads to an ever increasing loss of yield (as product is lost at each step), that the combination of an anion exchange step and a heparin affinity chromatography step has a surprising benefit of attaining the high purity achieved by the heparin affinity chromatography step alone, but with substantially increased yield (i.e. the recovery is increased from about 30-40% to about 70-90%). This is the direct opposite of what would normally be expected from the combination of purification steps.

Accordingly, a second aspect the present invention provides a process for the recovery and/or purification of a protein comprising the sequence of Annexin A5 (AnxA5), from a solution comprising the AnxA5 protein and one or more impurities, the method comprising subjecting the solution comprising the AnxA5 protein and one or more impurities to an anion exchange resin in order to perform a first anion exchange step, and thereby produce a first anion exchange product which comprises the released AnxA5 protein; and subjecting the first anion exchange product, directly or indirectly, to an affinity chromatography step, thereby to produce a first affinity chromatography product which comprises the released AnxA5 protein.

Preferably, in accordance with the process of the second aspect of the present invention, the affinity chromatography step may comprise the binding of the AnxA5 protein to immobilised heparin, and optionally wherein the binding is promoted by the presence of calcium ions and further optionally, the AnxA5 protein is eluted from the immobilised heparin using an elution buffer containing a calcium ion chelator, such as EDTA.

Additionally, as discussed in Example 3, the applicant has discovered that Tween80 has a particularly advantageous effect (compared to other non-ionic detergents, including other Tweens, such as Tween20) on a heparin affinity chromatography step. The inclusion of Tween 80, for example at around 0.1% (w/v) in the buffers used in the heparin affinity chromatography step can assist in eluting the AnxA5 protein in a single peak, reduce pressure, and prevent precipitation.

Accordingly, a third aspect the present invention provides a process for the recovery and/or purification of a protein comprising the sequence of Annexin A5 (AnxA5), from a solution comprising the AnxA5 protein and one or more impurities, the method comprising subjecting the solution comprising the AnxA5 protein and one or more impurities (which may, or may not be the direct or indirect product of a first anion exchange chromatography capture step, as discussed herein) to a heparin affinity chromatography step in the presence of Tween80 (preferably in the presence of about 0.1% w/v Tween80), thereby to produce a first affinity chromatography product which comprises the released AnxA5 protein.

A fourth aspect of the present invention is based on the applicant's realisation that calcium metal ion chelators (e.g. EDTA) can impact negatively on the efficacy of anion exchange steps. Free EDTA (or other chelator) can bind directly to the anion exchange functional groups, and thereby reduce the capacity and also the separation achieved by an anion exchange step. On the other hand, it is time consuming and therefore also increases costs, to attempt to remove calcium metal ion chelator before an anion exchange step. Therefore, prior art methods involving slow dialysis steps for buffer replacement are inefficient. Further, in the inclusion of the calcium metal ion chelator in the AnxA5 product during the anion exchange step can be an important component to prevent calcium-mediated binding of the AnxA5 protein to impurities, including endotoxin. It would therefore be convenient and efficacious to introduce an additive that blocks or reduces the binding of the calcium ion chelator to the anion exchange resin, which would allow the anion exchange step to be performed without inconvenience and cost associated with dialysis, and without preventing the beneficial effect of the calcium metal ion chelator during the anion exchange step.

The applicant has realised that this can be achieved by the inclusion in the AnxA5 protein product, prior to anion exchange, or one or more types of additional selected metal ions, wherein the additional selected metal ions are selected such that the calcium metal ion chelator has a binding affinity for the selected metal ions that is greater than its binding affinity for the anion exchange resin, but less than its binding affinity for calcium ions. The selection of the appropriate additional metal ions will depend on the nature of the calcium ion chelator and the nature of the anion exchange resin. For example, in the case of using EDTA as a calcium ion chelator, $Mg^{2+}$ ions are generally suitable to achieve the object of the present invention, and can be added to the AnxA5 protein product prior to an anion exchange step.

Accordingly, a fourth aspect of the present invention provides a process for the recovery and/or purification of a protein comprising the sequence of Annexin A5 (AnxA5) from a composition that comprises the AnxA5 protein and a calcium metal ion chelator, characterised in that the process comprises subjecting the composition to an anion exchange resin in order to perform an anion exchange step and thereby recover and/or purify the AnxA5 protein from the composition, and further characterised in that the anion exchange step is conducted in the presence of additional selected metal ions, wherein the additional selected metal ions are selected such that the calcium metal ion chelator has a binding affinity for the selected metal ions that is greater than its binding affinity for the anion exchange resin, but less than its binding affinity for calcium ions.

A fifth aspect of the present invention provides a composition comprising an AnxA5 protein, wherein the composition is the direct, or indirect product of (or is directly or indirectly obtainable by) a process according to any of the first, second, third or fourth aspects of the present invention. Optionally, the composition is a pharmaceutically acceptable and/or veterinarily acceptable composition.

The sixth aspect of the present invention also provides the composition of the fifth aspect of the present invention for use in medicine. To put it another way, the sixth aspect of the present invention provides a method comprising administering to a human or animal in need thereof a therapeutically effective amount of a composition of the fifth aspect of the present invention.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and further, aspects of the present invention will be better appreciated and understood when considered in conjunction with the following description and the accompanying drawings. It should be understood, however, that the following description, while indicating various aspects and embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

DESCRIPTION OF THE FIGURES

FIG. 1 shows the sequence SEQ ID NO: 1, which is the sequence of human Annexin A5.

FIG. 3 provides a process flow chart for the exemplified AX capture chromatography.

FIG. 4 shows the process flow chart for the exemplified Intermediate Affinity Chromatography.

FIG. 5 shows the process flow chart for the exemplified AX Polishing Chromatography step.

FIG. 6 shows the process flow chart for exemplified ultra/diafiltration and formulation of Annexin A5.

FIGS. 7A-7B show the results of Example 3, which demonstrates the impact of Tween80 on heparin affinity chromatography purification of Annexin A5, wherein FIG. 7A shows the results for Test 1 (without Tween80), and FIG. 7B shows the results for Test 2 (with Tween80).

DETAILED DESCRIPTION OF THE INVENTION

A. Annexin A5 Protein

Figure 2:
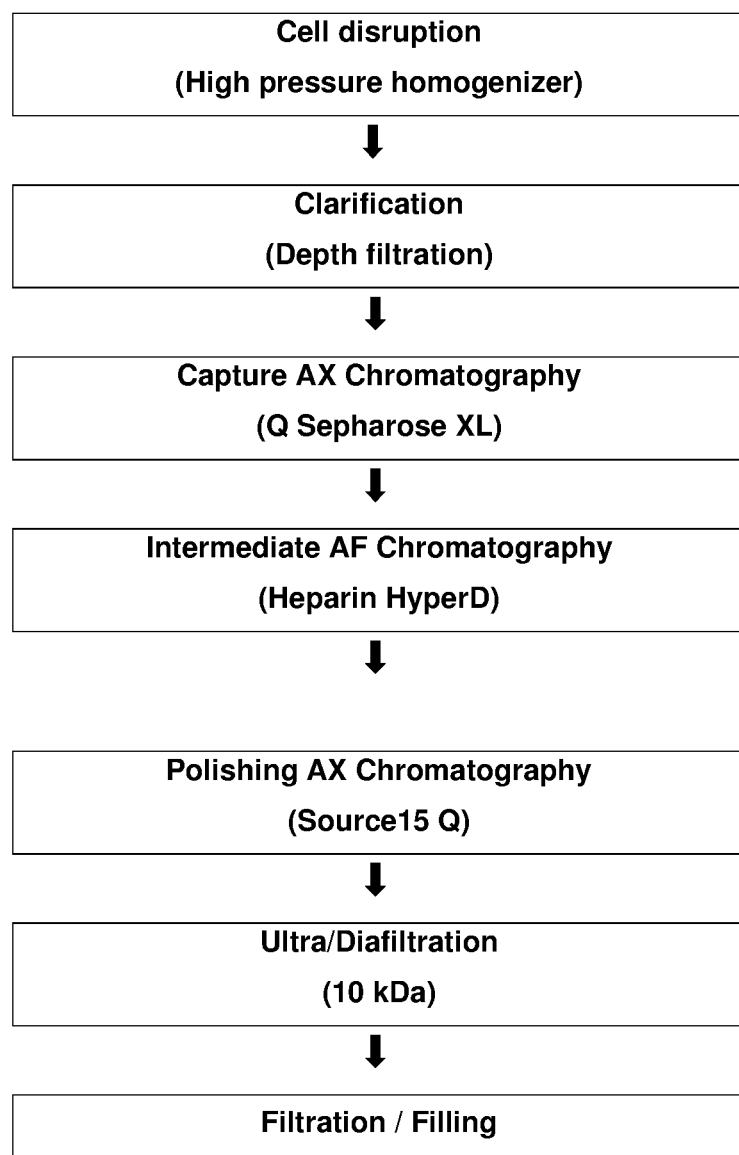
FIG. 2 shows a schematic flow chart of the exemplified complete manufacturing process for Annexin A5.

The present invention relates to methods for the purification and/or recovery of a protein comprising the sequence of Annexin A5 (AnxA5), and products and formulations thus produced comprising the AnxA5 protein.

In accordance with one embodiment of the present invention, the AnxA5 protein that is purified and/or recovered may comprise, consist essentially of, or consist of, a protein having the sequence of human Annexin A5 (SEQ ID NO:1, as shown in FIG. 1), either with or without the N-terminal methionine.

In another embodiment, the AnxA5 protein that is purified and/or recovered may comprise, consist essentially of, or consist of, a variant or mutant of a protein having the sequence of human Annexin A5 (SEQ ID NO:1, as shown in FIG. 1), either with or without the N-terminal methionine. For example, the variant or mutant may differ from SEQ ID NO: 1 (either with, or without, the N-terminal methionine) at any one or more positions, such as at, or up to, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160 or more positions.

Thus, a variant or mutant of Annexin A5 may be a protein wherein at one or more positions there have been amino acid insertions, deletions, or substitutions, either conservative or non-conservative. Preferably, the changes result in a protein whose basic properties to function in an equivalent manner to Annexin A5 have not significantly been changed. "Significantly" in this context means that one skilled in the art would say that the properties of the variant may still be different but would not be unobvious over the ones of the original protein.

Preferably the isoelectric point (pI) of the variant or mutant is not altered, compared to the unmodified protein, or is not modified by more than 1, 0.9, 0.8, 0.7, 0.6, 0.5, 0.4, 0.3, 0.2 or 0.1 pH units.

In a preferred embodiment, the AnxA5 protein is capable of binding to phosphatidylserine on a biological membrane, preferably to a level that is at least 10%, 20%, 30%, 40%, 50%, 60%, 70%, 80%, 90%, 95%, 99% or about 100% of that displayed by human Annexin A5 (SEQ ID NO:1) under the same conditions. A suitable method for measuring Annexin A5 binding to phosphatidylserine on a biological membrane is known in the art (Vermes et al. (1995) *J Immunol Methods*, 184(1): p. 39-51).

By "conservative substitutions" is intended combinations such as Gly, Ala; Val, Ile, Leu; Asp, Glu; Asn, Gln; Ser, Thr; Lys, Arg; and Phe, Tyr.

Variants and mutants may be made using the methods of protein engineering and site-directed mutagenesis which are well known in the art.

In a further embodiment, the AnxA5 protein that is purified and/or recovered may be a dimer of a protein that comprises, consists essentially of, or consists of, a protein having the sequence of human Annexin A5 (SEQ ID NO:1, as shown in FIG. 1), either with or without the N-terminal methionine, or a variant or mutant thereof as described above.

In a further embodiment, the AnxA5 protein that is purified and/or recovered may be a fusion protein, which fusion protein comprises, consists essentially of, or consists of: (a) one or more protein sequences comprising the sequence of fusion partner that is/are fused to; (b) one or more protein sequences that comprises, consists essentially of, or consists of, a protein having the sequence of human Annexin A5 (SEQ ID NO:1, as shown in FIG. 1), either with or without the N-terminal methionine, or a variant or mutant thereof, or dimer as described above. For example, without limitation, the fusion protein may have a general structure selected from:

in the case of the fusion of two amino acid sequences, for example: H$_2$N-(a)-(b)-COOH; or H$_2$N-(b)-(a)-COOH; or in the case of the fusion of three amino acid sequences, for example: H$_2$N-(a)-(b)-(a)-COOH; or H$_2$N-(b)-(a)-(b)-COOH; or H$_2$N-(a)-(b)-(b)-COOH; or H$_2$N-(b)-(b)-(a)-COOH; or H$_2$N-(a)-(a)-(b)-COOH; or H$_2$N-(b)-(a)-(a)-COOH; or in the case of the fusion of four amino acid sequences, for example: H$_2$N-(a)-(a)-(a)-(b)-COOH; or H$_2$N-(a)-(a)-(b)-(a)-COOH; or H$_2$N-(a)-(b)-(a)-(a)-COOH; or H$_2$N-(b)-(a)-(a)-(a)-COOH; or H$_2$N-(a)-(a)-(b)-(b)-COOH; or H$_2$N-(a)-(b)-(a)-(b)-COOH; or H$_2$N-(b)-(a)-(a)-(b)-COOH; or H$_2$N-(a)-(b)-(b)-(a)-COOH; or H$_2$N-(b)-(a)-(b)-(a)-COOH; or H$_2$N-(b)-(b)-(a)-(a)-COOH; or H$_2$N-(b)-(b)-(b)-(a)-COOH; or H$_2$N-(b)-(b)-(a)-(b)-COOH; or H$_2$N-(b)-(a)-(b)-(b)-COOH; or H$_2$N-(a)-(b)-(b)-(b)-COOH; or in the case of the fusion of five amino acid sequences, for example: or H$_2$N-(a)-(a)-(a)-(a)-(b)-COOH; or H$_2$N-(a)-(a)-(a)-(b)-(a)-COOH; or H$_2$N-(a)-(a)-(b)-(a)-(a)-COOH; or H$_2$N-(a)-(b)-(a)-(a)-(a)-COOH; or H$_2$N-(b)-(a)-(a)-(a)-(a)-COOH; or H$_2$N-(a)-(a)-(a)-(b)-(b)-COOH; or H$_2$N-(a)-(a)-(b)-(a)-(b)-COOH; or H$_2$N-(a)-(b)-(a)-(a)-(b)-COOH; or H$_2$N-(b)-(a)-(a)-(a)-(b)-COOH; or H$_2$N-(a)-(a)-(b)-(b)-(a)-COOH; or H$_2$N-(a)-(b)-(a)-(b)-(a)-COOH; or H$_2$N-(b)-(a)-(a)-(b)-(a)-COOH; or H$_2$N-(a)-(b)-(b)-(a)-(a)-COOH; or H$_2$N-(b)-(a)-(b)-(a)-(a)-COOH; or H$_2$N-(b)-(b)-(a)-(a)-(a)-COOH; or H$_2$N-(a)-(a)-(b)-(b)-(b)-COOH; or H$_2$N-(a)-(b)-(a)-(b)-(b)-COOH; or H$_2$N-(b)-(a)-(a)-(b)-(b)-COOH; or H$_2$N-(a)-(b)-(b)-(a)-(b)-COOH; or H$_2$N-(b)-(a)-(b)-(a)-(b)-COOH; or H$_2$N-(b)-(b)-(a)-(a)-(b)-COOH; or H$_2$N-(a)-(b)-(b)-(b)-(a)-COOH; or H$_2$N-(b)-(a)-(b)-(b)-(a)-COOH; or H$_2$N-(b)-(b)-(a)-(b)-(a)-COOH; or H$_2$N-(b)-(b)-(b)-(a)-(a)-COOH; or H$_2$N-(b)-(b)-(b)-(b)-(a)-COOH; or H$_2$N-(b)-(b)-(b)-(a)-(b)-COOH; or H$_2$N-(b)-(b)-(a)-(b)-(b)-COOH; or H$_2$N-(b)-(a)-(b)-(b)-(b)-COOH; or H$_2$N-(a)-(b)-(b)-(b)-(b)-COOH, wherein (a) and (b) are as defined above in this paragraph. In the case of multiple fusion partner proteins, as defined by (a), the multiple fusion partners may be same or different. Any fusion partner of interest may be used. For example the fusion partner polypeptide sequence(s) may be suitable to extend the half-life of the molecule within a patient's circulatory system and/or add further functionality to the molecule, such as to add additional therapeutic properties (e.g. anticoagulant, cell inhibition and/or killing, etc.). In the case of fusion proteins comprising multiple protein sequences having the sequence of human Annexin A5 (SEQ ID NO:1, as shown in FIG. 1), either with or without the N-terminal methionine, or a variant or mutant thereof, or dimer as described above, as defined by (b), those proteins may be the same or different.

In accordance with a further embodiment of the present invention, the AnxA5 protein that is purified and/or recovered may be a protein that comprises, consists essentially of, or consists of, the sequence of Annexin A5 or functional variant or mutant thereof as selected from:

a) human Annexin A5 (SEQ ID NO:1), with or without the N-terminal methionine;

b) a mammalian orthologue of human Annexin A5;

c) an allelic or genetic variant of a) or b);

d) a protein which is more than 50%, 60%, 70%, 75%, such as more than 80%, 85%, more than 90%, or even more preferably more than 95% or 99% identical to any of a), b) or c);

e) a dimer of any of a), b), c) or d); or f) a fusion protein comprising one or more fusion partners fused to any of a), b), c), d) or e).

In particular embodiments, the AnxA5 protein is a functional variant or mutant of Annexin A5 that is more than 50%, 60%, 70%, 75%, such as more than 80%, 85%, more than 90%, or even more preferably more than 95% or 99% identical to human Annexin A5, SEQ ID NO:1, with or without the N-terminal methionine.

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:1 (the length of the sequence set forth in SEQ ID NO:1 is 320) and the number of matches is 288, then the sequence has a percent identity of 90 (i.e., 288÷320*100=90) to the sequence set forth in SEQ ID NO:1.

The AnxA5 protein may be a dimer of Annexin A5 (such as DiAnnexin) or a functional variant or mutant thereof. DiAnnexinA5 is disclosed in WO 02/067857.

Preferably, the AnxA5 protein does not include a His-tag, and its recovery and purification is not achieved using a step of affinity binding to a His-tag sequence.

A His-tag is a polyhistidine amino acid motif in proteins that typically consists of at least six histidine (His) residues, and is often (although not necessarily) at the N- or C-terminus of the protein. Polyhistidine-tags are often used for affinity purification of polyhistidine-tagged recombinant proteins expressed in *Escherichia coli* and other prokaryotic expression systems, by incubation with an affinity resin containing bound bivalent nickel or cobalt ions, which are available commercially in different varieties. These resins are generally sepharose/agarose functionalised with a chelator, such as iminodiacetic acid (Ni-IDA) and nitrilotriacetic acid (Ni-NTA) for nickel and carboxylmethylaspartate (Co-CMA) for cobalt, which the polyhistidine-tag binds with micromolar affinity. The resin is then typically washed with phosphate buffer to remove proteins that do not specifically interact with the cobalt or nickel ion. With Ni-based methods, washing efficiency can be improved by the addition of 20 mM imidazole (proteins are usually eluted with 150-300 mM imidazole).

Although the His-tag approach is convenient for purification, the presence of non-native polyhistidine motifs in therapeutic proteins, including AnxA5 protein, is undesirable, as it can lead to adverse patient reactions, such as immunological responses. Alternatively, it is burdensome, time consuming, and costly to attempt to remove His-tags motifs after protein production, and in practice protein preparations from which His-tags have been removed would typically retain one or more foreign histidine residues.

Consequently, preferably, the AnxA5 protein does not include a His-tag, and its recovery and purification is not achieved using a step of affinity binding to a His-tag sequence.

The AnxA5 protein of the present invention may be, or may not be (preferably, is not), a variant of a variant or mutant of a protein having the sequence of human Annexin A5 that is modified to comprise one or more, such as up to twenty, RGD (arginine-glycine-aspartate) motifs, as disclosed in WO 2010/140886, the contents of which are incorporated herein by reference. As described in WO 2010/140886, the addition of one or more RGD motifs can be used to enhance phagocytosis by using AnxA5 variants that bind to phosphatidylserine (PS) on apoptotic cells and activate phagocytes to engulf the apoptotic cell instead of inhibiting phagocytosis.

B. Host Cell Culture

The AnxA5 protein can be expressed recombinantly in a host cell culture. Preferred host cell cultures that express AnxA5 protein, according to the present invention, are cultures that are on a commercial scale for AnxA5 protein production, such as cultures having a culture volume of about 100 L, about 200 L, about 300 L, about 400 L, about 500 L, about 600 L, about 700 L, about 800 L, about 900 L, about 1,000 L, about 2,000 L, about 3,000 L, about 4,000 L, about 5,000 L, about 6,000 L, about 7,0000 L, about 8,0000 L, about 9,0000 L, about 10,000 L, about 20,000 L, about 30,000 L, about 40,000 L, about 50,000 L, about 60,000 L, about 70,0000 L, about 80,0000 L, about 90,0000 L, about 100,000 L or higher. The term "about" in that context can include the meaning of ±50%, 40%, 30%, 20%, 10%, 5%, 4%, 3%, 2% or 1% of the stated volume.

Methods for the recombinant expression of a gene of interest are well known in the art.

Typically, a nucleotide sequence encoding an AnxA5 protein will be expressed recombinantly in a host cell culture. For example, the sequence encoding the AnxA5 protein may be introduced into a host cell by transformation of the host cell with a plasmid or other vector comprising the sequence encoding the AnxA5 protein and optionally, the sequence encoding the AnxA5 protein will be integrated into the host cell chromosome (or plastome) or maintained on an replicable extrachromosomal vector.

Accordingly, a host cell can be transformed with a polynucleotide vector construct comprising a sequence encoding the AnxA5 protein.

The host cell can be either prokaryotic or eukaryotic.

Bacterial cells are preferred prokaryotic host cells in the context of the present invention. Bacterial host cells may, for example, be gram-positive or gram-negative host cells (although gram-neutral and gram-variable bacteria may also be used). Examples of gram-negative bacteria include, but are not limited to, *Escherichia coli, Salmonella, Shigella, Pseudomonas, Neisseria, Haemophilus influenzae, Bordetella pertussis* and *Vibrio cholera*.

At least in the context of the first aspect of the present invention, and optionally in the context of all aspects of the present invention, the host cell is an endotoxin-producing host cell with a cell wall, and thus is typically a gram-negative bacteria, such as *E. coli*, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343).

For the avoidance of doubt, the term "endotoxin-producing host cell with a cell wall" can be construed to exclude yeast, such as *Saccharomyces cerevisiae*, and other eukaryotic cells.

A further particularly-preferred endotoxin-producing strain of *E. coli* includes strain BL21 (DE3) (e.g. as is widely commercially-available, and as described in Marder et al., 2014, *BMC Biotechnology*, 14:33). However, the applicant has found that Annexin A5 expressed from strain BL21 (DE3) surprisingly displays unexpectedly high levels of undesirable post-translational gluconoylation, such that about 40% of the Annexin A5 protein was gluconoylated. This is much higher than the level of gluconoylation for most other recombinantly-expressed proteins in BL21 (DE3), which typically show levels of about only 5-10% gluconoylation. It is therefore even more preferred that the endotoxin-producing strain of *E. coli* is a strain of BL21 (DE3) that is engineered reduce the level of gluconoylation of the AnxA5 protein, for example by overexpressing phosphogluconolactonase (PGL), as described in Aon et al. (*Appl. Env. Microbiol.*, 2008, 74(4): 950-958; the contents of which are incorporated herein by reference) and thereby suppress the post-translational gluconoylation of recombinantly-expressed protein, and so suppressing the formation of gluconoylated variants of AnxA5 protein to level below 40%, such as below 30%, 20%, 10%, 9%. 8%, 7%, 6%, 5%, 4%, 3%, 2%, or 1%, and preferably substantially 0%.

Typically, the bacterial host cell for use in the present invention is a bacterial host cell with a wall, and therefore preferably excludes cells lacking a cell wall and (in the case of gram-negative bacteria) the outer membrane, such as a spheroplast (such as described in Liu et al, 2006, J. Exp. Microbiol., 9: 81-85; the contents of which are incorporated herein by reference). Spheroplasts, within the context of the present application, are not endotoxin-producing host cells, and do not have a cell wall. Spheroplasts are entirely unsuitable for commercial scale production, in particularly due to their sensitivity and fragility in the absence of a cell wall which seriously restricts their ability to be productively grown in large volume cultures.

Optionally, the host cell is an endotoxin-producing host cell with a cell wall that is incapable of being lysed by osmotic shock and/or freeze/thaw treatments.

In a further option, the host cell culture is a culture wherein the host cell is not, or has not been, cultured in the presence of an antibiotic to which it has no resistance, and optionally not in the presence of any antibiotic. Specific antibiotics to be avoided, in one embodiment, are antibiotics that result in the formation of spheroblasts, such as ampicillin.

Eukaryotic host cells may include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Typical prokaryotic vector plasmids are: pUC18, pUC19, pBR322 and pBR329 available from Biorad Laboratories (Richmond, Calif., USA); p Trc99 A, pKK223-3, pKK233-3, pDR540 and pRIT5 available from Pharmacia (Piscataway, N.J., USA); pBS vectors, Phagescript vectors, Bluescript vectors, pNH8 A, pNH16 A, pNH18 A, pNH46 A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HISS, TRP1, LEU2 and URA3. Plasmids pRS413-416 are Yeast Centromere plasmids (YCps).

Methods well known to those skilled in the art can be used to construct expression vectors containing the AnxA5 protein coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or E. coli DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the DNA encoding the AnxA5 protein is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Transformation of appropriate cell hosts with a DNA construct comprising a sequence encoding the AnxA5 protein is accomplished by well-known methods that typically depend on the type of vector used.

With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual*, $3^{rd}$ Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 µFD.

Methods for transformation of yeast by electroporation are disclosed in Becker & Guarente (1990) *Methods Enzymol.* 194, 182.

Physical methods may be used for introducing DNA into animal and plant cells. For example, microinjection uses a very fine pipette to inject DNA molecules directly into the nucleus of the cells to be transformed. Another example involves bombardment of the cells with high-velocity microprojectiles, usually particles of gold or tungsten that have been coated with DNA.

Successfully transformed cells, i.e. cells that contain a DNA construct comprising a sequence encoding the AnxA5 protein, can be identified by well-known techniques. For example, one selection technique involves incorporating into the expression vector a DNA sequence (marker) that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

The marker gene can be used to identify transformants but it is desirable to determine which of the cells contain recombinant DNA molecules and which contain self-ligated vector molecules. This can be achieved by using a cloning vector where insertion of a DNA fragment destroys the integrity of one of the genes present on the molecule. Recombinants can therefore be identified because of loss of function of that gene.

Another method of identifying successfully transformed cells involves growing the cells resulting from the introduction of an expression construct comprising a sequence encoding the AnxA5 protein to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well-known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, the transformed host cells themselves can be cultured to provide a culture transformed host cells expressing the AnxA5 protein. The culture may be a monoclonal (clonally homogeneous) culture, or a culture derived from a monoclonal culture, in a nutrient medium.

The culture of transformed host cells expressing AnxA5 protein is grown under suitable growth conditions until a desired cell density is achieved, which is typically selected to balance productivity with time and cost associated with the culture phase, and then the cells are typically harvested. The optimal time for cell harvesting can be determined empirically for any given culture.

Harvesting may, for example, involve the collection of host cells (which are typically intact, and which typically retain substantially all (e.g. more than 80%, 90%, 95%, 99% or 100%) of the AnxA5 protein intracellularly) from the culture medium. This can commonly be achieved by centrifugation or filtration, to collect the cultured host cells in the form of a biomass. In the case of centrifugation, the supernatant can be discarded, and cell pellets can be transferred directly or indirectly (e.g. following storage, such as by freezing) to the cell culture homogenisation stage.

C. Cell Culture Homogenisation

As discussed above, a first aspect of the present invention provides an improved step of protein release from a host cell. More specifically, it provides a process for the recovery and/or purification of a recombinantly expressed intracellular protein comprising the sequence of Annexin A5 (AnxA5) from an endotoxin-producing host cell with a cell wall, wherein the process comprises releasing the intracellular protein from the host cell, characterised in that the step of releasing the intracellular AnxA5 protein is conducted in the presence of a homogenisation buffer comprising non-ionic detergent.

Preferably, the non-ionic detergent is a polysorbate, more preferably a polysorbate selected from Tween20 and Tween80, and most preferably Tween80. Alternatively, although less preferably, other non-ionic detergent may be used, although it is preferred to avoid (both in the cell culture homogenisation step, and also in any other steps of the process) the use of non-ionic detergents which have a UV absorption $\lambda_{max}$ similar to the absorption maxima of proteins, which is between 275 and 280 nm, as this can interfere with the ability of UV absorption to monitor the presence of protein during the recovery process. In that context, "similar" can include the meaning that the $\lambda_{max}$ is within 10 mn, 9 nm, 8 mn, 7 nm, 6 nm, 5 nm, 4 nm, 3 nm, 2 nm, or 1 nm of the absorption maxima of the AnxA5 protein being purified. Thus, for example, it may be preferred that the non-ionic detergent is not Triton X-100, which has $\lambda_{max}$=275 nm, and so it may be preferred that Triton X-100 is not used in the cell culture homogenisation step and/or any other step of the process of the present invention.

It is to be noted that the non-ionic detergent may be included in the homogenisation buffer that is added to the cells (e.g. the homogenisation buffer may be 'pre-formed' with the non-ionic detergent present); or that the cells may be suspended in the homogenisation buffer without the non-ionic detergent, and then the non-ionic detergent can be added into, and mixed with, the suspended cells in the homogenisation buffer, prior to cell homogenisation to release the intracellular AnxA5 protein.

Preferably the step of releasing the intracellular AnxA5 protein is conducted in the presence of a homogenisation buffer comprising an amount of non-ionic detergent that is effective to reduce (such as by 50%, 60%, 70%, 80%, 90%, 95%, 98%, 99% or more) or prevent the binding between Annexin A5 and endotoxin. Endotoxin levels may be measured by methods well known and established in the art, for example by the limulus amebocyte lysate (LAL) test.

For example the homogenisation buffer may comprise 0.01 to 10% (w/w) non-ionic detergent, such as 0.02 to 5% (w/w), 0.05 to 2% (w/w), or about 1% (w/w) non-ionic detergent. The term "about" in that context, can include the meaning of ±0.5%, 0.4%, 0.3%, 0.2% or 0.1% (w/w).

It is preferable that no calcium ions or ionisable calcium compounds (such as $CaCl_2$)) are added or included in the homogenisation buffer. Accordingly, it is preferable that the free calcium ion concentration in the homogenisation buffer at the time of releasing the intracellular AnxA5 protein from the host cell is lower than 10 mM, preferably lower than 5 mM, 4 mM, 3 mM, 2 mM or 1 mM, more preferably lower than 500 µM, 400 µM, 300 µM, 200 µM, 100 µM, 50 µM, 40 µM, 30 µM, 20 µM, 10 µM, 5 µM, 4 µM, 3 µM, 2 µM, 1 µm or substantially zero.

In one embodiment, the homogenisation buffer may comprise a calcium metal ion chelator. It may be preferred, in view of optional subsequent steps involving enzymatic treatment in which such enzymes use $Mg^{2+}$ as a co-factor, to select a calcium ion chelator that does not strongly bind $Mg^{2+}$, such as ethylene glycol tetraacetic acid (EGTA). Alternatively, the optional subsequent steps involving enzymatic treatment in which such enzymes use $Mg^{2+}$ as a co-factor may be substituted with other steps not requiring $Mg^{2+}$. In that case, any calcium ion chelator, such as EGTA or ethylenediaminetetraacetic acid (EDTA) may be included in the homogenisation buffer.

Optionally, the concentration of free calcium ions and/or the amount of calcium metal ion chelator in the homogenisation buffer is (or are) in an amount effective to reduce (such as by 50%, 60%, 70%, 80%, 90%, 95%, 98%, 99% or more) or prevent the binding between Annexin A5 and components of the cell membrane and/or wall of the host cell, such as compared to the level of binding that would be observed in the presence of a homogenisation buffer consisting of 50 mM Tris HCl, 10 mM $CaCl_2$) at pH 7.2.

For example, the homogenisation buffer in accordance with the first aspect of the present invention may comprise 0.01 to 500 mM, such as 0.05 to 100 mM, 0.5 to 20 mM, 1 to 15 mM, 2 to 10 mM, or about 4 mM calcium metal ion chelator, and preferably wherein the calcium metal ion chelator is EDTA or EGTA.

As discussed above, the step of cell culture homogenisation in accordance with the first aspect of the present invention does not include a centrifugation step for purification and separation of the released AnxA5 protein from the host cell debris. Nevertheless, in order to establish a tolerance to free calcium ions and/or an effective amount of calcium metal ion chelator in the homogenisation buffer, a simple test can be conducted using a centrifugation step on an aliquot of lysed cells. Following cell homogenisation, the aliquot (e.g. 100 mL) of lysed cells is subjected to centrifugation (e.g. at 38,900 g for 30 mins) and then the supernatant and pellet are separated. The amount of AnxA5 protein in the supernatant is determined to give the level of "free" AnxA5 protein. The pellet is resuspended in 50 mM Tris HCl, 20 mM EDTA, pH 7.2, with stirring for 30 mins at 4° C., to release any bound AnxA5 protein, and then centrifuged at 38,900 g for 30 mins at 4° C., and the amount of bound AnxA5 protein that is released into the supernatant is determined to give the level of "bound" AnxA5 protein. In that context, the percentage of binding of AnxA5 to components of the cell membrane and/or wall of the host cell=(level of "bound" AnxA5 protein/(level of "bound" AnxA5 protein+level of "free" AnxA5 protein))×100.

Preferably, as determined by the foregoing method, the percentage of bound AnxA5 in the resultant biomass homogenate is less than 50%, 40%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1% or substantially 0%.

Although referred to herein as a "homogenisation buffer" it is not necessarily essential for the solution to be a pH buffer. However, optionally, the homogenisation buffer may further comprise additional components, including buffers (e.g. Tris) and may optionally be pH adjusted as required, for example to around pH 6-8, more preferably in the range of pH 7-8.5, such as about pH 7.0, 7.1, 7.2, 7.3, 7.4, 7.5, 7.6, 7.7, 7.8, 7.9, 8.0, 8.1, 8.2, 8.3, 8.4, or 8.5. In one embodiment, pH 7.4 may be selected for use.

As discussed above, it may also be preferable, in some options in which subsequent steps include enzymatic treatment with enzymes requiring co-factors such as $Mg^{2+}$, to include the cofactor in the homogenisation buffer.

In one exemplary embodiment, the homogenisation buffer for use in accordance with the first aspect of the present invention comprises, consists essentially of, or consists of an aqueous solution of 50 mM Tris, pH 7.4, 1 mM $MgCl_2$ and 1% (w/w) Tween80.

The process of the first aspect of the present invention may comprise the step of mixing biomass from a culture of host cells in the homogenisation buffer at a concentration of about 1 g to 300 g of biomass (wet weight) per Litre of homogenisation buffer, such as at a concentration of about 10 g to 200 g of biomass per Litre of homogenisation buffer. Exemplary concentrations may be about 10 g/L, 20 g/L, 30 g/L, 40 g/L, 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, or 200 g/L. A resuspension ratio of about 100 g biomass per Litre of homogenisation buffer may be particularly preferred. In that context, the term "about" is intended to include ±5 g/L, 4 g/L, 3 g/L, 2 g/L, or 1 g/L of the stated value.

The mixing typically occurs around room temperature, i.e. typically around 18° C. to 28° C., such at about 19° C., 20° C., 21° C., 22° C., 23° C., 24° C., 25° C., 26° C., or 27° C. It may be preferred to control the temperature during the mixing process to maintain it at, or around (e.g. ±5, 4, 3, 2, or 1° C. of) a temperature selected from the foregoing list, although active temperature control at this stage is usually not required.

Optionally, the homogenisation buffer may also include, or have added to it following mixing with the biomass but prior to host cell homogenisation, one or more enzymes useful in enzymatic treatment. For example, it may be suitable to include or add one or more nuclease enzymes to assist in the degradation of nucleic acids (including DNA and/or RNA) from the host cells, after homogenisation. This will reduce the viscosity of the subsequently-produced homogenate and thereby assist in downstream processing steps. Any suitable enzymes may be used. The enzyme may, for example, be a nuclease, such as a nuclease A, preferably a nuclease A from *Serratia marescens*. One such exemplary enzyme of interest is the Benzonase nuclease, an endonuclease from *Serratia marcescens*, which is available from numerous commercial sources including Merck/Novagen, Sigma Aldrich and the like, which can be used to degrade all forms of DNA and RNA while having no proteolytic activity. It is effective over a wide range of conditions and possesses a high specific activity. The enzyme completely digests nucleic acids to 5'-monophosphate terminated oligonucleotides 2 to 5 bases in length (below the hybridization limit), which is ideal for removal of nucleic acids from recombinant proteins, enabling compliance with FDA guidelines for nucleic acid contamination. The Benzonase enzyme requires 1-2 mM $Mg^{2+}$ for activation, and remains active in the presence of ionic and non-ionic detergents, reducing agents, the protease inhibitor PMSF (1 mM), the chelator EDTA (1 mM) and urea (relative activity depends on specific conditions). The skilled person will be readily able to determine an effective concentration of such nuclease enzymes, although the applicant has identified that Benzonase is effective at least when used prediluted at about 3.3 U per L of host cell culture or at about 1.85 U per L of resuspended biomass. The term "about" in that context may include ±90%, 80%, 70%, 60%, 50%, 40%, 30%, 20%, or 10% of the stated number of units.

The step of releasing the intracellular AnxA5 protein from the host cell in the homogenisation buffer can involve any suitable approach to cell homogenisation or lysis. For example, it may comprises lysing, breaking or otherwise homogenising, sonicating, or pressure treating the host cell, such that the cell wall and cell membrane barrier of the host cell is disrupted and thereby releases the intracellular AnxA5 protein. In certain options of the first aspect of the present invention, this step does not include the use of osmotic shock and/or a freeze-thaw step.

In one preferred embodiment of the first aspect of the present invention, the step of releasing the intracellular AnxA5 protein from the host cell comprises high pressure homogenisation, such as one or more cycles of high pressure homogenisation between about 400 bar and about 2,500 bar, preferably three homogenisation cycles of about 600 bar, or two homogenisations cycles of about 800 bar. In that context, the term "about" can include ±500, 400, 300, 200, 100, 50, 40, 30, 20, or 10 bar of the stated value.

Optionally, for example in situations in which no nuclease enzymes have been added to degrade nucleic acids (for example, where the concentrations of $Mg^{2+}$ in the homogenisation buffer are too low, such as because of the inclusion of a $Mg^{2+}$ chelator), then it may be beneficial to include multiple additional rounds of high pressure homogenisation (e.g. from 2 to 4 rounds, at a pressure within the range of from about 600 to 2500 bars) to degrade the nucleic acids and reduce the viscosity of the homogenate.

Accordingly, following the cell homogenisation the step of releasing the intracellular AnxA5 protein may create a biomass homogenate comprising the released AnxA5 protein. Preferably, the biomass homogenate is homogeneous, by which we include the meaning that at least 80%, preferably at least 90%, more preferably at least 95%, 96%, 97%, 98%, 99% or substantially 100% of the cells of the biomass are disintegrated.

Depending on the cell homogenisation approach applied, the technique may cause an increase in the temperature of the homogenate. It may be preferable to operate the cell homogenisation technique in such a way and/or apply temperature control, to prevent undesirable increases in temperature. However, for example, in the case that the homogenate contains an enzymatic treatment, such as Benzonase, then it may be advantageous to use the temperature increase to move closer to, and preferably within, the enzyme's optimum temperature range. In the case of Benzonase, temperatures in the range of about 36 to 40° C. may be particularly suitable.

In the case that the cell homogenisation procedure includes enzymatic treatment with an enzyme requiring a metal ion co-factor (e.g. $Mg^{2+}$), and further in the case that the homogenisation buffer excluded the calcium metal ion chelator, then in one option, the calcium ion chelator may be added after the completion of the enzymatic treatment. This may occur before or after a clarification step, as discussed below.

Following cell homogenisation, the biomass homogenate typically further comprises one or more (typically all) of the impurities selected from the group consisting of host cell proteins, host cell wall components, host cell membrane components, host cell nucleic acid, and endotoxin.

It is preferred that the viscosity of the homogenate is adequately low to assist in downstream processing steps.

D. Clarification of the Homogenate

Optionally, and in a preferred embodiment, then following the production of the biomass homogenate it is treated with a clarification step.

Accordingly, in a further embodiment of the first aspect of the present invention, the process further comprising the step of clarifying the biomass homogenate, and thereby producing a clarified product comprising the released AnxA5 protein. This step is conducted to reduce the content of nucleic acids and, additionally, to obtain a particle-reduced solution which can be applied to subsequent purifications steps such as capture chromatography as discussed further below.

Any suitable clarification step or combination of steps can be performed. For example, the clarification process may comprise (preferably, subsequent to the nuclease treatment), the step of passing the biomass homogenate comprising the released AnxA5 protein through a filter, such as a cellulose or polypropylene filter, wherein the filter effluent is the clarified product comprising the released AnxA5 protein.

Preferably the filter is a depth filter, and/or preferably the filter has a cut off of less than 4 µm, such as a cut-off of less than 3 µm, 2 µm or 1 µm, and most preferably a cut off within the range of 0.2 to 0.6 µm. For example, the homogenate may be clarified by filtration using a 0.6-0.2 µm cut off depth filter, examples of which are commercially available, e.g. such as available as the cellulose-based Cuno 60 SP depth filters. Other depth filters found to provide good performance (i.e. good filtration without product loss), albeit less so that the preferred cellulose Cuno 60 SP depth filters with 0.6-0.2 µm cut off, include a cellulose+kieselguhr filter with a 0.5 µm cut-off (e.g. PR12 UP available from Begerow); a polypropylene filter with a 1.2 µm cut off (e.g. Sartopure PP2 available from Sartorius); a cellulose filter with a 0.1 µm cut off (e.g. Sartoclear S9 available from Sartorius); a polypropylene filter with a 0.65 µm cut off (e.g. Sartopure PP2 available from Sartorius); and a cellulose filter with a 0.2-0.5 µm off (e.g. EK 1P or EKM-P both available from Pall, which were good but slow). Further tests showed that filters with larger cut offs (e.g. >4 µm) achieved only moderate particle removal, and so are less preferred.

It has also been found by the applicant that positively charged cellulose based filters additionally reduce DNA content in the clarified homogenate, and therefore may represent a particularly preferred class of filters for use in the clarification step.

Moreover, it has been found that cellulose-based filters require a smaller filter area to provide effective clarification than do corresponding polypropylene filters. This may be a further reason to particularly prefer the cellulose-based class of filters for use in the clarification step.

The selection of filter area can also depend on the extent and nature of homogenisation used. For example, the applicant has found that in the case of cell homogenisation being performed by three homogenisation cycles of about 600 bar then a filter area of about 60 $cm^2$ per 1 L of homogenate is suitable, whereas in the case of cell homogenisation being performed by two homogenisations cycles of about 800 bar then a filter area of about 180 $cm^2$ per 1 L of homogenate is suitable. Accordingly, the depth filter may optionally be selected to have an area of from 10 to 500 $cm^2$ per L of homogenate clarified, such as from 30 to 400 $cm^2/L$, from 40 to 250 $cm^2/L$, from 50 to 200 $cm^2/L$ or from 60 to 180 $cm^2/L$, such as from 50-100 $cm^2/L$, or 60-80 $cm^2/L$; or from 120-240 $cm^2/L$, or 150-210 $cm^2/L$.

After clarification, the clarified product may be further adjusted by the addition of one or more further additives in readiness for subsequent steps. For example, it may be suitable to condition the clarified product by the addition of one or both of: (a) a non-ionic detergent, such as polysorbate and most preferably Tween80; and (b) a calcium metal ion chelator, such as EDTA, unless the clarified product already contains adequate levels of the chelator by virtue of its inclusion in the homogenisation buffer and/or by its addition after the enzymatic treatment step.

In one exemplary embodiment, the clarified product is diluted about 2-fold with 1% non-ionic detergent (most preferably Tween80), and a calcium ion chelator (most preferably EDTA) is added to a final concentration of about 2 mM.

A further advantageous feature of the process of the present invention is the lack of need for any time-consuming dialysis steps in the clarified product prior to further chromatographic capture steps, such as anion exchange capture as discussed below. Accordingly, in an embodiment of the present invention, the clarified product is not subjected to dialysis prior to chromatographic capture of the AnxA5 protein.

E. Anion Exchange Capture

A process, in accordance with the first aspect of the present invention, may further comprise the step of subjecting the released AnxA5 protein to an anion exchange resin in order to perform a first anion exchange capture step, and thereby produce a first anion exchange product which comprises the released AnxA5 protein.

Generally, protein capture by anion exchange chromatography from bacterial (e.g. *E. coli*) homogenate/lysate is not a first choice strategy since high quantities of host cell proteins (HCP) and DNA bind to the capture resin affecting the binding capacities for the target product and even stressing the resin performance. However, the applicant has determined that the foregoing cell homogenisation and clarification procedures according to the first aspect of the present invention are effective to provide an AnxA5 protein product that can be effectively further purified using anion exchange chromatography.

Accordingly, in one embodiment, the clarified product comprising the released AnxA5 protein as produced by the step of clarification of the homogenate/lysate and/or degradation of nucleic acids, as discussed above, is subjected to the first anion exchange capture step, thereby to produce a first anion exchange product which comprises the released AnxA5 protein.

Optionally, prior to the first anion exchange step, one or more parameters of the environment of the released AnxA5 protein, selected from the group consisting of the pH, the conductivity, the level of calcium ion chelator and the level of non-ionic detergent, is or are adjusted. For example, the AnxA5 protein composition that is subjected to the anion exchange step may be formulated at a pH of about 6.9, optionally ±1, 0.9, 0.8, 0.7, 0.6, 0.5, 0.4, 0.3, 0.2 or 0.1 pH units (in one option, a preferred range is pH 6-8.5, more preferably pH 6.5-7.5, most preferably pH 6.9). The applicant has found that low pH values around this range (e.g. at pH 6) tend to cause the presence of detectable host cell proteins in the eluted product; whereas resolution is somewhat reduced at or above pH 8. The AnxA5 protein composition that is subjected to the anion exchange step may optionally be adjusted to have a conductivity of about 2.8 mS/cm, ±1, 0.9, 0.8, 0.7, 0.6, 0.5, 0.4, 0.3, 0.2 or 0.1 mS/cm. After clarification, the clarified product may be further adjusted by the addition of one or more further additives in readiness for subsequent steps. As already discussed above, it may be suitable prior to the first anion exchange step to condition the AnxA5 protein composition that is subjected to the anion exchange step by the addition of one or both of: (a) a non-ionic detergent, such as polysorbate and most preferably Tween80; and (b) a calcium metal ion chelator, such as EDTA, unless the clarified product already contains adequate levels of the chelator by virtue of its inclusion in the homogenisation buffer and/or by its addition after the enzymatic treatment step. In one exemplary embodiment, the AnxA5 protein composition that is subjected to the anion exchange step is diluted about 2-fold with 1% non-ionic detergent (most preferably Tween80), and a calcium ion chelator (most preferably EDTA) is added to a final concentration of about 2 mM.

In this context, the use of non-ionic detergent and/or calcium metal ion chelator to condition the AnxA5 protein composition that is subjected to the first anion exchange capture step can be highly beneficial in enhancing the separation of the AnxA5 protein from host cell-derived impurities (including cell wall components, cell membrane components, endotoxin, nucleic acids, etc.) by the first anion exchange capture step. For example, the applicant has demonstrated a highly efficient removal of endotoxin (around a 99% reduction) by the first capture anion exchange step when conducted in the presence of non-ionic detergent and calcium metal ion chelator.

Although primarily discussed below in the context of the second anion exchange polishing step, in the option in which a calcium metal ion chelator (e.g. EDTA) is present in the AnxA5 protein composition that is subjected to the first anion exchange capture step, it may also be beneficial to the operation of the first anion exchange capture step include one or more types of additional selected metal ions (not calcium), wherein the additional selected metal ions are selected such that the calcium metal ion chelator has a binding affinity for the selected metal ions that is greater than its binding affinity for the anion exchange resin, but less than its binding affinity for calcium ions. One exemplary metal ion is $Mg^{2+}$.

Typically, prior to the contacting of the anion exchange resin and the AnxA5 product, the anion exchange resin is equilibrated. Any suitable equilibration may be used. For example, the anion exchange resin may be equilibrated with a buffer (e.g. 20 mM Tris pH 7.4), a non-ionic detergent (e.g. 0.1% polysorbate, preferably Tween80) and salt (e.g. 25 mM NaCl). Any suitable equilibration volume may be used; without limitation, the applicant has found 3 column volumes (CV) to be a suitable volume in the exemplified embodiment.

Preferably, the first anion exchange capture step is run in the positive mode with respect to the AnxA5 protein, and so the AnxA5 protein is temporarily bound to the anion exchanger during the anion exchange step, typically a wash solution is passed over the column to remove impurities from the bound AnxA5 protein, and then the first anion exchange product which comprises the released AnxA5 protein is produced by applying an elution buffer to the anion exchange resin to release the bound AnxA5 protein.

Strong anion exchange resins are preferred, as the applicant has found that these provided acceptable capacities for AnxA5 protein capture, whereas the performance with weak anion exchange resins was less acceptable. Strong anion exchange resins are well known in the art, and examples include resins with a Quarternary Ammonium functional group, such as a Type I resin having trialkyl ammonium chloride or hydroxide, or Type II resins having dialkyl 2-hydroxyethyl ammonium chloride or hydroxide (e.g. Q Sepharose XL by GE Healthcare, Capto Q by GE Healthcare, Unosphere Q by Biorad, or Eshmuno Q by Merck). Weak anion exchange resins are not preferred, and examples include DEAE resin with a Diethylaminoethyl functional group. The Q Sepharose XL resin (e.g. as provided by GE Healthcare) may be most preferred.

After loading onto the anion exchange resin, under the positive mode, the AnxA5 protein temporarily binds to the resin, and can be washed to reduce/remove impurities. Any suitable wash conditions can be employed. For example, the wash solution may comprise, consist essentially of, or consist of an aqueous solution of a buffer (e.g. 20 mM Tris pH 7.4), a non-ionic detergent (e.g. 0.1% polysorbate, preferably Tween80) and salt (e.g. 25 mM NaCl). Any suitable wash volume may be used; without limitation, the applicant has found 10 column volumes (CV) to be a suitable volume in the exemplified embodiment.

The bound AnxA5 protein is then released from the anion exchange resin using an elution buffer. Any suitable elution buffer can be employed. For example, the elution buffer may comprise, consist essentially of, or consist of an aqueous solution of a buffer (e.g. 20 mM Tris pH 7.4), a non-ionic detergent (e.g. 0.01 to 1% (w/v) more preferably 0.1% (w/v) polysorbate, preferably Tween80) and salt at a concentration higher than the wash solution (e.g. 300 mM NaCl, optionally ±100, 90, 80, 70, 60, 50, 40, 30, 20, 10, or 5 mM). Any suitable elution volume may be used; without limitation, the applicant has found 9 column volumes (CV) to be a suitable volume for elution in the exemplified embodiment.

Accordingly, the AnxA5 protein is captured in the elution buffer, and this provides the first anion exchange product.

The anion exchange resin may then be regenerated and cleaned. Suitable methods for the regeneration and cleaning are known in the art, and one such suitable protocol is discussed in the examples.

Typically the first anion exchange product which comprises the released AnxA5 protein contains substantially in excess of 50% of the AnxA5 protein that was released from the host cells. Preferably, the first anion exchange product comprises more than 60%, 70% or 80% of the AnxA5 protein that was from the host cells. By point of comparison with the process of Marder et al. (supra), it is apparent that the prior art processes demonstrated large product losses of approximately 50% or more. For example, the process of Marder et al. (supra) involves an initial purification centrifugation step which discards the supernatant and collects the Annexin A5 bound to the pellet. Relative amounts of Annexin A5 in the discarded supernatant and as recovered from the pellet are shown in FIG. 3, lanes 2 and 3, respectively, of Marder et al (supra). From that figure it is apparent that about half of the released Annexin A5 is discarded in the process of Marder et al. (supra), leading to a low yield method.

As a further point of comparison, the applicant has found that the yield of the exemplified process provides a yield of about 5 g AnxA5 protein per litre of culture at the end of the first anion exchange chromatography capture step, which is much higher than the yield reported in Marder et al. (supra). (see "Conclusions", second paragraph) of 0.983 g of purified Annexin A5 protein per litre of culture.

Accordingly, in accordance with the first aspect of the present invention, it is preferred that the first anion exchange product comprises more than 1 g, more than 2 g, more than 3 g, more than 4 g, or about 5 g of AnxA5 protein per litre of culture.

Optionally, the first anion exchange product is subjected, directly or indirectly to a filtration step (such as a sterile filtration step). For example, without limitation, a 0.45 to 0.2 µM filtration step has been found to be suitable.

F. Affinity Chromatography

The applicant has also discovered (e.g. see Example 2, below), that contrary to conventional methods in which the successive addition of purification steps tends to lead to an ever increasing loss of yield (as product is lost at each step), that the combination of an anion exchange step and a heparin affinity chromatography step has a surprising benefit of attaining the high purity achieved by the heparin affinity chromatography step alone, but with substantially increased yield (i.e. the recovery is increased from about 30-40% to about 70-90%). The large increase in yield associated with the addition of a purification step is the direct opposite of what would normally be expected from the combination of purification steps.

Accordingly, a second aspect the present invention provides a process for the recovery and/or purification of a protein comprising the sequence of Annexin A5 (AnxA5), from a solution comprising the AnxA5 protein and one or more impurities (which may, or may not, be a product of a clarification step as described above), the method comprising subjecting the solution comprising the AnxA5 protein and one or more impurities (which solution may, or may not, be the direct or indirect product of a cell homogenisation, clarification and/or first anion exchange chromatography capture step, as discussed above) to an anion exchange resin in order to perform a first anion exchange step, and thereby produce a first anion exchange product which comprises the AnxA5 protein; and subjecting the first anion exchange product, directly or indirectly, to an affinity chromatography step, thereby to produce a first affinity chromatography product which comprises the released AnxA5 protein.

Preferably, in accordance with the process of the second aspect of the present invention, the affinity chromatography step may comprise the binding of the AnxA5 protein to immobilised heparin, and optionally wherein the binding is promoted by the presence of calcium ions and further optionally, the AnxA5 protein is eluted from the immobilised heparin using an elution buffer containing a calcium ion chelator, such as EDTA.

Additionally, as discussed in Example 3, the applicant has discovered that Tween80 has a particularly advantageous effect (compared to other non-ionic detergents, including other Tweens, such as Tween20) on a heparin affinity chromatography step. The inclusion of Tween 80, for example at around 0.1% (w/v) in the buffers used in the heparin affinity chromatography step can assist in eluting the AnxA5 protein in a single peak, reduce pressure, and prevent precipitation.

Accordingly, a third aspect the present invention provides a process for the recovery and/or purification of a protein comprising the sequence of Annexin A5 (AnxA5), from a solution comprising the AnxA5 protein and one or more impurities, the method comprising subjecting the solution comprising the AnxA5 protein and one or more impurities (which solution may, or may not, be the direct or indirect product of a cell homogenisation, clarification and/or first anion exchange chromatography capture step, as discussed above) to a heparin affinity chromatography step in the presence of Tween80 (preferably in the presence of 0.1% Tween80), thereby to produce a first affinity chromatography product which comprises the released AnxA5 protein.

Thus, both of the second and third aspects of the present invention, which can be operated either independently of each other or in combination (i.e. the heparin affinity chromatography step in the second aspect of the present invention can include Tween 80 (for example at around 0.1% (w/v)) in the buffers used in the heparin affinity chromatography step, More generally, however, the first aspect of the present invention may comprise the step of subjecting the released AnxA5 protein to an affinity chromatography step, thereby to produce a first affinity chromatography product which comprises the released AnxA5 protein. It may be particularly preferred that the AnxA5 protein in the first anion exchange product, for example as produced by a method as described above, may be subjected directly or indirectly (e.g. after sterile filtration and/or the addition of further components) to the affinity chromatography step.

Accordingly, in one embodiment of the first aspect of the present invention (which may be combined with either or both of the features of the second and third aspects of the present invention), the process comprises steps wherein:
(a) a biomass homogenate comprising the released AnxA5 protein as described above is clarified by a clarification process as described above, and thereby produces a clarified product comprising the released AnxA5 protein, and
(b) the AnxA5 protein in the clarified product is subjected to an anion exchange resin in order to perform a first anion exchange step as described above, and thereby produce a first anion exchange product which comprises the AnxA5 protein, and
(c) wherein the AnxA5 protein in the first anion exchange product is subjected (directly or indirectly) to an affinity chromatography step.

Preferably, the affinity chromatography step comprises the binding of the AnxA5 protein to immobilised heparin, and optionally the binding is promoted by the presence of calcium ions.

Accordingly, prior to the heparin affinity step, the AnxA5 product may be conditioned by the addition of any one or more of calcium ions (e.g. $CaCl_2$)), non-ionic detergent (preferably Tween80), and optionally buffered (e.g. Tris buffer at pH 7.4). Without limitation, the applicant has demonstrated a beneficial effect when the filtered anion exchange product is diluted about 8-fold with a dilution buffer containing 20 mM Tris, pH 7.4, 0.1% Tween80 and 2 mM $CaCl_2$).

It may, therefore, be preferred that the AnxA5 product is conditioned with polysorbate 80, and more preferably wherein the polysorbate 80 is at a final concentration of greater than about 0.01% to up to about 10% (w/v), such as about 0.05%, 0.06%, 0.07%, 0.08%, 0.09%. 0.10%, 0.11%, 0.12%, 0.13%, 0.14%, 0.15%, 0.16%, 0.17%, 0.18%, 0.19%, 0.2%, 0.3%, 0.4%, 0.5%, 0.6%, 0.7%, 0.8%, 0.9%, 1%, 2%, 3%, 4%, 5%, 6%, 7%, 8%, 9% or 10%. The term "about" in this context refers to ±50%, 40%, 30%, 20%, 10%, or 5% of the stated value.

The dilution with calcium allows Annexin A5 to bind to the immobilized Heparin chromatography. This interaction is, by comparison with an ionic interaction, slow. The contact time is important, and therefore the chromatography is preferably performed with 100 cm/h.

The conditions used in the loading of the affinity chromatography column (e.g. the heparin affinity chromatography column) permit binding of the AnxA5 protein to the heparin. That is, the affinity chromatography is typically run in the positive mode with respect to the AnxA5 protein.

The affinity chromatography column (e.g. the heparin affinity chromatography column) can be loaded with the desired level of AnxA5 product. For example, the loading may be conducted at about, or greater than, 5 g per litre of column resin volume, such as about 10 g/L, about 15 g/L, about 20 g/L, about 25 g/L, about 30 g/L or more. The term "about" in this context refers to ±50%, 40%, 30%, 20%, 10%, or 5% of the stated value. In practice, the applicant has found that loading at about 20 to 30 g of AnxA5 product per litre of column resin volume provides highly satisfactory results in terms of process efficiency and product purification and recovery. In the context of such high loadings, the applicant has found that the presence of polysorbate 80 in the mixture to be loaded is particularly beneficial in avoiding AnxA5 protein precipitation or insolubility.

In the absence of the use of polysorbate 80, precipitation and an increase in back pressure is observed, and the affinity chromatography step becomes less efficient. Please see Examples 3 and 4.

After loading of the AnxA5 protein, the column is typically washed one or more times to remove impurities. Any suitable washing protocol may be used. The applicant had found, without limitation, that a suitable washing protocol includes a two stage wash. For example, in a first stage of washing, a wash may be performed using a first wash buffer containing calcium (e.g. 20 mM Tris pH 7.4; 0.1% Tween80; 2 mM $CaCl_2$)). The volume of first stage washing may be varied dependent in the desired result and the exact nature of the wash solution used. Without limitation, the applicant has found, for example, that the exemplary wash buffer noted above can be successfully used with 15 CV of washing. In a second stage wash, the wash buffer may contain calcium in an amount that is lower than the first wash, or preferably no calcium (e.g. 20 mM Tris pH 7.4; 0.1% Tween80). The volume of second stage washing may be varied dependent in the desired result and the exact nature of the second stage wash solution used. Without limitation, the applicant has found, for example, that the exemplary second stage wash buffer noted above can be successfully used with 2 CV of washing.

Thereafter, the AnxA5 protein is eluted from the affinity chromatography column using an elution buffer, and thereby providing the first affinity chromatography product which comprises the released AnxA5 protein. In the case of using a heparin affinity chromatography column, it may be preferred to use an elution buffer comprising a calcium metal ion chelator, such as EDTA or EGTA.

For example, without limitation, the applicant has found that a suitable elution buffer is 20 mM Tris pH 7.4; 0.1% Tween80; 10 mM EDTA; 25 mM NaCl, which chelates the calcium ions. The chelation reaction specifically elutes Annexin A5 which can only bind to Heparin in the presence of calcium.

It may be preferred to reduce the flow rate to less than 100 cm/h during elution to increase the concentration of the product. For example, without limitation, in the examples, the applicant allowed a concentrated elution by reducing the flow rate to 60 cm/h in the elution. The complete elution peak may, for example, be collected starting from the rising of the UV signal at 0.05 AU to 0.05 AU in the descending peak representing approximately 7 CV. Preferably, the elution profile demonstrates a single peak, which is most ideally a sharp peak.

Accordingly, the first affinity chromatography product comprises the released AnxA5 protein and the calcium ion chelator, such as EDTA or EGTA, optionally wherein the calcium ion chelator is present in the range of from about 0.1 mM to 500 mM, such as from about 1 mM to about 100 mM, more typically in the range of from about 2 mM to about 50 mM, more preferably in the range of about 5 mM to about 15 mM, and most preferably about 10 mM. The term "about" in that context can include the meaning of ±50%, 40%, 30%, 20%, 10%, 5% or 1% of the stated concentration (s).

The affinity chromatography step may be the most powerful purification step in the process scheme. The AnxA5 protein binds to calcium ions and, in this calcium bound state the product can form a highly specific bond with Heparin. Typically, only correctly folded AnxA5 protein forms that have the ability to complex with calcium can bind to Heparin. Thereby the affinity chromatographic step may be useful to assist in discriminating between correctly folded and misfolded product. Additionally the intermediate step reaches high depletion factors as the highly specific interaction is combined with a specific elution mode by the chelate reaction of calcium with EDTA. Therefore a strong reduction of endotoxin and HCP is observed combined with a moderate reduction of the DNA content. Endotoxin, typically already having been reduced (preferably by about 97%) during the preceding anion exchange capture step, is further reduced (preferably by about 99%), and this preferably takes the endotoxin levels to about 0.03% of the levels in the clarified product prior to the first anion exchange capture step.

G. Anion Exchange Polishing

In a further embodiment of the first, second and/or third aspects of the present invention, an AnxA5 product (for example, as produced by the affinity chromatography step) may, directly or indirectly, be further purified by an anion exchange polishing step.

In the case that the an AnxA5 product as produced by the affinity chromatography step is indirectly further purified by an anion exchange polishing step, then the steps of affinity chromatography and the anion exchange polishing step may be separated by the addition of one or more conditioning additives to the product of the affinity chromatography step.

Suitable additives can include, for example, diluent (e.g. water) to further dilute the AnxA5 protein in the product of the affinity chromatography product; buffer (e.g. Tris, for example at 35 mM and pH 8); non-ionic detergent (e.g. polysorbate, more preferably Tween80, such as at a concentration of about 0.1% w/v); and/or one or more further additives based on the fourth aspect of the present invention, as discussed below.

That is, to say, a fourth aspect of the present invention is based on the applicant's realisation that calcium metal ion chelators (e.g. EDTA) can impact negatively on the efficacy of anion exchange steps. Free EDTA (or other chelator) can bind directly to the anion exchange function groups, and thereby reduce the capacity and also the separation achieved by an anion exchange step.

This is a particular issue in the case of performing an anion exchange on the product of a heparin affinity chromatography step, in which the AnxA5 protein is bound to heparin in the presence of calcium ions, and then a calcium metal ion chelator (e.g. EDTA) is used to elute the bound AnxA5 protein. As a consequence the eluted AnxA5 product of the heparin affinity chromatography step contains high levels of calcium ion chelator. It is generally desirable to be able to further purify the AnxA5 product with a further anion exchange step, but the calcium ion chelator is a problematic component during that further anion exchange step. On the other hand, it is time consuming and therefore also increases costs, to attempt to remove calcium metal ion chelator before an anion exchange step. Therefore, prior art methods involving, for example, dialysis steps for buffer replacement are slow and inefficient, and so increase production costs. Further, the inclusion of the calcium metal ion chelator in the AnxA5 product during the anion exchange step can be an important component to prevent calcium-mediated binding of the AnxA5 protein to impurities, including endotoxin. It would therefore be convenient and efficacious to introduce an additive that blocks or reduces the binding of the calcium ion chelator to the anion exchange resin, yet which would allow the anion exchange step to be performed without inconvenience and cost associated with dialysis, and without preventing the beneficial effect of the calcium metal ion chelator during the anion exchange step.

The applicant has realised that this can be achieved by the inclusion in the AnxA5 protein product, prior to anion exchange, or one or more types of additional selected metal ions, wherein the additional selected metal ions are selected such that the calcium metal ion chelator has a binding affinity for the selected metal ions that is greater than its binding affinity for the anion exchange resin, but less than its binding affinity for calcium ions. The selection of the appropriate additional metal ions will depend on the nature of the calcium ion chelator and the nature of the anion exchange resin. For example, in the case of using EDTA as a calcium ion chelator, $Mg^{2+}$ ions are generally suitable to achieve the object of the present invention, and can be added to the AnxA5 protein product prior to an anion exchange step.

Accordingly, a fourth aspect of the present invention provides a process for the recovery and/or purification of a protein comprising the sequence of Annexin A5 (AnxA5) from a composition that comprises the AnxA5 protein and a calcium metal ion chelator, characterised in that the process comprises subjecting the composition to an anion exchange resin in order to perform an anion exchange step and thereby recover and/or purify the AnxA5 protein from the composition, and further characterised in that the anion exchange step is conducted in the presence of additional selected metal ions, wherein the additional selected metal ions are selected such that the calcium metal ion chelator has a binding affinity for the selected metal ions that is greater than its binding affinity for the anion exchange resin, but less than its binding affinity for calcium ions.

Preferably, the additional selected metal ions are mixed with the composition that comprises the AnxA5 protein and a calcium metal ion chelator prior to being subjected to the composition to an anion exchange resin. Solutions used in subsequent anion exchange steps (e.g. wash solutions and/or elution buffers) may or may not also include the additional selected metal ions. Therefore, in one embodiment of this aspect of the invention, the step of conducting the anion exchange step in the presence of additional selected metal ions refers to the addition of the additional selected metal ions to the composition that comprises the AnxA5 protein and a calcium metal ion chelator prior to being subjected to the composition to an anion exchange resin.

In one embodiment of the fourth aspect of the present invention, the calcium metal ion chelator is selected from EDTA or salt thereof, EGTA or salt thereof, and most preferably EDTA.

The calcium metal ion chelator may be present in the composition in an excess and/or at a concentration in the range of from about 0.1 mM to 500 mM, such as from about 1 mM to about 100 mM, more typically in the range of from about 2 mM to about 50 mM, for example at a concentration of about, or at least, 0.1 mM, 0.5 mM, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM or more. In that context, the term "about" can include the meaning of ±0.5, 0.4, 0.3, 0.2, or 0.1 mM of the stated value. In the foregoing context, the term "excess" can include the meaning that sufficient amount calcium metal ion chelator is present to remove any divalent ion that may contribute to the binding of the AnxA5 protein to an immobilized heparin on the column in a preceding affinity chromatography step, thereby allowing the AnxA5 protein to be released from the column to the solution, and then used directly or indirectly in the anion exchange polishing step.

In one exemplary embodiment of the fourth aspect of the present invention, the selected metal ions are divalent cations, such as $Mg^{2+}$ ions.

It may be preferred that the selected metal ions are present during the anion exchange step in an amount effective to reduce (such as by about 50%, 60%, 70%, 80%, 90%, 95%, 98%, 99% or more) or prevent an interaction between the calcium ion chelator and the anion exchange resin during the process of subjecting the composition to the anion exchange resin. For example, the selected metal ions may be present during the anion exchange step in an amount effective to reduce or prevent an interaction between the calcium ion chelator and the anion exchange resin during loading of the composition onto the anion exchange resin and/or during one or more washing steps in which the AnxA5 protein is bound to the anion exchange resin and impurities are removed by washing.

It may be preferred that the selected metal ions are present during the anion exchange step in an amount effective to increase binding of the AnxA5 protein to the anion exchange resin in the presence of the calcium ion chelator, and thereby reduce (such as by about 5%, 10%, 15%, 20%, 25%, 30%, 35%, 40%, 45%, 50%, 60%, 70%, 80%, 90%, 95%, 98%, 99% or more) the loss of AnxA5 protein in the flow through of the anion exchange step, compared to the level of loss observed when no selected metal ions are present during the anion exchange step.

It may be preferred that the selected metal ions are present during the anion exchange step at a concentration of about 1 to about 100 mM, such as about 2 to about 50 mM, about 5 to about 25 mM, about 10 to about 15 mM or about 12.5 mM.

Further, it may be preferred that the calcium metal ion chelator is EDTA and the selected metal ions are $Mg^{2+}$ ions, and more preferably the molar ratio of $Mg^{2+}$ ions to EDTA is in the range of 0.5:1 to 2:1, most preferably at least 1:1 or >1:1.

In the context of the fourth aspect of the present invention, in a further embodiment, the composition that comprises the AnxA5 protein and a calcium metal ion chelator and which is subjected to the anion exchange resin may be the direct, or indirect, product of a preceding process that comprises the step of subjecting the AnxA5 protein to an affinity chromatography step and eluting the AnxA5 protein with a calcium ion chelator, thereby producing an affinity chromatography product which is a composition that comprises the AnxA5 protein and a calcium metal ion chelator. For example, the preceding affinity chromatography step may comprises the binding of the AnxA5 protein to immobilised heparin, optionally wherein the binding is promoted by the presence of calcium ions, and further optionally wherein the AnxA5 protein is eluted from the immobilised heparin using an elution buffer containing a calcium ion chelator, such as EDTA.

It may be further preferred that there is no dialysis step between the preceding affinity chromatography step and the anion exchange step and/or there is no removal of calcium ion chelator from the product of preceding affinity chromatography step prior to the application of the direct or indirect product to the anion exchange step.

In the context of the fourth aspect of the present invention, in a further embodiment the selected metal ions are added to the composition prior to, or during, the anion exchange step.

In a preferred embodiment, the product of an affinity chromatography step according to any of the first, second or third aspects of the present invention is treated with a further anion exchange step, such as an anion exchange step in accordance with the fourth aspect of the present invention.

Optionally, prior to the (second) polishing anion exchange step, one or more parameters of the environment of the released AnxA5 protein, selected from the group consisting of the concentration of the AnxA5 protein, the pH, the conductivity, the level of calcium ion chelator and the level of non-ionic detergent, or the level of selected additional metal ions (in accordance with the fourth aspect of the present invention) is, or are, adjusted.

Typically, prior to the contacting of the (second) anion exchange resin of the polishing step, and the AnxA5 product, the anion exchange resin is equilibrated. Any suitable equilibration may be used. For example, the anion exchange resin may be equilibrated with a buffer (e.g. 20 mM Tris pH 7.4), a non-ionic detergent (e.g. 0.1% polysorbate, preferably Tween80) and salt (e.g. 25 mM NaCl). Any suitable equilibration volume may be used; without limitation, the applicant has found 3 column volumes (CV) to be a suitable volume in the exemplified embodiment.

Preferably, the (second) anion exchange polishing step is run in the positive mode with respect to the AnxA5 protein, and so the AnxA5 protein is temporarily bound to the anion exchanger during the anion exchange step, typically a wash solution is passed over the column to remove impurities from the bound AnxA5 protein, and then the second anion exchange product which comprises the released AnxA5 protein is produced by applying an elution buffer to the anion exchange resin to release the bound AnxA5 protein.

Strong anion exchange resins are preferred. Strong anion exchange resins are well known in the art, and examples include resins with a Quarternary Ammonium functional group, such as a Type I resin having trialkyl ammonium chloride or hydroxide, or Type II resins having dialkyl 2-hydroxyethyl ammonium chloride or hydroxide. Without limitation, one example of a suitable anion exchange resin for the second polishing step includes Source15 Q. A Source 15 Q anion exchange resin can be defined as a polymeric strong anion exchanger and may be further characterised by having a quaternary ammonium ligand, about a 15 μm median particle size of the cumulative volume distribution ($d_{50v}$), a polystyrene/divinylbenzene matrix, and/or a pressure/flow specification of about 400 cm/h, 1000 kPa, when assessed as a FineLine 100 column with a bed height 10 cm.

Without limitation, further example of a suitable anion exchange resin for the second polishing step includes Capto Q ImpRes. A Capto Q ImpRes can be defined as a strong anion exchanger and may be further characterised by having a quaternary amine ligand, a high-flow agarose matrix, about a 36-44 μm median particle size ($d_{50v}$), an ionic capacity of about 0.15-0.18 mmol $Cl^-$/ml medium, a binding capacity/ml of Chromatography Medium of >55 mg BSA and >48 mg β-lactoglobulin, and/or a pressure/flow specification of about 300 kPa at min. 220 cm/h, when assessed as a 1 m diameter column with a 20 cm bed height.

Without being bound by theory, the applicant has found that the use of the Capto Q ImpRes anion exchange resin for the (second) anion exchange polishing step can be particularly advantageous when the AnxA5 protein to be purified is derived from a recombinant source (such as *E. coli* BL21 (DE3) that is further engineered overexpress PGL, as described in Aon et al. (*Appl. Env. Microbiol.*, 2008, 74(4): 950-958; the contents of which are incorporated herein by reference) that causes no, or low levels of, gluconoylation of the AnxA5 protein that it expresses. "Low" in that context can include then meaning that the level of gluconoylation is less than (such as less than 90%, 80%, 70%, 60%, 50%, 40%, 30%, 20%, 10%, 9%, 8%, 7%, 6%, 5%, 4%, 3%, 2% or 1% of) the level of gluconoylation of an AnxA5 protein that is expressed in *E. coli* strain BL21 (DE3) (e.g. as is widely commercially-available, and as described in Marder et al., 2014, *BMC Biotechnology*, 14:33). For example, it maybe that the level of gluconoylated AnxA5 protein in the product that is applied to the Capto Q ImpRes anion exchange resin for the (second) anion exchange polishing step is within the range of 0.5 to 30%, or 0.5 to 20%, or 0.5 to 15%, or 0.5 to 10% of the total content of AnxA5 protein in the product that is applied. The guluconylated variants of Anx5 can, for example, be measured and quantified by using Ultra Performance Liquid Chromatography (UPLC) or High Performance liquid Chromatography (HPLC) chromatography instruments using appropriate anion exchange or reverse phase columns. Different peaks can be further identified and characterized by using mass spectroscopy (MS).

The applicant has found that the use of the Capto Q ImpRes anion exchange resin for the (second) anion exchange polishing step when the AnxA5 protein to be purified has no, or low levels of, gluconoylation, results in an even more efficient process (compared, say to the use of Source 15 Q anion exchange resin for the (second) anion exchange polishing step), as the Capto Q ImpRes anion exchange resin has a high binding capacity, tolerates high flowrates without back pressure, can be packed at a higher bed height and has a lower price. The quality and purity of the final product is maintained irrespective of whether Source 15 Q or Capto Q ImpRes anion exchange resin is used. However, it is estimated that the switch from Source 15 Q anion exchange resin (with 15 μm particle size) to the Capto Q ImpRes anion exchange resin (with 40 μm particle diameter) provides a productivity increase that can be more than about five times (5×) by reducing the time needed to operate the whole process (in particularly since the second anion exchange step used for polishing is one of the most time-consuming steps), and may be able to reduce overall manufacturing cost by more than about 50%. The avoidance of resin with very small bead size (<30 μm) allows high flowrates and allows the chromatography column to be packed at higher resin bed-height without causing unacceptable backpressure. This increases the productivity as for a given footprint (column diameter) more resin can be packed in the column and therefore more protein can be bound, and at the same time allows faster operation due to higher flowrates.

After loading onto the (second) anion exchange resin for polishing, under the positive mode, the AnxA5 protein temporarily binds to the resin, and can be washed to reduce/remove impurities. Any suitable wash conditions can be employed. For example, the wash solution may comprise, consist essentially of, or consist of an aqueous solution of a buffer (e.g. 20 mM Bis-Tris, pH 7), and salt (e.g. 25 mM NaCl), and optionally a non-ionic buffer (e.g. a polysorbate, preferably Tween80, such as at a level of about 0.1 w/v). Any suitable wash volume may be used; without limitation, the applicant has found 3 column volumes (CV) to be a suitable volume in the exemplified embodiment.

The bound AnxA5 protein is then released from the anion exchange resin using an elution buffer. Any suitable elution buffer can be employed. For example, the elution buffer may comprise, consist essentially of, or consist of an aqueous solution of a buffer (e.g. 20 mM Bis-Tris, pH 7), salt at a concentration higher than the wash solution (e.g. 180 mM NaCl, optionally ±100, 90, 80, 70, 60, 50, 40, 30, 20, 10, or 5 mM) and optionally a non-ionic buffer (e.g. a polysorbate, preferably Tween80, such as at a level of about 0.1 w/v). Any suitable elution volume may be used; without limitation, the applicant has found 33 column volumes (CV), increasing the concentration of the elution buffer from 0 to 100% in a linear gradient, to be a suitable for elution in the exemplified embodiment.

Accordingly, the AnxA5 protein is released into in the elution buffer, and this provides the (second) polished anion exchange product. As discussed in Example 1, a process conducted with 0.1% Tween80 increased the product yield post intermediate by approximately 30%.

The (second) anion exchange resin may then be regenerated and cleaned. Suitable methods for the regeneration and cleaning are known in the art, and one such suitable protocol is discussed in the examples.

The polishing step is mainly implemented for the reduction of product related impurities e.g. the separation of different Annexin A5 isoforms. Additionally the polishing step reaches the highest depletion factor in the process for the residual DNA and strongly reduces HCP. Endotoxin, being already at a low level after the intermediate step, is further reduced by about 99%, which (when used in combination with the preceding cell homogenisation, nuclease treatment, clarification, capture anion exchange, filtration (such as a sterile filtration step), and heparin affinity steps) takes the endotoxin levels to about 0.0003% of the levels in the clarified product prior to the first AX step.

Accordingly, in a further embodiment of the first, second, third and/or fourth aspects of the present invention, there is provided a process for the recovery and/or purification of a recombinantly expressed intracellular protein comprising the sequence of Annexin A5 (AnxA5) from a host cell with a cell wall, or a culture in accordance with the first aspect of the present invention and preferably wherein the process comprises recovery and/or purification of a recombinantly expressed intracellular AnxA5 protein from a culture of the host cells, and wherein the culture has a volume of at least about 100 L, about 200 L, about 300 L, about 400 L, about 500 L, about 600 L, about 700 L, about 800 L, about 900 L, about 1,000 L, about 2,000 L, about 3,000 L, about 4,000 L, about 5,000 L, about 6,000 L, about 7,0000 L, about 8,0000 L, about 9,0000 L, about 10,000 L, about 20,000 L, about 30,000 L, about 40,000 L, about 50,000 L, about 60,000 L, about 70,0000 L, about 80,0000 L, about 90,0000 L, about 100,000 L or higher, wherein:

(a) the process comprises releasing the intracellular protein from the host cell in the presence of a homogenisation buffer comprising non-ionic detergent in accordance with the first aspect of the present invention;

(b) optionally wherein the releasing step is in accordance with any one or more of the embodiments of the first aspect of the present invention as described above in subsection C;

(c) further optionally wherein the process comprises a step of clarifying the biomass homogenate according to any one or more of the embodiments of as described above in subsection D; and (d) wherein the process further comprises the step of subjecting the released AnxA5 protein directly or indirectly to an anion exchange resin in order to perform a first anion exchange step, and thereby produce a first anion exchange product which comprises the released AnxA5 protein in accordance with any of any one or more of the embodiments as described above in subsection E; and (e) wherein the process further comprises the step of subjecting the released AnxA5 protein directly or indirectly to an affinity chromatography step, in accordance with any of the first, second and/or third aspects of the present invention as described above in section F, and (f) wherein the product of the affinity chromatography step is a composition that comprises the AnxA5 protein and a calcium metal ion chelator; and (g) wherein the direct, or indirect, product of the affinity chromatography step that comprises the AnxA5 protein and the calcium metal ion chelator is subjected to anion exchange step in accordance with any of the embodiments described above in this section (i.e. section G).

H. Product Formulation

The process of any of the first, second, third or fourth aspects of the present invention may further comprise, preferably at the end of the process, one or more further steps selected from the group consisting of concentration, buffer change, conditioning and filtration (such as a sterile filtration step), and optionally a final step of storing the AnxA5 protein-containing product in a sterile container.

For example, one of the further steps used for product formulation may be ultrafiltration/diafiltration (UF/DF), optionally wherein the product of the UF/DF step contains the AnxA5 protein at a concentration of at least about 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 25 mg/mL, 30 mg/mL, 35 mg/mL, 40 mg/mL, 45 mg/mL, 50 mg/mL, 60 mg/mL, 70 mg/mL, 80 mg/mL, 90 mg/mL, 100 mg/mL, 125 mg/mL or greater.

In another example, one of the further steps used for product formulation may be the addition of a non-ionic surfactant, preferably a polysorbate, and more preferably Tween80. The non-ionic surfactant may be added in an amount desired for the final product, such as to a final concentration of about 0.05% (w/w) (e.g. ±0.05, 0.04, 0.03, 0.02 or 0.01% w/v).

In another example, one of the further steps used for product formulation may be a filtration step (such as a sterile filtration step), for example using a 0.45-0.2 μm filter or a 0.22 μm filter.

As indicated above, the process of the first, second, third or fourth aspects of the present invention may conclude with the step of sterile filtration, and placing the sterile filtered AnxA5 protein-containing product in a sterile container.

The final concentration of the AnxA5 protein in the filled container may be adjusted as required. Without limitation, the applicant has exemplified a final concentration of 10 mg/mL. A suitable concentration may, for example, be 1-125 mg/mL, 2-100 mg/mL, 5-50 mg/mL, 7-30 mg/mL or about 10-20 mg/mL.

Optionally, the processes of the present invention may provide a final sterile AnxA5 protein product in a non-phosphate buffer (such as Bis-Tris or Tris buffer) at about pH 7.4 (e.g. ±0.5, 0.4, 0.3, 0.2, or 0.1 pH units), comprising about 150 mM NaCl (e.g. ±50, 40, 30, 20 or 10 mM), about 1 mM $CaCl_2$) (e.g. ±500, 400, 300, 200, 100, or 50 μM), about 0.05% (w/w) (e.g. ±0.05, 0.04, 0.03, 0.02 or 0.01% w/v) polysorbate, such as Tween80 or other non-ionic detergent. A pH of about 7.4 is a typical target pH for formulations intended for use with humans (especially for intravenous delivery), as it matches the pH in human blood and provides a stable AnxA5 protein with good solubility. Below pH 7, and particularly down to around pH 6, the AnxA5 protein loses solubility and can start to precipitate.

NaCl can be useful to maintain the AnxA5 product in a monomeric form during storage. Accordingly, the processes of the present invention may provide a final sterile AnxA5 protein product, wherein the NaCl concentration present maintains AnxA5 protein in a form that is predominantly (that is, greater than about 50%, such as 60%, 70%, 80%, 85%, 90%, 95%, 96%, 97%, 98%, 99% or substantially 100%) monomeric. Percentage monomer levels can be readily determined using techniques well known in the art, such as gel permeation chromatography (GPC).

In one embodiment, the processes of the present invention provide a final sterile, therapeutically acceptable AnxA5 protein product with an overall yield of greater than 1 g of AnxA5 protein per L of host cell culture, more preferably at least about 1.5 g/L, even more preferably in the range of about 2 to about 4 g/L. In that context, the term "about" may include ±0.4, 0.3, 0.2 or 0.1 g/L of the stated value.

In another embodiment, the processes of the present invention provide a final sterile, therapeutically acceptable AnxA5 protein product with an overall recovery of AnxA5 protein of at least about 24% by weight (e.g. ±10, 9, 8, 7, 6, 5, 4, 3, 2, 1%), or more, of the AnxA5 protein present in the from the host cell culture. This can be determined, for example, by measuring soluble AnxA5 protein in the initial homogenate (which can be captured and measured by centrifugation of an aliquot of the homogenate and testing the level of AnxA5 in the supernatant) and in the final purified product.

Additionally, at any point in the process (if relevant, prior to filling the sterile container), and typically after the final purification step as described above, the AnxA5 protein may be chemically modified. For example, the AnxA5 protein may be PEGylated. PEGylated Annexin A5 is disclosed in WO 02/067857. PEGylation is a method well known to those skilled in the art wherein a polypeptide or peptidomimetic compound (for the purposes of the present invention, the AnxA5 protein) is modified such that one or more polyethylene glycol (PEG) molecules are covalently attached to the side chain of one or more amino acids or derivatives thereof. It is one of the most important molecule altering structural chemistry techniques (MASC). Other MASC techniques may be used; such techniques may improve the pharmacodynamic properties of the molecule, for example extending its half-life in vivo. A PEG-protein conjugate is formed by first activating the PEG moiety so that it will react with, and couple to, the protein or peptidomimetic compound of the invention. PEG moieties vary considerably in molecular weight and conformation, with the early moieties (monofunctional PEGs; mPEGs) being linear with molecular weights of 12 kDa or less, and later moieties being of increased molecular weights. PEG2, a recent innovation in PEG technology, involves the coupling of a 30 kDa (or less) mPEG to a lysine amino acid (although PEGylation can be extended to the addition of PEG to other amino acids) that is further reacted to form a branched structure that behaves like a linear mPEG of much greater molecular weight (Kozlowski et al., 2001). Methods that may be used to covalently attach the PEG molecules to polypeptides are further described in Roberts et al. (2002) *Adv Drug Deliv Rev*, 54, 459-476; Bhadra et al. (2002) *Pharmazie* 57, 5-29; Kozlowski et al. (2001) *J Control Release* 72, 217-224; and Veronese (2001) *Biomaterials* 22, 405-417 and references referred to therein. The advantages of PEGylation include reduced renal clearance which, for some products, results in a more sustained adsorption after administration as well as restricted distribution, possibly leading to a more constant and sustained plasma concentrations and hence an increase in clinical effectiveness (Harris et al. (2001) *Clin Pharmacokinet* 40, 539-551). Further advantages can include reduced immunogenicity of the therapeutic compound (Reddy (2001) *Ann Pharmacother*, 34, 915-923), and lower toxicity (Kozlowski et al. (2001), Biodrugs 15, 419-429). In the event that the AnxA5 protein is chemically modified, it may be suitable to perform one or more additional purification steps, such as to reduce or remove unreacted components and/or to select a homogenous population of chemically modified AnxA5 protein for inclusion into the final product. Suitable technique for the purification of chemically-modified proteins from the reaction process are known to those skilled in the art.

The final product may be, or may be subsequent formulated to form, a pharmaceutical or veterinary composition.

The final product may be presented in a unit dosage form. For example, a unit dosage form may contain about 1, 2, 3, 4, 5, 6, 7, 8, 9, 10 mg of the AnxA5 protein (wherein the term "about" refers to ±0.5, 0.4, 0.3, 0.2 or 0.1 mg) or more, e.g. within the range of 0.1 to 1000 mg, or 1 to 100 mg.

A pharmaceutical or veterinary composition may comprise the AnxA5 protein in admixture with a pharmaceutically or veterinarily acceptable adjuvant, diluent or carrier, which will typically be selected with regard to the intended route of administration and standard pharmaceutical practice. The composition may be in the form of immediate-, delayed- or controlled-release applications. Preferably, the formulation is a unit dosage containing a daily dose or unit, daily sub-dose or an appropriate fraction thereof, of the active ingredient.

The phrases "pharmaceutical or veterinary acceptable" include reference to compositions that do not produce an adverse, allergic or other untoward reaction when administered to an animal or a human, as appropriate. The preparation of such pharmaceutical or veterinary compositions are known to those of skill in the art in light of the present disclosure, as exemplified by Remington's Pharmaceutical Sciences, 18th Ed. Mack Printing Company, 1990, incorporated herein by reference. Moreover, for animal or human administration, it will be understood that preparations should meet sterility, pyrogenicity, general safety and purity standards as required by FDA Office of Biological Standards.

As used herein, "pharmaceutically or veterinarily acceptable carrier" includes any and all solvents, dispersion media, coatings, surfactants, antioxidants, preservatives (e.g., antibacterial agents, antifungal agents), isotonic agents, salts, preservatives, drugs, drug stabilizers, excipients, disintegration agents, such like materials and combinations thereof, as would be known to one of ordinary skill in the art. Except insofar as any conventional carrier is incompatible with the active ingredient, its use in the therapeutic or pharmaceutical compositions is contemplated.

The pharmaceutical or veterinary compositions according to the invention may, or may not, be intended for, and, thus formulated in a manner suitable for, parenteral, intravenous, intra-arterial, intraperitoneal, intra-muscular, intra-ocular, intra-cranial, intra-cerebrally, intra-osseously, intra-cerebroventricularly, intra-thecally or subcutaneous administration, by administration from a drug-eluting stent, for administered by infusion techniques, or for topical administration (such as in a form suitable for epicutaneous e.g. as a cream or ointment, inhalation, ophthalmic/eye drops, otic/ear drops, or through mucous membranes in the body). Sterile injectable solutions may be prepared by incorporating the active compounds in the required amount in the appropriate solvent with various of the other ingredients enumerated above, as required, followed by sterilization. The pharmaceutical compositions may be best used in the form of a sterile aqueous solution which may contain other substances, for example, enough salts or glucose to make the solution isotonic with blood. The aqueous solutions may be suitably buffered (preferably to a pH of from 3 to 9), if necessary. The preparation of suitable pharmaceutical formulations under sterile conditions is readily accomplished by standard pharmaceutical techniques well-known to those skilled in the art.

The pharmaceutical or veterinary compositions according to the invention may alternatively be formulated in the form of a powder, such as a sterile powder, which may be a lyophilised powder.

A therapeutically effective amount of an AnxA5 protein for administration to a patient, such as a human patient, on the basis of a daily dosage level may be from 0.01 to 1000 mg of AnxA5 protein per adult (for example, from about 0.001 to 20 mg per kg of the patient's body weight, such as 0.01 to 10 mg/kg, for example greater than 0.1 mg/kg and up to or less than 20, 10, 5, 4, 3 or 2 mg/kg, such as about 1 mg/kg), administered in single or divided doses.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

For veterinary use, a compound of the invention is administered as a suitably acceptable formulation in accordance with normal veterinary practice and the veterinary surgeon will determine the dosing regimen and route of administration which will be most appropriate for a particular animal.

I. Product Characteristics

The processes of the present invention provide an AnxA5 product as defined above. As such, the product produced by the claimed process is also a further, fifth, aspect of the present invention.

In a further embodiment, the process of any of the aspects of the present invention may provide a product comprising the AnxA5 protein with a purity suitable for injectable pharmaceutical for use in humans. The process described herein typically removes process related impurities to well below acceptable levels like host cell protein below 20 ng per mg of AnxA5 protein, DNA below 10 pg per mg of AnxA5 protein, and Endotoxins below 1 EU per mg of AnxA5 protein.

In a further embodiment, the process of any of the aspects of the present invention may provide a product comprising non-AnxA5 protein, in particular host cell protein (other than the recombinantly expressed AnxA5 protein), at a level less than less than 100, 90, 80, 70, 60, 50, 40, 30, 20, 10, 5 ng or less per mg of AnxA5 protein. The FDA and EMA expect host cell protein less than 100 ng/mg and the applicant has demonstrated a host cell protein less than 20 ng/mg. The host cell protein content can, for example, be measured by using anti-host cell protein antibodies by ELISA sandwich techniques or other EMA and FDA accepted methods.

In a further embodiment, the process of any of the aspects of the present invention may provide a product comprising an endotoxin content of less than 100, 90, 80, 70, 60, 50 45, 40, 35, 30, 35, 20, 15, and preferably less than 10, 5 or 1 EU per mg AnxA5 protein, and/or preferably wherein the process provides a product in unit dosage form and the product contains less than 100, 90, 80, 70, 60, 50 45, 40, 35, 30, 35, 20, 15, and preferably less than 10, 5 or 1 EU per unit dose. The FDA and EMA expect endotoxins to be less than 100 EU/dose (the maximum permitted is 350 EU/dose); the expected amount translates to less than 10 EU/mg at 10 mg dose. Within these parameters, the unit dosage form may contain about 1, 2, 3, 4, 5, 6, 7, 8, 9, 10 mg of the AnxA5 protein or more (e.g. within the range of 0.1 to 1000 mg, or 1 to 100 mg). Endotoxins can, for example, be measured by using LAL base techniques or other EMA and FDA accepted methods.

In a further embodiment, the process of any of the aspects of the present invention may provide a product comprising nucleic acid (e.g. DNA) levels, such as host cell nucleic acid (e.g. DNA) levels, of less than 1,000 pg per mg of AnxA5 protein, preferably less than 500 pg per mg of AnxA5 protein, less than 400 pg per mg of AnxA5 protein, less than 300 pg per mg of AnxA5 protein, less than 200 pg per mg of AnxA5 protein, less than 100 pg per mg of AnxA5 protein, less than 50 pg per mg of AnxA5 protein, less than 40 pg per mg of AnxA5 protein, less than 30 pg per mg of AnxA5 protein, less than 20 pg per mg of AnxA5 protein, less than 15 pg per mg of AnxA5 protein, less than 10 pg per mg of AnxA5 protein, less than 9 pg per mg of AnxA5 protein, less than 8 pg per mg of AnxA5 protein, less than 7 pg per mg of AnxA5 protein, less than 6 pg per mg of AnxA5 protein, less than 5 pg per mg of AnxA5 protein, such as about 4 pg per mg of AnxA5 protein. DNA can, for example, be measured by using quantitative polymerase chain reaction (qPCR) techniques or other EMA and FDA accepted methods.

In a particularly preferred embodiment, the process of any of the aspects of the present invention may provide a product having any one or more characteristics selected from the listed consisting of:
 a concentration of AnxA5 protein typically around 8-12 g/L;
 host cell protein levels at or below 100 ng/mg and more preferably 20 ng/mg (as determined by ELISA);
 host cell DNA levels at or below 100 pg/mg; and more preferably 10 pg/mg
 Endotoxin at or below 35 EU/mg and more preferably 1 EU/mg,
 a purity of >95% as determined by size-exclusion chromatography;
 a bioburden of <1 cfu/mL (as determined by Ph. Eur. 2.6.12);
 a clear, colourless appearance free of visible particles; and wherein the main band detected by western blot analysis corresponds to the Annexin A5 reference.

A further particularly-preferred embodiment, the AnxA5 protein in the product may have a low level of gluconoylation. "Low" in that context can include then meaning that the level of gluconoylation is less than (such as less than 90%, 80%, 70%, 60%, 50%, 40%, 30%, 20%, 10%, 9%, 8%, 7%, 6%, 5%, 4%, 3%, 2% or 1% of) the level of gluconoylation of an AnxA5 protein that is expressed in *E. coli* strain BL21 (DE3) (e.g. as is widely commercially-available, and as described in Marder et al., 2014, *BMC Biotechnology*, 14:33). For example, it maybe that the level of gluconoylated AnxA5 protein in the product is within the range of 0.5 to 30%, or 0.5 to 20%, or 0.5 to 15%, or 0.5 to 10% of the total content of AnxA5 protein in the product. To put it another way, it may be that the level of gluconoylated AnxA5 protein in the product is below 40%, such as below 30%, 20%, 10%, 9%. 8%, 7%, 6%, 5%, 4%, 3%, 2%, or 1%, and preferably substantially 0%. The gluconoylated variants of Anx5 can, for example, be measured and quantified by using UPLC or HPLC chromatography instruments using appropriate anion exchange or reverse phase columns.

Accordingly, a fifth aspect of the present invention provides a composition comprising an AnxA5 protein, wherein the composition is the direct, or indirect product of (or is directly or indirectly obtainable by) a process according to any of the first, second, third or fourth aspects of the present invention. Optionally, the composition is a pharmaceutically acceptable and/or veterinarily acceptable composition.

J. Medical and Veterinary Uses

The sixth aspect of the present invention also provides the composition of the fifth aspect of the present invention for use in medicine. To put it another way, the sixth aspect of the present invention provides a method comprising administering to a human or animal in need thereof a therapeutically effective amount of a composition of the fifth aspect of the present invention.

In certain embodiments of the sixth aspect of the present invention, the composition of the fifth aspect of the present invention may be used:

(a) for prevention or reduction of risk of thrombosis (such as atherothrombosis) and/or plaque rupture, or for administration to patients belonging to a risk group, including but not limited to systemic lupus erythematosus (SLE) patients and/or patients who have or have had (or are at risk of) a upper respiratory tract or other infection (including pneumococcal infection) that can cause increased levels of antiphospholipid related antibodies, or to treat (either actively or prophylactically) or reduce the risk of thromboembolism, hemorrhagic or vasculitic stroke, myocardial infarction, angina pectoris or intermittent claudication, unstable angina, other forms of severe angina, or transient ischemic attacks (TIA), for example as further described in WO 2005/099744 (the contents of which are incorporated herein by reference);

(b) for the treatment, prophylaxis or reduction of risk of vascular dysfunction, angina pectoris, ischaemic heart disease, peripheral artery disease, systolic hypertension, migraine, type 2 diabetes and erectile dysfunction, reducing ischemic pain and/or treatment of a vascular disease rupture, for example as described in WO 2009/077764 (the contents of which are incorporated herein by reference);

(c) for the prophylaxis or treatment of restenosis (in particular neointima formation or thickening), or vascular inflammation, for example as described in WO 2009/103977 (the contents of which are incorporated herein by reference);

(d) for use in inhibiting the activity of oxidised cardiolipin (oxCL) and for treating, preventing and/or reducing the risk of developing a cardiovascular disease, an autoimmune disease or inflammatory condition, for example as described in WO 2010/069605 (the contents of which are incorporated herein by reference), including but not limited to the following diseases: cardiovascular disease (CVD), diabetes II, Alzheimer's disease, dementia in general, rheumatic diseases, atherosclerosis, high blood pressure, acute and/or chronic inflammatory conditions, myocardial infarction, acute coronary syndrome, stroke, transient ischemic attack (TIA), claudiction, angina, type I diabetes, rheumatoid arthritis, psoriasis, psoriatic arthritis, ankylosing spondylitis, Reiter's Syndrome, systemic lupus erythematosus, dermatomyositis, Sjogren's syndrome, lupus erythematosus, multiple sclerosis, myasthenia gravis, asthma, encephalitis, inflammatory bowel disease, chronic obstructive pulmonary disease (COPD), arthritis including osteoarthritis, idiopathic inflammatory myopathies (IIM), dermatomyositis (DM), polymyositis (PM), inclusion body myositis, an allergic disorder and/or osteoarthritis in a mammal; and (e) for the prevention and/or reduction of peri- or postoperative complications following surgical intervention, such as complications following vascular surgery, especially peripheral vascular surgery, for example as described in WO 2012/136819 (the contents of which are incorporated herein by reference).

In a further embodiment of the sixth aspect of the present invention, the composition of the fifth aspect of the present invention may be used in a prophylactic or therapeutic method of treating, preventing or reducing the risk of haematological disorders, including but not limited to sickle cell anemia.

In a further embodiment of the sixth aspect of the present invention, the composition of the fifth aspect of the present invention may be used in a prophylactic or therapeutic method of treating, preventing or reducing the risk of acute and chronic vascular inflammation, primary or secondary vascuilitis including but not limited to vasculitis with autoimmune components, and/or drug induced vasculitis. Accordingly, the present invention also provides a prophylactic or therapeutic method of treating, preventing or reducing the risk of vasculitides, including Behçet Disease, Cutaneous Vasculitis, Eosinophilic Granulomatosis with Polyangiitis (EGPA), Giant Cell Arteritis, Granulomatosis with Polyangiitis (GPA), Immunoglobulin A—Associated Vasculitis (IgAV), Microscopic Polyangiitis (MPA), Polyarteritis Nodosa (PAN), Polymyalgia Rheumatica, and Takayasu Arteritis. Polymyalgia Rheumatica may be of particular interest.

In a further embodiment of the sixth aspect of the present invention, the composition of the fifth aspect of the present invention may be used in a prophylactic or therapeutic method of treating, preventing or reducing the risk of retinal vein occlusion.

In a further embodiment of the sixth aspect of the present invention, the composition of the fifth aspect of the present invention may be used in a prophylactic or therapeutic method of (i) preventing, or reducing the rate of, the transmission of a viral infection; (ii) preventing, or protecting against, a viral infection; or (iii) treating a viral infection, in a subject, wherein the viral infection is caused by a virus selected from the group consisting of—
  (a) a virus capable of causing hemorrhagic fever (VHF), and
  (b) a virus that presents phosphatidylserine (PS) and mediates cell infection and/or internalisation through PS binding.

Accordingly, in one further embodiment, the present invention provides the composition of the fifth aspect of the present invention for use in a prophylactic or therapeutic method of preventing, or reducing the rate of, the transmission of a viral infection, in a subject, wherein the viral infection is caused by a virus capable of causing hemorrhagic fever (VHF).

That is to say, the present invention provides a prophylactic or therapeutic method of preventing, or reducing the rate of, the transmission of a viral infection, in a subject, wherein the viral infection is caused by a virus capable of causing hemorrhagic fever (VHF), the method comprising the administration of a therapeutically effective amount of the composition of the fifth aspect of the present invention to the subject.

To put it yet another way, this embodiment provides the composition of the fifth aspect of the present invention for use in the manufacture of a medicament for prophylaxis or therapy by preventing, or reducing the rate of, the transmission of a viral infection, in a subject, wherein the viral infection is caused by a virus capable of causing hemorrhagic fever (VHF).

In another embodiment, the present invention provides the composition of the fifth aspect of the present invention for use in a prophylactic or therapeutic method of preventing, or reducing the rate of, the transmission of a viral infection, in a subject, wherein the viral infection is caused by a virus that presents phosphatidylserine (PS) and mediates cell infection and/or internalisation through PS binding.

That is to say, the present invention provides a prophylactic or therapeutic method of preventing, or reducing the rate of, the transmission of a viral infection, in a subject, wherein the viral infection is caused by a virus that presents phosphatidylserine (PS) and mediates cell infection and/or internalisation through PS binding, the method comprising the administration of a therapeutically effective amount the composition of the fifth aspect of the present invention to the subject.

To put it yet another way, this embodiment provides the composition of the fifth aspect of the present invention for use in the manufacture of a medicament for prophylaxis or therapy by preventing, or reducing the rate of, the transmission of a viral infection, in a subject, wherein the viral infection is caused by a virus that presents phosphatidylserine (PS) and mediates cell infection and/or internalisation through PS binding.

In another embodiment, the present invention provides the composition of the fifth aspect of the present invention for use in a prophylactic or therapeutic method of preventing, or protecting against, a viral infection, in a subject, wherein the viral infection is caused by a virus capable of causing hemorrhagic fever (VHF).

That is to say, the present invention provides a prophylactic or therapeutic method of preventing, or protecting against, a viral infection, in a subject, wherein the viral infection is caused by a virus capable of causing hemorrhagic fever (VHF), the method comprising the administration of a therapeutically effective amount of the composition of the fifth aspect of the present invention to the subject.

To put it yet another way, this embodiment provides the composition of the fifth aspect of the present invention for use in the manufacture of a medicament for prophylaxis or therapy by preventing, or protecting against, a viral infection, in a subject, wherein the viral infection is caused by a virus capable of causing hemorrhagic fever (VHF).

In another embodiment, the present invention provides the composition of the fifth aspect of the present invention for use in a prophylactic or therapeutic method of preventing, or protecting against, a viral infection, in a subject, wherein the viral infection is caused by a virus that presents phosphatidylserine (PS) and mediates cell infection and/or internalisation through PS binding.

That is to say, the present invention provides a prophylactic or therapeutic method of preventing, or protecting against, a viral infection, in a subject, wherein the viral infection is caused by a virus that presents phosphatidylserine (PS) and mediates cell infection and/or internalisation through PS binding, the method comprising the administration of a therapeutically effective amount of the composition of the fifth aspect of the present invention to the subject.

To put it yet another way, this embodiment provides the composition of the fifth aspect of the present invention for use in the manufacture of a medicament for prophylaxis or therapy by preventing, or protecting against, a viral infection, in a subject, wherein the viral infection is caused by a virus that presents phosphatidylserine (PS) and mediates cell infection and/or internalisation through PS binding.

In another embodiment, the present invention provides the composition of the fifth aspect of the present invention for use in a prophylactic or therapeutic method of treating a viral infection, in a subject, wherein the viral infection is caused by a virus capable of causing hemorrhagic fever (VHF).

That is to say, the present invention provides a prophylactic or therapeutic method of treating a viral infection, in a subject, wherein the viral infection is caused by a virus capable of causing hemorrhagic fever (VHF), the method comprising the administration of a therapeutically effective amount of the composition of the fifth aspect of the present invention to the subject.

To put it yet another way, this embodiment provides the composition of the fifth aspect of the present invention for use in the manufacture of a medicament for prophylaxis or therapy by treating a viral infection, in a subject, wherein the viral infection is caused by a virus capable of causing hemorrhagic fever (VHF).

In another embodiment, the present invention provides the composition of the fifth aspect of the present invention for use in a prophylactic or therapeutic method of treating a viral infection, in a subject, wherein the viral infection is caused by a virus that presents phosphatidylserine (PS) and mediates cell infection and/or internalisation through PS binding.

That is to say, the present invention provides a prophylactic or therapeutic method of treating a viral infection, in a subject, wherein the viral infection is caused by a virus that presents phosphatidylserine (PS) and mediates cell infection and/or internalisation through PS binding, the method comprising the administration of a therapeutically effective amount of the composition of the fifth aspect of the present invention to the subject.

To put it yet another way, this embodiment provides the composition of the fifth aspect of the present invention for use in the manufacture of a medicament for prophylaxis or therapy by treating a viral infection, in a subject, wherein the viral infection is caused by a virus that presents phosphatidylserine (PS) and mediates cell infection and/or internalisation through PS binding.

According to a further embodiment of the present invention, there is provided the composition of the fifth aspect of the present invention for use in a method of treating a subject infected or suspected of being infected with a pathogen capable of causing hemorrhagic fever, such as a virus capable of causing hemorrhagic fever (VHF) or a bacteria capable of causing hemorrhagic fever (BHF).

To put it another way, this embodiment provides a method for treating a subject infected or suspected of being infected with a pathogen capable of causing hemorrhagic fever, such as a virus capable of causing hemorrhagic fever (VHF) or a bacteria capable of causing hemorrhagic fever (BHF), the method comprising the administration of a therapeutically effective amount of the composition of the fifth aspect of the present invention to the subject.

To put it yet another way, this embodiment provides the composition of the fifth aspect of the present invention for use in the manufacture of a medicament for treating a subject infected or suspected of being infected with a pathogen capable of causing hemorrhagic fever, such as a virus capable of causing hemorrhagic fever (VHF) or a bacteria capable of causing hemorrhagic fever (BHF).

According to another embodiment of the present invention, there is provided the composition of the fifth aspect of the present invention for use in a method of treating a subject that has been in contact with another subject who is infected or suspected of being infected with a pathogen capable of causing hemorrhagic fever, such as a virus capable of causing hemorrhagic fever (VHF) or a bacteria capable of causing hemorrhagic fever (BHF).

To put it another way, this embodiment provides a method for treating a subject that has been in contact with another subject who is infected or suspected of being infected with a pathogen capable of causing hemorrhagic fever, such as a virus capable of causing hemorrhagic fever (VHF) or a bacteria capable of causing hemorrhagic fever (BHF), the method comprising the administration of a therapeutically effective amount of the composition of the fifth aspect of the present invention to the subject.

To put it yet another way, this embodiment provides the composition of the fifth aspect of the present invention for use in the manufacture of a medicament for treating a subject that has been in contact with another subject who is infected or suspected of being infected with a pathogen capable of causing hemorrhagic fever, such as a virus capable of causing hemorrhagic fever (VHF) or a bacteria capable of causing hemorrhagic fever (BHF).

According to a further embodiment of the present invention, there is provided the composition of the fifth aspect of the present invention for use in a method of treating a subject that has been in contact with biological material present in or produced by another subject who is infected or suspected of being infected with a pathogen capable of causing hemorrhagic fever, such as a virus capable of causing hemorrhagic fever (VHF) or a bacteria capable of causing hemorrhagic fever (BHF).

To put it another way, this embodiment provides a method for treating a subject that has been in contact with biological material present in or produced by another subject who is infected or suspected of being infected with a pathogen capable of causing hemorrhagic fever, such as a virus capable of causing hemorrhagic fever (VHF) or a bacteria capable of causing hemorrhagic fever (BHF), the method comprising the administration of a therapeutically effective amount of the composition of the fifth aspect of the present invention to the subject.

To put it yet another way, this embodiment provides the composition of the fifth aspect of the present invention for use in the manufacture of a medicament for treating a subject that has been in contact with biological material present in or produced by another subject who is infected or suspected of being infected with a pathogen capable of causing hemorrhagic fever, such as a virus capable of causing hemorrhagic fever (VHF) or a bacteria capable of causing hemorrhagic fever (BHF).

In accordance with these foregoing embodiments of the present invention, the pathogen capable of causing hemorrhagic fever may be a VHF.

The viral hemorrhagic (or haemorrhagic) fevers (VHFs) are a diverse group of animal and human illnesses that may be caused by at least five distinct families of RNA viruses: the families Arenaviridae, Filoviridae, Bunyaviridae, Flaviviridae, and Rhabdoviridae. All types of VHF may be characterized by fever and bleeding disorders and all can progress to high fever, shock and death in many cases.

A subject who is suspected of being infected with a pathogen capable of causing hemorrhagic fever, such as a virus capable of causing hemorrhagic fever (VHF) or a bacteria capable of causing hemorrhagic fever (BHF) may be a subject with a history of coming into contact with the disease (e.g. by virtue of their employment as a health worker or due to the infection of a family member) and/or may be a subject that displays one or more signs or symptoms of being infected, prior to confirmatory diagnosis.

Signs and symptoms of VHFs characteristically include fever and increased susceptibility to bleeding (bleeding diathesis). Manifestations of VHF often also include flushing of the face and chest, small red or purple spots (petechiae), frank bleeding, swelling caused by edema, low blood pressure (hypotension), and shock. Malaise, muscle pain (myalgia), headache, vomiting, and diarrhea occur frequently. The severity of symptoms varies with the type of virus, with the "VHF syndrome" (capillary leak, bleeding diathesis, and circulatory compromise leading to shock) appearing in a majority of patients with filovirus hemorrhagic fevers (e.g., Ebola and Marburg), CCHF, and the South American hemorrhagic fevers, but in a small minority of patients with dengue, RVF, and Lassa fever.

In accordance with the sixth aspect of the present invention, the VHF may be Ebola, and subject may display one or more symptoms of Ebola, such as symptoms selected from initial clinical symptoms, such as excessive or profuse sweating, the onset of fever, myalgia, general malaise, and/or chills; and/or flu-like symptoms optionally accompanied by gastro-intestinal symptoms; maculo-papulary rash, petichae, conjunctival hemorrhage, epistaxis, melena, hematemesis, shock and/or encephalopathy; leukopenia (for example, associated with increased lymphoid cell apoptosis), thrombocytopenia, increased levels of aminotransferase, thrombin and/or partial thromboplastin times, fibrin split products detectable in the blood, and/or disseminated intravascular coagulation (DIC).

Definitive diagnosis is usually made at a reference laboratory with advanced biocontainment capabilities. The findings of laboratory investigation vary somewhat between the viruses but in general there is a decrease in the total white cell count (particularly the lymphocytes), a decrease in the platelet count, an increase in the blood serum liver enzymes, and reduced blood clotting ability measured as an increase in both the prothrombin (PT) and activated partial thromboplastin times (PTT). The hematocrit may be elevated. The serum urea and creatine may be raised but this is dependent on the hydration status of the patient. The bleeding time tends to be prolonged.

For example, being a BSL-4 agent, confirmed clinical laboratory diagnosis of viremia during the acute phase of Ebola virus infection is possible with suitable laboratory facilities. The assays that can be utilized are based on the stage of the disease.

During acute disease the assays include a) virus isolation using Vero or Vero E6 cell lines, b) RT-PCR and real time quantitative PCR assays with appropriate false negative and false positive controls, c) antigen capture ELISA, and d) IgM ELISA.

Later during the course of disease the tests that can be utilized include a) IgM and IgG ELISA using authentic viral antigens, and in the case of death, autopsy tissues can be utilized for a) antigen detection using immunostaining techniques, b) immunohistochemical aided detection of Ebola antigen (Zaki et al, J Infect Dis, 1999; 179 (Suppl. 1):S36e47., the contents of which are incorporated herein by reference in its entirety), and c) in-situ hybridization techniques for the detection of viral RNA.

The details of each of these techniques have been summarized in Saijo et al, Clin Vaccine Immunol 2006; 13:444e51, the contents of which are incorporated herein by reference in its entirety.

The ELISA based assay has been standardized by the CDC for the detection of Ebolavirus specific antibodies. The assay has high sensitivity and has been shown to be capable of detecting antibodies in the sera of humans exposed 10 years previously to Ebola. A cell-based plaque assay and an end point titration assay (TCID50) have also been developed to detect and quantitate filoviruses for use in pre-clinical studies (Shurtleff et al, Viruses 2012; 4:3511e30; Smither et al, J Virol Methods 2013; 193: 565e71, the contents of which are incorporated herein by reference in their entirety).

For example, the VHF may be a virus in a family selected from Filoviridae, Arenaviridae, Bunyaviridae, Flaviviridae or Rhabdoviridae.

The family Arenaviridae includes the viruses responsible for Lassa fever, Lujo virus, Argentine, Bolivian, Brazilian and Venezuelan hemorrhagic fevers.

The family Bunyaviridae includes the members of the Hantavirus genus that cause hemorrhagic fever with renal syndrome (HFRS), the Crimean-Congo hemorrhagic fever (CCHF) virus from the Nairovirus genus, Garissa virus and Ilesha virus from the Orthobunyavirus and the Rift Valley fever (RVF) virus from the Phlebovirus genus.

The family Filoviridae includes Ebola virus and Marburg virus.

The family Flaviviridae includes dengue, yellow fever, and two viruses in the tick-borne encephalitis group that cause VHF: Omsk hemorrhagic fever virus and Kyasanur Forest disease virus.

The isolation of a member of the Rhabdoviridae responsible for 2 fatal and 2 non-fatal cases of hemorrhagic fever in the Bas-Congo district of the Democratic Republic of Congo has also been reported. The non-fatal cases occurred in healthcare workers involved in the treatment of the other two, suggesting the possibility of person-to-person transmission.

Accordingly, for example in one embodiment of particular interest, the present invention may be applied to viruses in the family Filoviridae, such as Ebola virus and Marburg virus. In another embodiment of particular interest, the present invention may be applied to viruses in the family Flaviviridae, such as dengue virus.

Accordingly, the present invention provides for the composition of the fifth aspect of the present invention for use in a prophylactic or therapeutic method as described above, for (i) preventing, or reducing the rate of, the transmission of an Ebola infection; (ii) preventing, or protecting against, an Ebola infection; or (iii) treating an Ebola infection, in a subject infected or suspected of being infected with Ebola virus, or has been or is expected to be in contact with another subject who is infected or suspected of being infected with Ebola virus, or has been or is expected to be in contact with biological material present in or produced by another subject who is infected or suspected of being infected with Ebola virus.

Accordingly, the present invention provides for the composition of the fifth aspect of the present invention for use in a prophylactic or therapeutic method as described above, for (i) preventing, or reducing the rate of, the transmission of an Marburg infection; (ii) preventing, or protecting against, an Marburg infection; or (iii) treating a Marburg infection, wherein the a subject is infected or suspected of being infected with Marburg virus, or has been or is expected to be in contact with another subject who is infected or suspected of being infected with Marburg virus, or has been or is expected to be in contact with biological material present in or produced by another subject who is infected or suspected of being infected with Marburg virus.

Accordingly, the present invention provides for the composition of the fifth aspect of the present invention for use in a prophylactic or therapeutic method as described above, for (i) preventing, or reducing the rate of, the transmission of an Dengue fever virus infection; (ii) preventing, or protecting against, an Dengue fever virus infection; or (iii) treating a Dengue fever virus infection, wherein the subject is infected or suspected of being infected with Dengue fever virus, or has been or is expected to be in contact with another subject who is infected or suspected of being infected with Dengue fever virus, or has been or is expected to be in contact with biological material present in or produced by another subject who is infected or suspected of being infected with Dengue fever virus.

The present invention also provides the composition of the fifth aspect of the present invention for use in a method a described above, for treating, delaying the onset and/or delaying the progression of infection of the subject by the VHF or BHF.

The present invention also provides the composition of the fifth aspect of the present invention for use in a method a described above for preventing, reducing, delaying the onset of, or delaying the progression of, direct and/or indirect bacterial viral damage, as caused by the BHF or VHF, to the immune and/or vascular system in the subject.

For example, the present invention may be used for preventing, reducing, delaying the onset of, or delaying the progression of, direct and/or indirect bacterial or viral damage to the immune system in the subject, for example, in the context of an Ebola infection. For example, the bacterial or viral damage may be selected from damage to the innate immune response, damage to the acquired humoral response, damage to dendritic cells, damage to the regulation of the production of inflammatory factors such as interferon production (including ID production), damage to macrophages, and/or damage to monocytes.

The present invention may be used for preventing, reducing, delaying the onset of, or delaying the progression of, blood leakage (haemorrhage), hypotension, drop in blood pressure, shock or death in the subject.

The present invention may be used for preventing, reducing, delaying the onset of, or delaying the progression of, virally-induced nitric oxide damage to the vascular endothelium of the subject.

The present invention provides the composition of the fifth aspect of the present invention for use in a method of prevention, reduction, delaying the onset of, or delaying the progression of, damage, activation, death, and/or disruption to the integrity of, the vascular endothelium or endothelial cells thereof, in a subject infected or suspected of being infected with a pathogen capable of causing hemorrhagic fever, such as a VHF or BHF. The integrity of the vascular endothelium or endothelial cells thereof may, for example, be determined by the extent of cellular or vascular epithelial leakage and/or by the detection of one or more haemorrhagic events, or the formation of oedema and/or dehydration of the subject.

The present invention provides the composition of the fifth aspect of the present invention for use in a method of prevention, reduction, delaying the onset of, or delaying the progression of, damage, activation, death, and/or disruption to the integrity of, the vascular endothelium or endothelial cells thereof, in a subject that has been or is expected to be in contact with another subject who is infected or suspected of being infected with a pathogen capable of causing hemorrhagic fever, such as a VHF or BHF.

The present invention provides the composition of the fifth aspect of the present invention for use in a method of prevention, reduction, delaying the onset of, or delaying the progression of, damage, activation, death, and/or disruption to the integrity of, the vascular endothelium or endothelial cells thereof, in a subject that has been or is expected to be in contact with biological material present in or produced by another subject who is infected or suspected of being infected with a pathogen capable of causing hemorrhagic fever, such as a VHF or BHF.

A further embodiment of the present invention provides for the composition of the fifth aspect of the present invention for use as described above by reference to the various embodiments of the present invention in a prophylactic or therapeutic method, wherein the viral infection is caused by a virus that presents phosphatidylserine (PS) and mediates cell infection and/or internalisation through PS binding. Alternatively, the viral infection may be caused by a virus that presents one or more other types of phospholipids that are bound by Annexin A5 and/or other moieties that are bound by Annexin A5.

Viruses that presents phosphatidylserine (PS) and mediates cell infection and/or internalisation through PS binding can particularly include enveloped viruses comprising phosphatidylserine (PS) in their envelope, especially in the outer layer. The presentation of PS by a virus can be determined by methods known in the art, for example, using an ELISA study to measure the binding of Annexin A5 to the virus. A suitable method can, for example, include the ELISA measurement of haemagglutinin (HA)-tagged Annexin A5 binding to anti-HA antisera, such as described in Moller-Tank, et al, 2013, *J. Virol.*, 87(15), 8327-8341 (the contents of which are incorporated herein by reference).

A group of viruses of particular interest to the present invention includes those which mediate cell infection and/or internalisation through binding with a phosphatidylserine-mediated virus entry enhancing receptor (PVEER). PVEERs are discussed in Moller Tank, et al, 2013, *J. Virol.*, 87(15), 8327-8341, and one example thereof is the T-cell immunoglobulin and mucin 1 (TIM-1) receptor. Further examples may include TIM-4, Gas6 or Protein S/Axl, Mer, and Tyro3, and MFG-E8/integrin $\alpha v \beta 3$ or $\alpha v \beta 5$ Ebola is an example of one virus of particular interest that presents phosphatidylserine (PS) and mediates cell infection and/or internalisation through PS binding with TIM-1. Moller Tank, et al, 2013, *J. Virol.*, 87(15), 8327-8341.

The present invention recognises that Annexin A5, and the composition of the fifth aspect of the present invention, may be used to inhibit or interrupt the PS-mediated cell infection and/or internalisation of viruses, such as Ebola virus, through PVEERs such as TIM-1, and thereby by can be useful in a prophylactic or therapeutic method of (i) preventing, or reducing the rate of, the transmission of a viral infection; (ii) preventing, or protecting against, a viral infection; or (iii) treating a viral infection, in a subject, wherein the viral infection is caused by a virus that presents phosphatidylserine (PS) and mediates cell infection and/or internalisation through PS binding.

Viruses that presents phosphatidylserine (PS) may, for example, be selected from the group consisting of a virus in the family Filoviridae (such as Ebola and Marburg); the family Flaviviridae; hepatitis A; alpha viruses; baculoviruses; and arena viruses. The viruses may be infectious in, or only in, humans. The viruses may be infectious in, or only in, non-human animals, such as any one or more of animals selected from the group consisting of dogs, cats, cattle, sheep, pigs, goats, rodents, camels, domesticated animals, and wild animals.

PVEERs such as TIM-1, can be involved in the internalisation of viruses into various cell types. In one embodiment, cell types of particular interest for protection and/or treatment in accordance with the present invention may include one or more cell types selected from the group consisting of epithelial cells (including vascular epithelial cells), mast cells, B-cells, and T-cells such as CD4+ cells or CD8+ cells and particularly activated CD4+ cells.

TIM-1, also known as HAVCR1 and KIM-1, has been identified as a susceptibility gene for human asthma (McIntire et al, 2003, *Nature* 425:576). One published amino acid sequence for human TIM-1 protein is shown as:

(SEQ ID NO: 2)
MHPQVVILSLILHLADSVAGSVKVGGEAGPSVTLPCHYSGAVTSMCWR

GSCSLFTCQNGIVWTNGTHVTYRKDTRYKLLGDLSRRDVSLTIENTAV

SDSGVYCCRVEHRGWFNDMKITVSLEIVPPKVTTTPIVTTVPTVTTVR

TSTTVPTTTTVPMTTVPTTTVPTTMSIPTTTTVLTTMTVSTTTSVPTT

TSIPTTTSVPVTTTVSTFVPPMPLPRQNHEPVATSPSSPQPAETHPTT

LQGAIRREPTSSPLYSYTTDGNDTVTESSDGLWNNQTQLFLEHSLLTA

NTTKGIYAGVCISVLVLLALLGVIIAKKYFFKKEVQQLSVSFSSLQIK

ALQNAVEKEVQAEDNIYIENSLYATD.

TIM-1 is a type I membrane protein with an extracellular region containing an IgV domain, a mucin-rich domain, and a short membrane-proximal stalk containing N-linked glycosylation sites (Ichimura et al, 1998, *J. Biol, Chem.* 273 (7):4135-42). The TIM-1 IgV domain has a disulfide-dependent conformation in which the CC' loop is folded onto the GFC β strands, resulting in a distinctive cleft formed by the CC' and FG loops (Santiago et al, 2007, *Immunity* 26(3):299-310). The cleft built by the CC' and FG loops is a binding site for phosphatidylserine (Kobayashi et al, 2007, *Immunity* 27(6):927-40). Antibodies directed to the CC'/FG cleft of the TIM-1 IgV domain inhibit TIM-1 binding to phosphatidylserine and dendritic cells and exhibit therapeutic activity in vivo in a humanized mouse model of allergic asthma (Sonar et al, 2010, *J. Clin. Invest.* 120: 2767-81).

A further embodiment of the present invention is based on the use of the composition of the fifth aspect of the present invention to prevent, inhibit or reduce the ability of the IgV domain of TIM-1, and other PVEERs, from binding to PS presented to it. The AnxA5 protein in the composition of the fifth aspect of the present invention preferably also has the ability to bind PS and, in accordance with this embodiment of the present invention, is capable of competing with the PVEER to bind to PS.

Accordingly, in one further embodiment, the composition of the fifth aspect of the present invention may be used in a method which inhibits phosphatidylserine binding to TIM-1 (or other PVEER).

For example, this may be prophylactically or therapeutically useful in the context of inhibiting, reducing or preventing the infection of cells with viruses that present phosphatidylserine (PS) and mediate cell infection and/or internalisation through PS.

Alternatively, this may be prophylactically or therapeutically useful in the context of addressing other medical conditions that involve the binding of PS to TIM-1 (or other PVEERs). TIM-1 associated disorders are discussed further below.

Therefore, in another embodiment, the present invention provides a method of inhibiting or reducing binding of TIM-1 or other PVEER, to phosphatidylserine, the method comprising contacting a first cell that expresses TIM-1 or other PVEER with an amount of the composition of the fifth aspect of the present invention effective to inhibit or reduce binding of the first cell to a second cell that contains phosphatidylserine on its cell surface or to a virus that present phosphatidylserine (PS) on its surface. The method may be an in vivo or in vitro method. In the case of an in vivo method, it may be to treat or prevent a condition that involves the binding of PS to TIM-1 or other PVEER.

In other words, this embodiment of the present invention also provides the composition of the fifth aspect of the present invention for use in a prophylactic or therapeutic method for inhibiting or reducing the binding of TIM-1 or other PVEER, to phosphatidylserine, in a patient in need thereof.

In another embodiment, the present invention provides a method of inhibiting or reducing binding of PS to a TIM-1 or other PVEER on a dendritic cell, the method comprising contacting a dendritic cell that expresses TIM-1 or other PVEER with an amount of the composition of the fifth aspect of the present invention effective to inhibit or reduce binding of PS to the dendritic cell. The method may be an in vivo or in vitro method. In the case of an in vivo method, it may be to treat or prevent a condition that involves the binding of PS to TIM-1 or other PVEER on a dendritic cell.

In other words, this embodiment of the present invention also provides the composition of the fifth aspect of the present invention for use in a prophylactic or therapeutic method for inhibiting or reducing the binding of PS to TIM-1 or other PVEER on a dendritic cell, in a patient in need thereof.

Also disclosed is a method of treating or preventing an inflammatory or autoimmune condition, the method comprising administering to a mammal having an inflammatory or autoimmune condition a pharmaceutical composition comprising a therapeutically effective amount of the composition of the fifth aspect of the present invention.

In other words, this embodiment of the present invention also provides the composition of the fifth aspect of the present invention for use in a prophylactic or therapeutic method for preventing, treating or reducing inflammatory or autoimmune condition.

Also disclosed is a method of treating or preventing asthma, the method comprising administering to a mammal having asthma a pharmaceutical composition comprising the composition of the fifth aspect of the present invention.

In other words, this embodiment of the present invention also provides the composition of the fifth aspect of the present invention for use in a prophylactic or therapeutic method for preventing, treating or reducing asthma.

Also disclosed is a method of treating or preventing an atopic disorder, the method comprising administering to a mammal having an atopic disorder a pharmaceutical composition comprising a therapeutically effective amount of the composition of the fifth aspect of the present invention. The atopic disorder can be, for example, atopic dermatitis, contact dermatitis, urticaria, allergic rhinitis, angioedema, latex allergy, or an allergic lung disorder (e.g., asthma, allergic bronchopulmonary aspergillosis, or hypersensitivity pneumonitis).

In other words, this embodiment of the present invention also provides the composition of the fifth aspect of the present invention for use in a prophylactic or therapeutic method for preventing, treating or reducing an atopic disorder.

The composition of the fifth aspect of the present invention be used as described herein to treat or prevent a variety of TIM-1 associated disorders, and other PVEER-associated disorders, including immunological disorders, such as inflammatory and autoimmune disorders.

The term "treating" includes the meaning of administering a substance or composition described herein in an amount, manner, and/or mode effective to improve a condition, symptom, or parameter associated with a disorder or to prevent progression or exacerbation of the disorder (including secondary damage caused by the disorder) to either a statistically significant degree or to a degree detectable to one skilled in the art.

A subject who is at risk for, diagnosed with, or who has one of these disorders can be administered the composition of the fifth aspect of the present invention in an amount and for a time to provide an overall therapeutic effect. The composition of the fifth aspect of the present invention can be administered alone (monotherapy) or in combination with other agents (combination therapy), either in admixture or by separate, simultaneous or sequential administration. In the case of a combination therapy, the amounts and times of administration can be those that provide, e.g., an additive or a synergistic therapeutic effect. Further, the administration of the composition of the fifth aspect of the present invention (with or without the second agent) can be used as a primary, e.g., first line treatment, or as a secondary treatment, e.g., for subjects who have an inadequate response to a previously administered therapy (i.e., a therapy other than one with an AnxA5 protein).

Diseases or conditions treatable with the composition of the fifth aspect of the present invention described herein include, e.g., ischemia-reperfusion injury (e.g., organ ischemia-reperfusion injury such as liver or renal ischemia-reperfusion injury), allergy, asthma, inflammatory bowel disease (IBD), Crohn's disease, transplant rejection, pancreatitis, and delayed type hypersensitivity (DTH).

Additional diseases or conditions treatable with the composition of the fifth aspect of the present invention described herein include, e.g., autoimmune disorders.

Systematic lupus erythromatosis (SLE; lupus) is a TH-2 mediated autoimmune disorder characterized by high levels of autoantibodies directed against intracellular antigens such as double stranded DNA, single stranded DNA, and histones.

Examples of other organ-specific or systemic autoimmune diseases suitable for treatment with the composition of the fifth aspect of the present invention described herein include myasthenia gravis, autoimmune hemolytic anemia, Chagas' disease, Graves disease, idiopathic thrombocytopenia purpura (ITP), Wegener's Granulomatosis, poly-arteritis Nodosa and Rapidly Progressive Crescentic Glomerulonephritis. See, e.g., Benjamini et al., 1996, Immunology, A Short Course, Third Ed. (Wiley-Liss, New York). In addition, rheumatoid arthritis (RA) is suitable for treatment with Annexin A5 as described herein.

Additional TIM-1 associated diseases or conditions treatable with the composition of the fifth aspect of the present invention described herein include, e.g., Graft-Versus Host Disease (GVHD). GVHD exemplifies a T cell-mediated condition that can be treated using Annexin A5 described herein. GVHD is initiated when donor T cells recognize host antigens as foreign. GVHD, often a fatal consequence of bone marrow transplantation (BMT) in human patients, can be acute or chronic. Acute and chronic forms of GVHD exemplify the development of antigen specific Th1 and Th2 responses, respectively. Acute GVHD occurs within the first two months following BMT, and is characterized by donor cytotoxic T cell-mediated damage to skin, gut, liver, and other organs. Chronic GVHD appears later (over 100 days post-BMT) and is characterized by hyperproduction of immunoglobulin (Ig), including autoantibodies, and damage to the skin, kidney, and other organs caused by Ig-deposition. Nearly 90% of acute GVHD patients go on to develop chronic GVHD. Chronic GVHD appears to be a Th2 T cell mediated disease (De Wit et al, 1993, J. Immunol. 150:361-366). Acute GVHD is a Th1 mediated disease (Krenger et al, 1996, Immunol. Res. 15:50-73; Williamson et al, 1996, J. Immunol. 157:689-699). T cell cytotoxicity is a characteristic of acute GVHD. The consequence of donor anti-host cytotoxicity can be seen in various ways. First, host lymphocytes are rapidly destroyed, such that mice experiencing acute GVHD are profoundly immunosuppressed. Second, donor lymphocytes become engrafted and expand in the host spleen, and their cytotoxic activity can be directly measured in vitro by taking advantage of cell lines that express the host antigens that can be recognized (as foreign) by the donor cells. Third, the disease becomes lethal as additional tissues and cell populations are destroyed.

Additional TIM-1 associated diseases or conditions treatable with the composition of the fifth aspect of the present invention described herein include, e.g., atopic disorders. Atopic disorders are characterized by the expression by immune system cells, including activated T cells and APC, of cytokines, chemokines, and other molecules which are characteristic of Th2 responses, such as the IL-4, IL-5 and IL-13 cytokines, among others. Such atopic disorders therefore will be amenable to treatment with the composition of the fifth aspect of the present invention as described herein. Atopic disorders include airway hypersensitivity and distress syndromes, atopic dermatitis, contact dermatitis, urticaria, allergic rhinitis, angioedema, latex allergy, and an allergic lung disorder (e.g., asthma, allergic bronchopulmonary aspergillosis, and hypersensitivity pneumonitis).

Additional TIM-1 associated diseases or conditions treatable with the composition of the fifth aspect of the present invention as described herein include, e.g., numerous immune or inflammatory disorders. Immune or inflammatory disorders include, but are not limited to, allergic rhinitis, autoimmune hemolytic anemia; acanthosis nigricans; Addison's disease; alopecia areata; alopecia universalis; amyloidosis; anaphylactoid purpura; anaphylactoid reaction; aplastic anemia; ankylosing spondylitis; arteritis, cranial; arteritis, giant cell; arteritis, Takayasu's; arteritis, temporal; ataxia-telangiectasia; autoimmune oophoritis; autoimmune orchitis; autoimmune polyendocrine failure; Behcet's disease; Berger's disease; Buerger's disease; bronchitis; bullous pemphigus; candidiasis, chronic mucocutaneous; Caplan's syndrome; post-myocardial infarction syndrome; post-pericardiotomy syndrome; carditis; celiac sprue; Chagas's disease; Chediak-Higashi syndrome; Churg-Strauss disease; Cogan's syndrome; cold agglutinin disease; CREST syndrome; Crohn's disease; cryoglobulinemia; cryptogenic fibrosing alveolitis; dermatitis herpetifomis; dermatomyositis; diabetes mellitus; Diamond-Blackfan syndrome; DiGeorge syndrome; discoid lupus erythematosus; eosinophilic fasciitis; episcleritis; drythema elevatum diutinum; erythema marginatum; erythema multiforme; erythema nodosum; Familial Mediterranean fever; Felty's syndrome; pulmonary fibrosis; glomerulonephritis, anaphylactoid; glomerulonephritis, autoimmune; glomerulonephritis, post-streptococcal; glomerulonephritis, posttransplantation; glomerulopathy, membranous; Goodpasture's syndrome; granulocytopenia, immune-mediated; granuloma annulare; granulomatosis, allergic; granulomatous myositis; Grave's disease; Hashimoto's thyroiditis; hemolytic disease of the newborn; hemochromatosis, idiopathic; Henoch-Schoenlein purpura; hepatitis, chronic active and chronic progressive; histiocytosis X; hypereosinophilic syndrome; idiopathic thrombocytopenic purpura; Job's syndrome; juvenile dermatomyositis; juvenile rheumatoid arthritis (Juvenile chronic arthritis); Kawasaki's disease; keratitis; keratoconjunctivitis sicca; Landry-Guillain-Barre-Strohl syndrome; leprosy, lepromatous; Loeffler's syndrome; lupus; Lyell's syndrome; lyme disease; lymphomatoid granulomatosis; mastocytosis, systemic; mixed connective tissue disease; mononeuritis multiplex; Muckle-Wells syndrome; mucocutaneous lymph node syndrome; mucocutaneous lymph node syndrome; multicentric reticulohistiocytosis; multiple sclerosis; myasthenia gravis; mycosis fungoides; necrotizing vasculitis, systemic; nephrotic syndrome; overlap syndrome; panniculitis; paroxysmal cold hemoglobinuria; paroxysmal nocturnal hemoglobinuria; pemphigoid; pemphigus; pemphigus erythematosus; pemphigus foliaceus; pemphigus vulgaris; pigeon breeder's disease; polyarteritis nodosa; polymyalgia rheumatic; polymyositis; polyneuritis, idiopathic; Portuguese familial polyneuropathies; pre-eclampsia/eclampsia; primary biliary cirrhosis; progressive systemic sclerosis (scleroderma); psoriasis; psoriatic arthritis; pulmonary alveolar proteinosis; pulmonary fibrosis, Raynaud's phenomenon/syndrome; Reidel's thyroiditis; Reiter's syndrome, relapsing polychrondritis; rheumatic fever; rheumatoid arthritis; sarcoidosis; scleritis; sclerosing cholangitis; serum sickness; Sezary syndrome; Sjogren's syndrome; Stevens-Johnson syndrome; Still's disease; subacute sclerosing panencephalitis; sympathetic ophthalmia; systemic lupus erythematosus; yransplant rejection; ulcerative colitis; undifferentiated connective tissue disease; urticaria, chronic; urticaria, cold; uveitis; vitiligo; Weber-Christian disease; Wegener's granulomatosis, or Wiskott-Aldrich syndrome.

The present invention will now be described with reference to one or more non-limiting examples.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Comparative Example 1

The process of Marder et al., 2014, *BMC Biotechnology*, 14:33 reports on the processing of 1 L cultures and consists of two 38,900 g centrifugations of 30 minute duration, which in the first centrifugation step precipitate the Annexin A5 bound to cell debris, and in the second centrifugation step precipitate the cell debris while keeping the Annexin A5 in solution.

The following analysis is provided to calculate the implications of scaling up the process of Marder et al., from 1 L to the commercially-relevant culture volume of 1000 L.

Based on a selection of the best centrifuges currently available with the best rotors for maximal throughput, they can take 6×250 ml=1.5 liter and can achieve 30,200-38,400 g. Examples are expensive carbon fiber lightweight rotor (Fiberlite F14-6×250y Fixed-Angle Rotor) for use in Thermo Scientific™ Sorvall™ LYNX superspeed centrifuges or the JLA-16.250 Rotor, Fixed Angle, Aluminum, Biosafety Lid, 6×250 mL, 38,400×g for use in Beckmancoulters Avanti JXN-26. Using such high-end advanced centrifuges, to load the centrifuge, start and accelerate to the required speed, spend 30 minutes at maximum G-force and then allowing for careful breaking to a standstill so as not to disturb the pellet, then emptying the rotor would take about 45 min.

That is, the best centrifuges currently available allow the processing of 1.5 liter per 45 min.

Marder et al. reports (in the section entitled "Purification") that 3 g of wet weight of the cells were suspending in 30 mL of buffer before sonication and centrifugation. Accordingly, the wet cell weight (WCW) concentration used by Marder et al., during the centrifugations was (3 gram into 30 ml buffer)=9.1% WCW.

Marder et al. (under the heading "Bioreactor cultivation" on second page) also reports a mean value of 27.48 g (DCW) $L^{-1}$ (SD=1.96) for the biomass concentration. Therefore, the dry cell weight (DCW) concentration in Marder's fermenter was 27.48 gr/L=2.748%. It is known that 1 gram DCW=about 4 gram Wet Cell Weight (WCW). Therefore, in the cell concentration fermenter there was a WCW concentration of 2.748×4=11.0%. If one scales this up to a 1000 L culture volume, and make a conservative assumption of 5% cell loss during harvest from 1000 L, then the WCW in a 1000 L tank using Marder's method would=1000×11%×0.95=104.5 kg WCW.

Marder's centrifugation method used a 9.1% WCW concentration during the centrifugation step. Therefore, 104.5 kg WCW from a 1000 L culture would need to be diluted to a 9.1% WCW concentration, which requires a total volume to be centrifuged of 1148 L.

Making the generous assumption that a bio-manufacturing facility has two high-end advanced centrifuges, so that one can be used for pelleting the Annexin with cell debris (first centrifugation), while the other can work in parallel with the second centrifugation when the Annexin is in solution and the cell debris is pelleted then:

Total time for centrifuging the 1148 L solution is, wherein the centrifuges can process 1.5 liter per 45 min=1148/1.5=766 centrifugations at 45 min each=34,470 min=574.5 hours.

Assuming that the bio-manufacturing facility operated 12 hours per day, then the processing of the WCW from a 1000 L tank using the method of Marder et al will take 48 days of work, or (assuming five working days per week) 10 weeks just for the centrifugations.

In total, approximately an additional two weeks would be needed for fermentation, downstream processing and other operations. This give 12 weeks in manufacturing plant to prepare and process the cells from a 1000 L culture, assuming that the bio-manufacturing facility is fully occupied with that one process, and so no other production can occur in the same facility meanwhile. This is despite the generous assumption that two centrifuges are available. If only one centrifuge is used, the manufacturing time would be 22 weeks for one 1000 L batch.

In contrast, as discussed below, the methods of the present invention can process a 1000 L culture in just two weeks, i.e. around 6-times quicker (and, also provide a far higher quality product, with a far higher yield, than the product of the Marder et al. process).

The manufacturing cost is direct proportional to the manufacturing time as the manufacturing plant will be occupied and no other production can occur in the same plant meanwhile.

The yield of Annexin A5 in the process of the present invention is calculated to be 2-3 times higher per batch than the product produced by Marder et al. This makes the manufacturing cost per gram Annexin A5 protein between (6×2-3=) 12-18 times higher for the Marder process.

Furthermore, the purity of the protein from the Marder process would not be suitable for human use. Despite elaborate centrifugations, only one anion exchange chromatography step is used which is far below the requirements to reach sufficient purity with regards to both in-process related impurities (especially endotoxin) and product related variants. Marder does not show any data on endotoxin levels or other impurities further indicating lack of suitability for pharmaceutical use.

In addition, the very slow centrifugation operations of the Marder process require the Annexin A5 protein to be in an unstable environment for long period of time. This is likely result in product degradation or product modification, and is a further drawback of long manufacturing operation time, with negative implications for product quality.

Example 1

Abbreviations

| | | | |
|---|---|---|---|
| AP | Aqua Purificata (purified water) | NF | national formulary |
| BV | Bovenau | NL | norm litre |
| cIEF | capillary isoelectric focussing | NMWCO | Nominal molecular weight cut-off |
| CX | Cation Exchange Chromatography | n.p. | not performed |
| CFU | colony forming unit | n.s. | not specified |
| CR | Column Room | OD | optical density |
| CRG | Column Room Grade | PAGE | Poly Acrylamide Gel Electrophoresis |
| CV | Column Volume | PBS | Phosphate buffer saline |
| DF | Diafiltration | PC | polycarbonate |
| DP | Drug Product | PETG | polyethylene terephthalate copolyester, glycol modified |
| DSP | Downstream Process | PES | Polyethersulfone |
| DS | Drug Substance | Ph.Eur. | European Pharmacopoeia |
| EU | Endotoxin units | PP | polypropylene |
| EVA | ethylene vinyl acetate copolymer | PPG | polypropylene glycol |
| EVOH | Ethylene vinyl ethanol copolymer | PVDF | Polyvinylidene Fluoride |
| FF | forward flow test / diffusion test | QA | Quality Assurance Department |
| FIO | For Information Only | QC | Quality Control Department |
| g | gram | RHB | Richter-Helm BioLogics |
| h | hours | RPC | Reversed Phase Chromatography |
| H | Hanover | rpm | rotation per minute |
| HCP | Host Cell Protein | RT | Room Temperature (20-25° C.) |
| HH | Hamburg | SDS | Sodium Dodecyl Sulphate |
| ID | inner diameter | SEC | Size Exclusion Chromatography |
| IEX | Ion Exchange Chromatography | TFF | Tangential Flow Filtration |
| IPC | In-Process Control | TMP | Trans Membrane Pressure |
| L | Litre | UF | Ultrafiltration |
| LAF | Laminar Air Flow | USP | Upstream Process |
| LDPE | Low-density Polyethylene | USP | US Pharmacopoeia |
| MCB | Master cell bank | v/v | Volume per Volume |
| min | minutes | WB | western blot |
| MRS | master reference standard | WCB | Working Cell Bank |
| n. a. | not applicable | WFI | Water for Injection |

Introduction

The 320 amino acid containing recombinant ~36 kDa protein Annexin A5 is expressed in the cytoplasm of the *E. coli* BL21/pHIP.ANXA5. Recombinant Annexin A5 is produced mainly in its soluble form. A heat inducible expression plasmid pHIP, carrying the coding sequence for Annexin A5, is used. Selective marker is a kanamycin resistance gene. A MCB of the respective clone has been established and extensively characterized.

The manufacturing process is scaled-up from lab scale equivalent to 3 L fermentation volume to large scale equivalent to 100 L fermentation volume.

The developed process includes an efficient anion exchange capture from crude lysate followed by an affinity step on immobilized heparin in the presence of calcium. This intermediate affinity step is highly specific for Annexin A5. As final polishing step a high resolution anion exchange chromatography is used. The polishing step allows a separation of product related impurities. Formulation is conducted by ultra-diafiltration using a 10 kDa NMWCO cassette.

This example describes and evaluates the planned adaptations/changes in the manufacturing process, determines operational parameters and necessary measures to assure a successful transfer and defines acceptance criteria to determine its success. A successful transfer is shown by the performance of a downstream process run implementing the adaptations to the lab scale procedure with respect to scale-up resulting in DS of comparable yield and quality.

The overall project objective is the development of a cGMP manufacturing process for Annexin A5.

Procedure—Process Comparison and Evaluation

In this section the process parameters, raw materials, consumables, buffers and equipment used are evaluated.

FIG. 2 shows a schematic overview of the complete process for manufacturing of Annexin A5.

Table 1 compares and evaluates the raw materials used by the 3 L and 100 L processes.

TABLE 1

Comparison of raw materials used by 3L and 100 L processes

| Raw material | 3 L process | | 100 L process | |
| --- | --- | --- | --- | --- |
| | Supplier | Quality | Supplier | Quality |
| Tris (hydroxymethyl) aminomethane (Tris) | Merck | Ph.Eur. | Merck | Ph.Eur. |
| Magnesium chloride heptahydrate | Merck | Ph.Eur. | Merck | Ph.Eur. |
| Sodium chloride | Merck | Ph.Eur. | Merck | Ph.Eur. |
| Tween-80 (polysorbate) | Merck | Ph.Eur. | Merck | Ph.Eur. |
| Sodium hydroxide | Merck | Ph.Eur. | Merck | Ph.Eur. |
| Benzonase Nuclease | Merck/Novagen | Purity >90% | Merck | Purity >90% |
| $CaCl_2 \times 2H_2O$ | Merck | Ph.Eur. | Merck | Ph.Eur. |
| Titriplex III | Merck | Ph.Eur. | Merck | Ph.Eur. |
| Bis-Tris 1,3-bis[tris (Hydroxymethyl)-methylamino]propane | Merck | Ultrol grade | Sigma | Bio Ultra |
| Water | RHB HH | Bidest/Ampuva (Fresenius) | Fresenius Biochrom | Ph.Eur. |
| Ethanol | Merck | Emprove | Merck | EMSURE® ACS, ISO |
| Hydrochloric acid | Merck | Emprove exp.Ph.Helv | Merck | p.A. |
| ortho-Phosphoric acid | Merck | Emprove exp.Ph.Eur | Merck | Ph.Eur. |
| Sodium hydroxide 33% | Reher&Ramsden | n.a. | — | — |

TABLE 2

List of consumables

| | 3 L process | | 100 L process | |
| --- | --- | --- | --- | --- |
| Consumable | Supplier | Quality | Supplier | Quality |
| Depth Filter Cuno SP 60 | 3M, CUNO | USP class VI | 3M, CUNO | USP class VI |
| Q Sepharose XL (AX Resin) | GE Healthcare | Manufacturers monograph | GE Healthcare | Manufacturers monograph |
| Heparin HyperD M (AF Resin) | Pall | Manufacturers monograph | Pall | Manufacturers monograph |
| Source15 Q (AX Resin) | GE Healthcare | Manufacturers monograph | GE Healthcare | Manufacturers monograph |
| 0.2 μm Filter Sartopore 2 0.45-0.2 μm | Sartorius | USP class VI | Sartorius | USP class VI |
| 0.2 μm Filter EKV, Supor | Pall | USP class VI | Pall | USP class VI |
| UF/DF cassette, Hydrosart, 10 kDa Membrane | Sartorius | USP class VI | Sartorius | USP class VI |

General Remarks:

All consumables used are single-use or product-dedicated materials.

Table 2 compares and evaluates the consumables used by the 3 L and 100 L processes. The consumables (sampling devices, and tubing) should not have an impact on the product quality and yield of the DSP process. All materials used fulfil the required specification.

Bags used for buffer storage and as an intermediate product container are from Sartorius with an PE/EVOH layer (CX5-14 film) throughout the process. Bags validated by the manufacturer with respect to e.g. sterility, low Endotoxin as well as leachables and extractables.

All other consumables used including materials with product contact such as tubing, connectors, sampling systems or sample containers are fit for purpose at the respective step of the process. This includes usually a USP class VI certification, sterility and/or low Endotoxin if applicable. Platinum-cured silicone tubing is used throughout the DSP, except C-Flex tubing preassembled to the bags. All consumables used are animal derived component free or a TSE certificate is available.

Table 3 compares the equipment used by the 3 L and 100 L processes for manufacturing of Annexin A5.

TABLE 3

| | List of equipment used | | | |
|---|---|---|---|---|
| | 3 L process | | 100 L process | |
| Equipment | Type | Manufacturer | Type | Manufacturer |
| Thermometer | n.a. | Hanna | ≥0-100° C. | Amarell |
| Pipet | n.a. | Eppendorf | different | Eppendorf |
| Pump | n.a. | Watson Marlow | 604 U/R | Watson Marlow |
| Pump | n.a. | Watson Marlow | 505 DU | Watson Marlow |
| Pump | n.a. | n.a. | 1000 S | QuattroFlow |
| LPLC-system 1 | Äkta 100 | GE Healthcare | BioProcess | GE Healthcare |
| Capture Column | XK 50 | GE Healthcare | BPG300 | GE Healthcare |
| Intermediate Column | XK 50 | GE Healthcare | BPG300 | GE Healthcare |
| Polishing Column | FineLine 70 | GE Healthcare | Fineline200 | GE Healthcare |
| Ultrafiltration system | n.a. | n.a. | UFDF-H1 | PALL |
| Photometer | Ultrospec 3100 | GE Healthcare | Ultrospec × 300 | GE Healthcare |
| pH-/conductivity Meter + Printer | MPC227 | Mettler-Toledo | CG HI 730 P | Schott Hanna WTW |
| Laminar air flow cabinet (LAF) | n.a. | Herasafe | HS | Herasafe |
| Magnet Stirrer | n.a. | IKA | RET/REO | IKA |
| Vacuum Pump | n.a. | KNF | — | — |
| Filter integrity testing device | n.a. | n.a. | AquaWIT Exacta | PALL Millipore |

Media, buffers and solutions as shown in Table 4. Specifications of buffers are adapted only with respect to conductivity and based on test buffer preparations. Buffers are prepared before the process, tested according their specification, microfiltrated (0.2 μm filter) and stored (holding time ≤3 months at RT). Sampling of buffers (as reference; analysis: Endotoxin, Bioburden) are performed at the time point of use.

TABLE 4

| | List of Media and solutions | | |
|---|---|---|---|
| | 3 L process | | 100 L process |
| Buffer | Composition | Application | Composition |
| homogenisation buffer 1 | 50 mM Tris; pH 7.4, 1 mM $MgCl_2$; 1% Tween80 | Homogenisation | 50 mM Tris; pH 7.4, 1 mM $MgCl_2$; 1% Tween80 |
| Conditioning post homogenisation buffer 1 | 1% Tween80 (w/v) | Capture | 1% (v/v) Tween 80, 4 mM EDTA, pH 8,0 |
| Conditioning post homogenisation buffer 2 | 0.5 M EDTA | Capture | |
| AX buffer A | 20 mM Tris, 25 mM NaCl, 0.1% Tween80, pH 7.4 | Capture | 20 mM Tris, 25 mM NaCl, 0.1% Tween80, pH 7.4 |
| AX buffer B | 20 mM Tris, 300 mM NaCl, 0.1% Tween80, pH 7.4 | Capture | 20 mM Tris, 300 mM NaCl, 0.1% Tween80, pH 7.4 |
| AX CIP1 | 2M NaCl | Capture | 2M NaCl |
| AX CIP 2 | 1M NaOH | Capture | 1M NaOH |
| AF buffer A | 20 mM Tris, 25 mM NaCl, 2 mM $CaCl_2$, 0.1% Tween80, pH 7.4 | Intermediate | 20 mM Tris, 25 mM NaCl, 2 mM $CaCl_2$, 0.1% Tween80, pH 7.4 |
| AF buffer wash | 20 mM Tris, 25 mM NaCl, 0.1% Tween80, pH 7.4 | Intermediate | 20 mM Tris, 25 mM NaCl, 0.1% Tween80, pH 7.4 |
| AF buffer B | 20 mM Tris, 10 mM EDTA, 25 mM NaCl, 0.1% Tween80, pH 7.4 | Intermediate | 20 mM Tris, 10 mM EDTA, 25 mM NaCl, 0.1% Tween80, pH 7.4 |
| AF CIP 1 | 50 mM Tris, 2M NaCl, pH 7.4 | Intermediate | 50 mM Tris, 2 M NaCl, pH 7.4 |

TABLE 4-continued

| Buffer | List of Media and solutions 3 L process | | 100 L process |
|---|---|---|---|
| | Composition | Application | Composition |
| AF CIP 2 | 0,1 M NaOH | Intermediate | 0,1 M NaOH |
| AF Storage | 25% EtOH, 1M NaCl | Intermediate | 25% EtOH, 1M NaCl |
| AX 2 conditioning | 35 mM Tris, 0.1% Tween80, 12.5 mM MgCl$_2$, pH 8.0 | Polishing | 35 mM Tris, 0.1% Tween80, 12.5 mM MgCl$_2$, pH 8.0 |
| AX buffer A | 20 mM Bis-Tris, 25mM NaCl, pH 7.4 | Polishing | 20 mM Bis-Tris, 25mM NaCl, pH 7.4 |
| AX buffer B | 20 mM Bis-Tris, 180mM NaCl, pH 7.4 | Polishing | 20 mM Bis-Tris, 180mM NaCl, pH 7.4 |
| UF/DF buffer | 20 mM Bis-Tris, 150 mM NaCl, 1 mM CaCl$_2$, pH 7.0 | Formulation | 20 mM Bis-Tris, 150 mM NaCl, 1 mM CaCl$_2$, pH 7.0 |
| Conditioning post UF/DF | 10% Tween80, 20 mM Bis-Tris, 150 mM NaCl, 1 mM CaCl$_2$, pH 7.0 | Formulation | 10% Tween80, 20 mM Bis-Tris, 150 mM NaCl, 1 mM CaCl$_2$, pH 7.0 |

A scalable fed batch fermentation process was developed and scaled-up in the production unit. The downstream purification process includes three chromatography steps. Post Benzonase treatment the filtered and diluted feed stream is applied to AX chromatography (Q Sepharose XL, GE Healthcare) as the first capture step. The eluate is conditioned by dilution to allow an intermediate purification by means of affinity chromatography (Heparin Hyper D M, Pall). The AF pool is diluted and applied to a final AX chromatography step (Source15 Q, GE Healthcare). Finally a concentration and buffer change is conducted by UF/DF.

A successful pilot run was carried out at DSP equivalent to 3 L fermentation volume to demonstrate adequate process performance for all process steps.

Target ranges were defined by the small scale process, and are used to evaluate the result of the scale up.

Comparison of Process

In the following sections the lab scale downstream process (DSP) is described in detail based on a pilot run performed at process scale equivalent to 3 L fermentation volume. Generally, besides the loading to the first capture, the chromatographic steps are performed at lab scale with an Aekta Explorer system. In large scale all chromatographic steps are conducted with a Bioprocess system. The up scaling factor for the DSP is 33 (from 3 $L_{USP}$ to 100 $L_{USP}$).

1.1.1 Resuspension of Biomass, Benzonase Treatment and Cell Disruption

Post fermentation the biomass is harvested by centrifugation and stored at −20° C. Downstream processing starts with the thawing of the biomass and the resuspension in homogenisation buffer 1. Prior homogenization Benzonase, pre-diluted in homogenisation buffer (3.300 U/L$_{USP}$ or 1.850 U/L$_{resuspended\ biomass}$), is added to the resuspended cells. The resuspension ratio is set to 1 g biomass/10 mL. Homogenization is performed in three cycles with 600 bar to reach a high degree of homogeneity which is beneficial for the following capture step. No active cooling is needed within homogenization as an elevated temperature of up to 40° C. is desired to allow an optimal digestion of nucleic acids with Benzonase. In small scale temperatures ranging from 36-40° C. were obtained.

A process flow chart for resuspension of biomass, Benzonase treatment and cell disruption is shown below:

| Process Step | Parameter | 3 L process | 100 L process |
|---|---|---|---|
| Resuspension for homogenisation | Buffer: | 50 mM Tris; pH 7.4, 1 mM MgCl2; 1% Tween80 | 50 mM Tris; pH 7.4, 1 mM MgCl2; 1% Tween80 |
| | Buffer temperature: | RT | RT |
| Addition of Benzonase | Ratio: | 1 g/10 mL | 1 g/8-10 mL |
| | Benzonase (stock 25 U/μL): | 1.850 U/L$_{res\ biomass}$ | 3.300 U/L$_{USP}$ |
| | Pre-dilution in homogenisation buffer: | In 1/10 of the final resuspension volume | In 1 L resuspension buffer |
| High pressure homogenization | Pressure: | 600 bar | 600 bar |
| | Cycles: | 3 | 3 |
| Storage of homogenate | Conditions: | Ambient temperature | Ambient temperature |

1.1.2 Clarification, Conditioning and Capture Chromatography

Subsequent to homogenization the lysate is clarified by filtration using a Cuno 60 SP (0.6-0.2 μm) depth filter. This step is conducted to reduce the content of nucleic acids additionally and to obtain a particle reduced solution which can be applied to capture chromatography. The depth filter is pre-washed with water according to the manufacturer's instructions.

Post filtration the lysate is diluted 2-fold with 1% Tween80. EDTA is added to a final concentration of 2 mM.

This conditioned pool is applied offline, with a peristaltic pump, to AX capture chromatography. The AX capture column is equilibrated with two column volumes (CV) (20 mM Tris pH 7.4, 0.1% Tween80, 25 mM NaCl) at a linear pump rate of 200 cm/h.

Post loading the column is washed offline with equilibration buffer for 5 CV and subsequently transferred to the chromatography system to do additional 5 CV of washing. The Annexin A5 elution is conducted with a step elution for 9 CV using a higher salt concentration (20 mM Tris pH 7.4; 0.1% Tween80; 300 mM NaCl). Fractionation is defined from the raising of the UV$_{280\ nm}$ signal by 0.1 absorption unit (AU) to 0.2 AU in the descending peak. The whole elution peak is further processed.

A two-step CIP procedure is carried out to regenerate and clean the column (Step 1: 2 M NaCl for 3 CV 100 cm/h; upflow/Step 2: 1 M NaOH, 3 CV; incubation for >15 h, 40 cm/h upflow). The column is finally stored in 20 mM of NaOH.

FIG. 3 provides a process flow chart for AX capture chromatography.

Generally the capture step can be considered as a conditioning step to enhance the performance of the intermediate step. It concentrates the product and significantly changes the matrix of the load. Moreover a strong reduction of endotoxin (by about 97%) and a moderate reduction of DNA and HCP was observed.

1.1.3 Intermediate—Affinity Chromatography

The obtained AX elution pool (250 mL/$L_{USP}$) is filtered (Sartopore2 0.45-0.2 µm) prior intermediate chromatography.

The filtered AX pool is subsequently 8-fold diluted (dilution buffer: 20 mM Tris pH 7.4; 0.1% Tween80; 2 mM $CaCl_2$)). The dilution with calcium allows Annexin A5 to bind to the immobilized Heparin chromatography. This interaction is, by comparison with an ionic interaction, slow. The contact time is critical and therefore the chromatography is performed with 100 cm/h.

Two washing steps are conducted. Washing step 1 is conducted for 15 CV (20 mM Tris pH 7.4; 0.1% Tween80; 2 mM $CaCl_2$)) and is followed by a second washing step for 2 CV with buffer not containing calcium (20 mM Tris pH 7.4; 0.1% Tween80).

The elution is performed with a step elution using a buffer containing EDTA (20 mM Tris pH 7.4; 0.1% Tween80; 10 mM EDTA; 25 mM NaCl) which chelates the calcium ions. The chelating reaction specifically elutes Annexin A5 which can only bind to Heparin in the presence of calcium. To allow a concentrated elution the flow rate was reduced to 60 cm/h in the elution. The complete elution peak is collecting starting from the rising of the UV signal at 0.05 AU to 0.05 AU in the descending peak representing approximately 7 CV. The elution profile demonstrates a single sharp peak.

A two-step CIP procedure is carried out to regenerate and clean the column (Step 1: 2 M NaCl for 3 CV 100 cm/h; upflow/Step 2: 0.1 M NaOH, 3 CV; incubation for >15 h, 40 cm/h upflow). The column is finally stored in 1 M NaCl in 25% EtOH.

FIG. 1 shows the process flow chart for Intermediate Affinity Chromatography.

The intermediate step is the most powerful purification step in the process scheme. Annexin A5 binds to calcium ions. In this calcium bound state the product can form a highly specific bond with Heparin. Only correctly folded Annexin A5 forms that have the ability to complex with calcium can bind to Heparin. Thereby the chromatographic step can discriminate between correctly folded and misfolded product. Additionally the intermediate step reaches high depletion factors as the highly specific interaction is combined with a specific elution mode by the chelate reaction of calcium with EDTA. Therefore a strong reduction of endotoxin (a further approximately 99% reduction) and HCP is observed combined with a moderate reduction of the DNA content.

The combined endotoxin reducing effect of the first AX capture step (about 97%) and the intermediate affinity chromatography step (about 99%) provides an Annexin A5 product in which endotoxin levels are reduced to about 0.03% of the levels in the clarified product prior to the first AX step.

1.1.4 Polishing—AX Chromatography

The obtained AF elution pool (300 mL/$L_{USP}$) is 2-fold diluted (35 mM Tris pH 8; 0.1% Tween80; 12.5 mM $MgCl_2$) and filtered (Sartopore2 0.45-0.2 µm) prior polishing chromatography. The dilution reduces the conductivity of the AX load but also complexes free EDTA molecules with Mg-ions. Otherwise the free EDTA is bound to the column thereby reducing mainly capacity but also the separation in this step.

The polishing resin is Source15 Q with an average resin diameter of 15 µm. It is a high resolution polishing resin having the disadvantage of a high back pressure. Therefore the chromatography is performed with 100 cm/h. The loading should be <16 g/L resin to allow an appropriate resolution.

Washing after loading is conducted with buffer A (20 mM Bis-Tris pH 7; 25 mM NaCl) for 3 CV. The elution is performed using a linear gradient to 100% B (20 mM Bis-Tris pH 7; 180 mM NaCl) in 33 CV. This chromatographic step is mainly designed for the removal of product related impurities. Different forms of Annexin A5 elute from 40-100% B starting with a main peak, a second reduced peak and several smaller peak which follow.

The first major peak starting at 0.05 AU to the valley between peak 1 and peak 2 representing approximately 7 CV is collected.

A two-step CIP procedure is carried out to regenerate and clean the column (Step 1: 2 M NaCl for 3 CV 100 cm/h; up-flow/Step 2: 1 M NaOH, 3 CV; incubation for >15 h, 40 cm/h up-flow). The column was finally stored in 25 mM NaCl.

Recent results obtained in small scale experiments indicated positive effects of Tween80. A process conducted with 0.1% Tween80 increased the product yield post intermediate by approximately 30%. The loading on the polishing step is limited to 16 g/L resin to ensure an appropriate resolution. The improvement in yield has also an impact on the upscaling scenario. The calculated column dimension in the polishing step was planned with two cycles. The increased yield makes a 4-5 cycle scenario necessary, if total amount from 100 $L_{USP}$ scale is processed.

FIG. 2 shows the process flow chart for the AX Polishing Chromatography step.

The polishing step is mainly implemented for the reduction of product related impurities e. g. the separation of different Annexin A5 isoforms. Additionally the polishing step reaches the highest depletion factor in the process for the residual DNA and strongly reduces HCP. Endotoxin, being already at a low level after the intermediate step, is further reduced by about 99%, which takes the endotoxin levels to about 0.0003% of the levels in the clarified product prior to the first AX step.

1.1.5 Ultra/Diafiltration and Formulation of Annexin A5

The AX pool is directly transferred to the UF/DF to elevate product concentration and perform a buffer change. Following buffer change Tween80 is added to a final concentration of 0.05% and the drug substance is sterile filtered.

In a first process step the AX pool is 6-8 fold concentrated. Following this a buffer change is conducted with 8-10 diafiltration volumes in formulation buffer not containing Tween (20 mM Bis-Tris, 150 mM NaCl, 1 mM $CaCl_2$) pH 7 or pH 7.4). Post buffer change a second concentration is conducted to achieve a final concentration of 12 g/L. This allows an addition of the first wash of the cassette and the addition of Tween80 to a final concentration of 0.05% to reach a final concentration post sterile filtration of 10 g/L. The UF/DF step is conducted with a low TMP of 0.9-1.1 bar to minimize cover layer formation.

FIG. 3 shows the process flow chart for ultra/diafiltration and formulation of Annexin A5.

2 Target Values and Acceptance Criteria

The following target values and acceptance criteria are defined to evaluate the process performance and scale-up in comparison to small scale DSP runs. Target values are defined based on IPC/Bulk analysis of a pilot run. Key process parameters were characterized to specify key process steps and enhance reliability of process performance.

2.1 Main Process Parameters

Table 5 shows the main process parameters. Attainment of target ranges during the process performance is indicative of successful process scale up.

TABLE 5

Process parameters of process steps and respective target values

| Step | Parameter | Target range |
|---|---|---|
| Homogenization | Temperature post homogenization | 34-40° C. |
|  | pressure | 600 bar |
|  | cycles | 3 |
|  | Resuspension ratio | 1 g/10 mL |
| Capture Step | load amount [g/L $_{Resin}$] | 30-50 |
| AX chromatography | [10 L$_{USP}$/L $_{Resin}$] | 10 - 12 |
| (Q Sepharose XL) | Elution criteria | Main peak |
|  | Elution criteria [UV280, 2mm] | Pool (0.1 AU-0.2 AU) |
|  | Elution volume [CV] | 5-10 |
| Intermediate Step | load amount [g/L Resin] | 20-30 |
| AF Chromatography | Elution criteria [UV280, 2mm] | Complete peak |
| (Heparin HyperD) |  | Pool (0.1 AU-0.1 AU) |
|  | Elution volume [CV] | 2-3 |
| Polishing Step | load amount [g/L Resin] | 10-23 |
| AX Chromatography | Elution criteria [UV280, 2mm] | major peak |
| (Source15 Q) |  | starting at |
|  |  | 0.05 AU to |
|  |  | the valley |
|  |  | between |
|  |  | peak 1 |
|  |  | and peak 2 |
|  | Elution volume [CV] | 5-10 |
| UF/DF-Hydrosart | Inlet Pressure [bar] | 0.8-1.2 |
| 10 KDa |  |  |

2.2 Key Process Parameters

A high degree of homogeneity of the suspension prior capture chromatography is important. The use of three homogenisation cycles is suitable to achieve this. Moreover a temperature increase within homogenization is suitable to obtain temperatures of the lysate in the range of 37° C. This is important for the activity of the Benzonase having an direct impact on the filtration step and capture performance.

The pooling from the polishing step is also important as this step is used for the separation of product related impurities. The UF/DF step is performed under moderate conditions with regard to TMP to minimize the formation of a cover layer.

TABLE 6

Important process parameters

| Step | Parameter | Target range |
|---|---|---|
| homogenization | Temperature post homogenization | 34-40° C. |
| homogenization | Cycle times | 3 |
| Polishing | Loading | 10-16 g/L Resin |
| Pooling after polishing | UV signal (2mm) | major peak starting at 0.05 AU to the valley between peak 1 and peak 2 |
| UF/DF | TMP | 0.9-1.1 bar |

2.3 In-Process Controls

Table 7 shows the In-Process Controls. Target ranges achieved during the process performance show successful process scale up. Target ranges were set based on observations in previous small scale runs, which were performed with implemented changes, only.

| Step Nomenclature: | | | | |
|---|---|---|---|---|
| 3 L process | 100 L process | Test | Laboratory | Target range |
| Resuspension for homogenisation IPC-D01 | Resuspension for homogenisation IPC-03.1 | Content: SDS-PAGE [g/L] SDS-PAGE (soluble & insoluble fraction on red. Gel) [ratio in sol/insol in %] | Bioanalytics HH Bioanalytics HH | >5 g/L USP <40% insoluble |
| Cell disruption (post cycle 3) IPC-D05 | Cell disruption (post cycle 3) IPC-03 | Content: SDS-PAGE [g/L] SDS-PAGE (soluble & insoluble fraction on red. Gel) [ratio in sol/insol in %] | Bioanalytics HH Bioanalytics HH | >5 g/L USP <40% insoluble |
| Clarification IPC-D07 | Clarification IPC-04 | Content: SDS PAGE [g/L] | Bioanalytics HH | n.a. |
| Conditioning for Capture | Online Dilution for Capture | Content: SDS PAGE [g/L] | Bioanalytics HH | t.b.d. |

-continued

| Step Nomenclature: | | | | |
|---|---|---|---|---|
| 3 L process | 100 L process | Test | Laboratory | Target range |
| IPC-D07a | IPC-05.1 | Identity: SDS-PAGE Coomassie | Bioanalytics HH | t.b.d. |
| | | Purity: HCP (WB) | Bioanalytics HH | band pattern |
| | | Purity: HCP (ELISA) [ng/mg] | Bioanalytics HH | t.b.d. |
| | | Purity: DNA (qPCR) [pg/mg] | Bioanalytics HH | t.b.d. |
| | | Purity: Endotoxin [EU/mg]; [EU/mL] | L + S | t.b.d. |
| AX capture FT IPC-D08 | AX capture FT IPC-05.2 | Identity: SDS-PAGE Coomassie | Bioanalytics HH | band pattern |
| AX capture elution pool IPC-D09 | AX capture elution pool IPC-05 | Content: AX-HPLC [g/L] | PANATecs | n.a. |
| | | Content: SDS PAGE [g/L] | Bioanalytics HH | t.b.d. |
| | | Identity: SDS-PAGE Coomassie | Bioanalytics HH | band pattern |
| | | Identity: IEF | Bioanalytics HH | band pattern |
| | | Purity: HCP (WB) | Bioanalytics HH | band pattern |
| | | Purity: HCP (ELISA) [ng/mg] | Bioanalytics HH | t.b.d. |
| | | Purity: DNA (qPCR) [pg/mg] | Bioanalytics HH | Reduced compared to IPC-D07a |
| | | Purity: Endotoxin [EU/mg]; [EU/mL] | L + S | Reduced compared to IPC-D07a |
| | | Purity: AX-H PLC [%] | PANATecs | t.b.d. |
| AX capture Salt CIP IPC-D10 | AX capture Salt CIP IPC-05.3 | Optional analytics | Bioanalytics HH | n. a. |
| 0.2 μm filtration of capture pool IPC-D11 | of 0.2 μm filtration of capture pool IPC-06.1 | n.a. | Bioanalytics HH | n.a. |
| Conditioning for AF Intermediate IPC-D12 | Conditioning for AF Intermediate IPC-06.2 | Content: AX-HPLC [g/L] | PANATecs | n.a. |
| AF intermediate FT + wash IPC-D13 | AF intermediate FT IPC-06.3 | Content: AX-HPLC [g/L] | PANATecs | n.a. |
| | | Identity: SDS-PAGE Coomassie | Bioanalytics HH | band pattern |
| AF intermediate Elution pool IPC-D14 | AF intermediate Elution pool IPC-06 | Content: AX-HPLC [g/L] | PANATecs | n.a. |
| | | Content: UV280 [g/L] | QC H | t.b.d. |
| | | Identity: SDS-PAGE Coomassie | Bioanalytics HH | band pattern |
| | | Identity: IEF | Bioanalytics HH | band pattern |
| | | Purity: HCP (WB) | Bioanalytics HH | band pattern |
| | | Purity: HCP (ELISA) [ng/mg] | Bioanalytics HH | Reduced compared to IPC-D09 |
| | | Purity: DNA (qPCR) [pg/mg] | Bioanalytics HH | Reduced compared to IPC-D09 |
| | | Purity: Endotoxin [EU/mg]; [EU/mL] | L + S | Reduced compared to IPC-D09 |
| | | Purity: | PANATecs | t.b.d. |

-continued

| Step Nomenclature: | | | | |
|---|---|---|---|---|
| 3 L process | 100 L process | Test | Laboratory | Target range |
| | | Purity: AX-H PLC [%] | QC BV | t.b.d. |
| | | Purity: SEC [%] | | |
| 0.2 μm filtration of intermediate pool IPC-D17 | 0.2 μm filtration of intermediate pool IPC-07.1 | Optional analytics | Bioanalytics HH | n.a. |
| AX polishing FT + wash IPC-D18 | AX polishing FT IPC-07.2 | Identity: SDS-PAGE Coomassie FQKA-HB005 | Bioanalytics HH | band pattern |
| AX polishing Salt CIP IPC-D20 | AX polishing Salt CIP IPC-07.3 | Optional analytics | Bioanalytics HH | n. a. |
| — | AX polishing fraction IPC-07.4 | Identity: IEF | Bioanalytics HH | band pattern |
| | | Purity: AX-H PLC [%] | PANATecs | t.b.d. |
| — | AX polishing fraction IPC-07.5 | Identity: IEF | Bioanalytics HH | band pattern |
| | | Purity: AX-H PLC [%] | PANATecs | t.b.d. |
| — | AX polishing fraction IPC-07.6 | Identity: IEF | Bioanalytics HH | band pattern |
| | | Purity: AX-H PLC [%] | PANATecs | t.b.d. |
| — | AX polishing fraction IPC-07.7 | Identity: IEF | Bioanalytics HH | band pattern |
| | | Purity: AX-H PLC [%] | PANATecs | t.b.d. |
| AX polishing Elution Pool IPC-D19 | AX polishing Elution Pool IPC-07 | Content: AX-HPLC [g/L] | PANATecs | t.b.d. |
| | | Content: UV280 [g/L] | Q CH | t.b.d. |
| | | Identity: SDS-PAGE Coomassie | Bioanalytics HH | band pattern |
| | | Identity: IEF | Bioanalytics HH | band pattern |
| | | Purity: HCP (WB) | Bioanalytics HH | band pattern |
| | | Purity: HCP (ELISA) [ng/mg] | Bioanalytics HH | Reduced compared to IPC-D14 |
| | | Purity: DNA (qPCR) [pg/mg] | Bioanalytics HH | Reduced compared to IPC-D14 |
| | | Purity: Endotoxin [EU/mg]; [EU/mL] | L + S | Reduced compared to IPC-D14 |
| | | Purity: AX-HPLC [%] | PANATecs | t.b.d. |
| | | Purity: SEC [%] | QC BV | t.b.d. |
| Post concentration IPC-D21 | Post concentration IPC-08.1 | Optional analytics | Bioanalytics HH | n. a. |
| Post diafiltration/conc. IPC-D22 | Post diafiltration/conc. IPC-08.2 | Content: UV280 [g/L] | Q CH | t.b.d. |
| Post addition of cassette wash andaddition of Tween80 IPC-D23 | Post addition of cassette wash IPC-08.3 | Content: UV280 [g/L] | Q CH | t.b.d. |
| Bulk including Tween80 IPC-D24 | Bulk including Tween80 IPC-08 | Content: UV280 [g/L] | Q CH | >10 g/L |
| Bulk Sterile filtered IPC-D25 | Bulk Sterile filtered IPC-09 | Identity: SDS PAGE red. | Bioanalytics HH | Confirms to reference |
| | | Identity: IEF | Bioanalytics HH | Main band corresponds to reference |

-continued

Step Nomenclature:

| 3 L process | 100 L process | Test | Laboratory | Target range |
|---|---|---|---|---|
| | | Content: UV280 [g/L] | Q CH | 8-12 g/L |
| | | Purity: HCP (WB) | Bioanalytics HH | band pattern |
| | | Purity: HCP (ELISA) [ng/mg] | Bioanalytics HH | 100 ng/mg |
| | | Purity: DNA (qPCR) [pg/mg] | Bioanalytics HH | 100 pg/mg |
| | | Purity: Endotoxin | L + S | 35 EU/mg |
| | | Purity: AX-HPLC [%] | PANATecs | t.b.d. |
| | | Purity: SEC [%] | QC BV | >95 |
| | | Bioburden Ph. Eur. 2.6.12 | L + S | <1 cfu/mL |
| | | Potency | Bioassay HH | t.b.d. |
| | | pH | QC-Hannover | 6.8-7.2 |
| | | Appearance | QC-Hannover | Clear, colourless, free of visible particles |
| | | Purity: SDS PAGE non-red. Silver | QC BV | >90 % |
| | | Content: AX-HPLC [g/L] | PANATecs | t.b.d. |
| | | Identity: Western Blot | Bioanalytics HH | Main band corresponds to reference |
| | | Osmolality | TECHPharm | t.b.d. |

Conclusions

The foregoing manufacturing process is well adapted for large scale manufacturing with no bottlenecks for up-scale to and above 10,000 L scale, if needed.

Following a pilot run using a scaled-up 200 L in a GMP pilot plant, the process delivered a product having 1.8 pg host cell DNA per mg of AnxA5 protein; 16.6 ng host cell protein per mg of AnxA5 protein; and 0.1 EU per mg of AnxA5 protein.

Throughout the manufacturing process, the Annexin A5 protein is kept in solution in its active form when not temporarily bound to chromatography resins.

As applied to a 1,000 L culture, the overall process time in the manufacturing plant will be one week in fermentation, harvest, cell-disruption and processing prior chromatography and an consecutive week in downstream processing. The whole process in a GMP plant will be 2 weeks. This is independent of scale and perfectly adapted to industry standard and would fit into any CMO or pharmaceutical manufacturer.

As noted above, in comparison, the process of Marder et al. would take around 12 weeks to process a 1,000 L culture.

Moreover, the yield in the present process is 2-3 times higher per batch than that of Marder et al. This makes the manufacturing cost per gram Annexin A5 drug substance between (6-8×2-3=) 12-24 times higher for the Marder process.

Furthermore, in addition to providing a purification process that is faster, and with higher yield than the process of Marder et al., the process of the present invention also provides a higher purity product. As discussed above in Comparative Example 1, the purity of the protein from the Marder process would not be suitable for human use. Despite elaborate centrifugations, only one anion exchange chromatography step is used in the Marder process which is far below the requirements to reach sufficient purity with regards to both in-process related impurities (especially endotoxin) and product related variants. Marder does not show any data on endotoxin levels or other impurities further indicating lack of suitability for pharmaceutical use.

In contrast, the process of the present application provides a highly pure Annexin A5 protein product, having the characteristics listed as follows:

a concentration typically around 8-12 g/L;
host cell protein levels at or below 100 ng/mg, more typically below 20 ng/mg (as determined by ELISA);
host cell DNA levels at or below 100 pg/mg, more typically below 10 pg/mg;
Endotoxin at or below 35 EU/mg, more typically below 1 EU/mg,
a purity of >95% as determined by size-exclusion chromatography;
a bioburden of <1 cfu/mL (as determined by Ph. Eur. 2.6.12);
a clear, colourless appearance free of visible particles; and wherein the main band detected by western blot analysis corresponds to the Annexin A5 reference.

The process was repeated using Capto Q ImpRes for the second polishing step in place of Source 15 Q. This provided an even more efficient process, as the Capto Q ImpRes anion exchange resin has a high binding capacity, tolerates high flowrates with low back pressure, can be packed at a higher bed height and has a lower price. The quality and purity of the final product was maintained.

Compared to Source 15 Q, the Capto Q ImpRes resin has:
More than double capacity in terms of gram/litre resin
Tolerates more than 2× higher flowrate at the same backpressure
Can be packed at higher bed heights, typically about 35-60% higher, which provides a higher capacity for any given column footprint; and
Cost less than half of the price at purchase per litre of resin.

Example 2

The example illustrated a comparison of anion exchange (AX) capture and affinity capture by heparin chromatography.
AX capture and heparin affinity capture chromatography were compared with respect to Annexin A5 step yield and purity in the capture eluate. Both strategies were compared in batch experiments under optimized conditions.
Test Parameters:
Ax Chromatography:
Batch mode 500 µl resin (75% slurry)
Buffer AX A: 20 mM NaPhosphate pH 7, 5 mM EDTA, 250 mM NaCl
Buffer AX B: 20 mM NaPhosphate pH 6.5, 5 mM EDTA
AX chromatography: Load: 10 mL pre-filtered lysate
CIP: 1 M NaOH
Heparin Affinity Chromatography:
Batch mode 500 µl resin (75% slurry)
Load: 10 mL pre-filtered lysate; +10 mM CaCl$_2$)
Buffer AF A: 50 mM Tris pH 7.4, 5 mM CaCl$_2$)
Buffer AF B: 50 mM Tris pH 7.4, 40 mM EGTA, 50 mM NaCl
CIP: 3 M NaCl

TABLE 7

Comparison of AX and Heparin affinity chromatography capture

|  | Resin | Recovery (%) | Purity (determined based on SDS-PAGE-R&D) (%) |
|---|---|---|---|
| AX | Q Sepharose XL | 70-90 | 10-20 |
| Affinity | Heparin Hyper D | 30-40 | 85-95 |
| Affinity (after AX) | Heparin Hyper D (Q Sepharose XL) | 70-80 | 85-95 |

These results demonstrate that performing an AX capture before the affinity chromatography does not significantly improve the purity but has a considerable influence on the Heparin step yield. Moreover the costly affinity resin might have a prolonged lifetime if used as an intermediate step. Yield is of major importance.
The capture by AX might be rated as a conditioning step which allows an effective use of the highly specific affinity step by Heparin chromatography.

Example 3

A partially purified Annexin A5 product was obtained using methods similar to Example 1, up to the first Anion exchange chromatography capture step.
Briefly, recombinant *E. coli* expressing Annexin A5 were resuspended in a homogenisation buffer (50 mM Tris, 1 mM MgCl, 1% Tween20 pH 7.5), with 3200 U of Bezonase and homogenised with three cycles of 600 bar pressure. Temperature post homogenisation was measured with 36° C. A clarifying step using Cuno 60 SP 0.6-0.2 µm was performed, and the clarified solution diluted 1:2 in 1% Tween20, with the addition of EDTA. Post conditioning for capture the solution had a pH 6.9 and a conductivity of 2.7 mS/cm. Anion exchange was performed sing Q Sepharose XL (GE), washed with Buffer A (20 mM Tris, 25 mM NaCl, 0.1% Tween20, pH 7.4), and then eluted with Buffer B (20 mM Tris, 300 mM NaCl, 0.1% Tween20, pH 7.4). The resultant product was then sterile filtered with a 0.2 µm filter.
The resultant sterile filtered anion exchange product was the purified using heparin affinity chromatography and different conditions tested.
The heparin affinity chromatography conditions used were as follows:

| Heparin HyperD M | 50 mL CV |
|---|---|
| Volume of diluted load (mL) | 1173 |
| Volume after load (mL) | 5 |
| Volume of flow through (mL) | 1145 |
| Volume of mock elution pool (A5-B6) 50 up to 50 mAU in the descending peak) (mL)-UV 2 mm- | 150 |
| Volume of IPC samples (mL) | — |
| Flow rate (cm/h) | 100 (elution 60) |

Figure 7A:
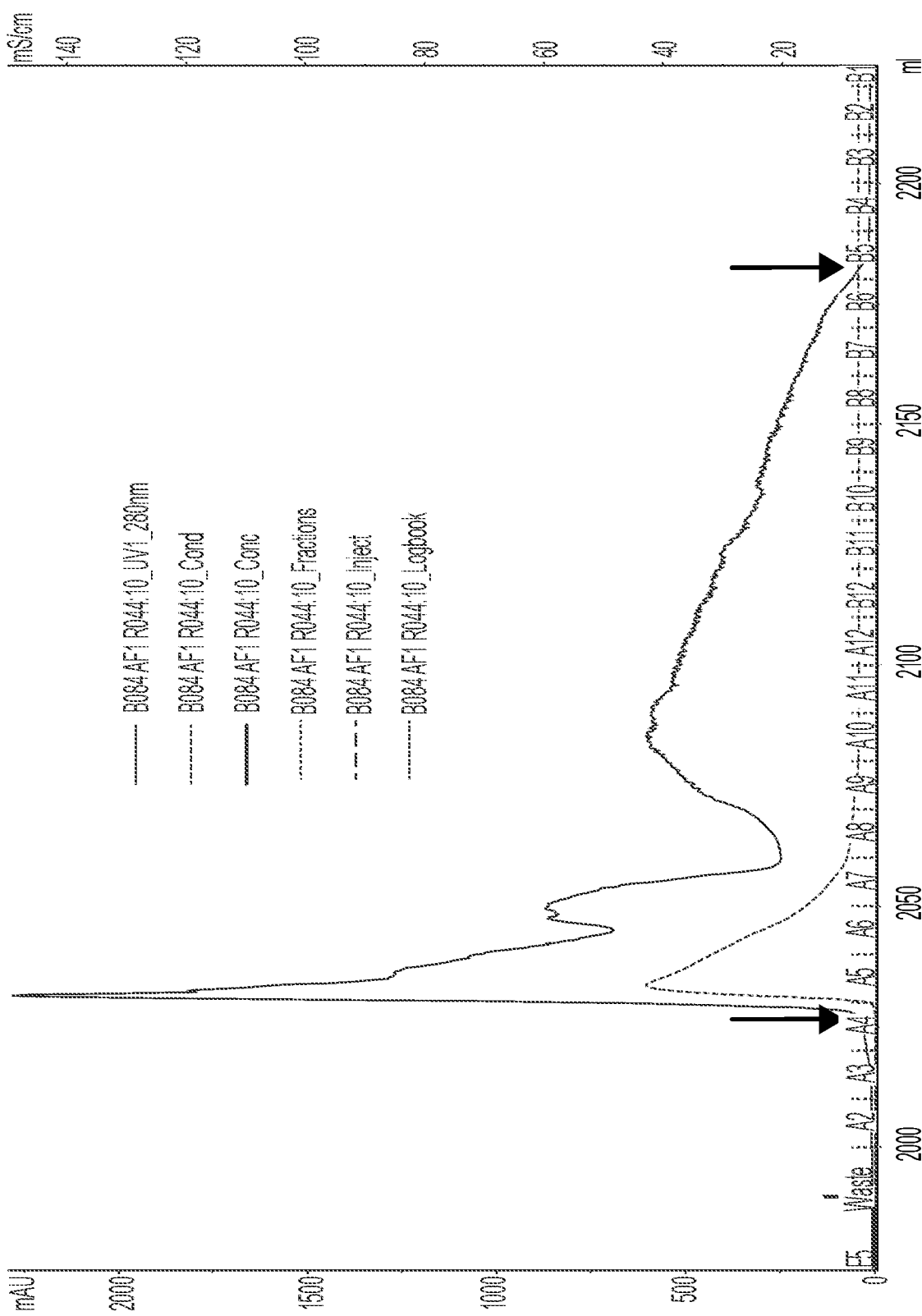
Figure 7B:
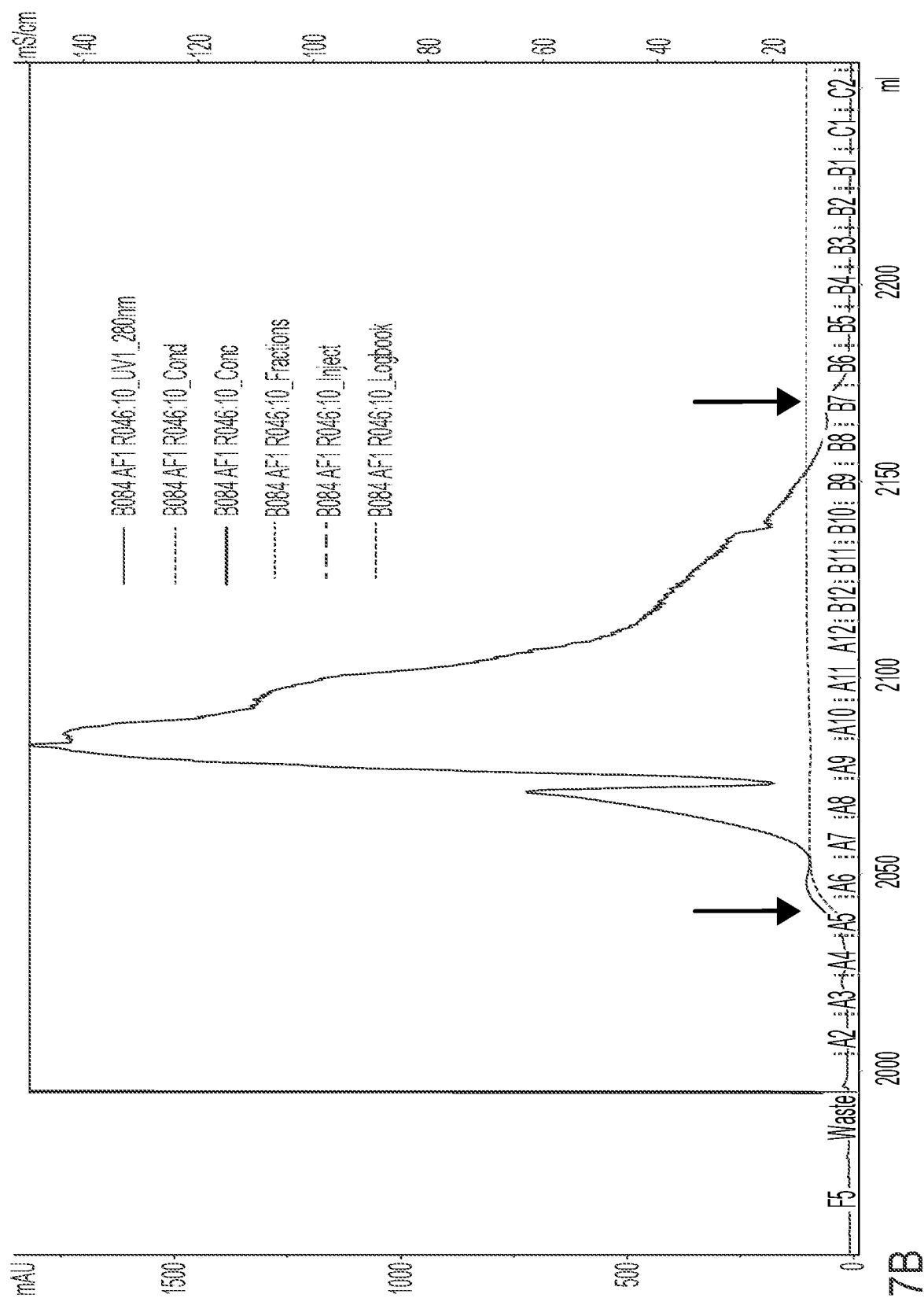

Sterile filtration of capture elution pool was performed with Sartopore 2 0.45-0.2 µm. This pool was 8 fold diluted with (1050 mL) buffer A from Heparin chromatography. The resulting pool had a pH of 7.4 and a conductivity of 6.8 mS. Elution was conducted using a reduced flow rate of 60 cm/h.
Tests 1 and 2 were performed to determine the impact of Tween80 using Buffer A for wash and Buffer B for elution, as follows:
Test 1:
Buffer A 20 mM Tris, 25 mM NaCl, 2 mM CaCl$_2$), 0.1% Tween20, pH 7.4
Buffer B 20 mM Tris, 10 mM EDTA, 25 mM NaCl, 0.1% Tween20, pH 7.4
Test 2:
Buffer A 20 mM Tris, 25 mM NaCl, 2 mM CaCl$_2$), 0.1% Tween20, 0.1% Tween80 pH 7.4
Buffer B 20 mM Tris, 10 mM EDTA, 100 mM NaCl, 0.1% Tween20, 0.1% Tween80 pH 7.4
The results for Test 1 are shown in FIG. 7A, and the results for Test 2 are shown in FIG. 7B.
The results show that the addition of Tween80 shifted the elution to a single peak, in contrast to the separated elution under standard conditions (Test 1). Tween80 appears to stabilize Annexin A5. A possible explanation for the change in the elution behavior is that a theoretical precipitation on the column is prevented. Two major positive effects can be described for the use of Tween80 in the heparin affinity chromatography step:
Reduced pressure: The pressure on the column, which increased in the loading from 0.5 to 2-3 bar, was clearly reduced to 0.5 bar. This is especially beneficial for the large scale. The slight precipitation that is seen after prolonged incubation might be the reason for the pressure increase.
Prevention of precipitation: The second positive effect is seen in the elution. Within fractionation of the elution the highly concentrated main peak fractions have a tendency to precipitate. After pooling of the fractions no precipitation is observed anymore assuming that this effect has to do with the very high concentration of Annexin A5 in the main peak: Moreover the precipitation seems to be reversible. The precipitation in the main peak could not be prevented by elevated salt concentration in the elution. In contrast to this the addition of Tween80 did also prevent the formation of precipitates in the main peak fractions.

Based on these results it seems advantageous to additionally add Tween80 in all intermediate chromatography buffers as it has a stabilizing effect on Annexin A5.

Example 4

A partially purified Annexin A5 product was obtained using methods similar to Example 1, up to the first Anion exchange chromatography capture step.

1.25 mL of the product of the anion exchange step was then mixed with 8.75 mL of different forms of test dilution buffer. The mixtures were then incubated at ambient temperature and visually evaluated after 30 mins, 18 hours, and 4 days.

The results are shown in the table below:

| approach | Dilution buffer | Time point 1 (30 min) | Time point 2 (18 h) | Time point 3 (4 days) |
| --- | --- | --- | --- | --- |
| A | 20 mM Tris, 25 mM NaCl, 2 mM CaCl2, 0.1% Tween 20 pH 7.4 | Clear opalescence barely detectable | Opalescent First signs of precipitation | Opalescent and partly precipitated |
| B | 20 mM Tris, 50 mM NaCl, 2 mM CaCl2, 0.1% Tween 20 pH 7.4 | Clear opalescence barely detectable | Opalescent First signs of precipitation | Opalescent and partly precipitated |
| C | 200 mM Glycin, 20 mM Tris, 25 mM NaCl, 2 mM CaCl$_2$, 0.1% Tween 20, pH 7.4 | Clear opalescence barely detectable | Opalescent First signs of precipitation | Opalescent and partly precipitated |
| D | 200 mM Arginin, 20 mM Tris, 25 mM NaCl, 2 mM CaCl$_2$, 0.1% Tween 20, pH 7.4 | Clear opalescence barely detectable | Opalescent First signs of precipitation | Opalescent and partly precipitated |
| E | 20 mM Tris, 25 mM NaCl, 2 mM CaCl$_2$, 0.1% Tween 20, 0.1% Tween 80, pH 7.4 | Clear opalescence barely detectable | Opalescent No signs of precipitation | Opalescent No signs of precipitation |
| F | 20 mM Tris, 25 mM NaCl, 2 mM CaCl$_2$, 0.1% Tween 20 pH 8.0 | Clear opalescence barely detectable | Opalescent First signs of precipitation | Opalescent and partly precipitated |

These results showed the benefit of adding Tween 80 (i.e. polysorbate 80) in avoiding product precipitation in a sample. This is important in the context of conditioning an AnxA5 product prior to application to a chromatographic column, such as an affinity chromatography column, in order to reduce precipitation and prevent increases in back pressure when running the column.

The invention claimed is:

1. A process for the recovery and/or purification of a recombinantly expressed intracellular protein comprising the sequence of Annexin A5 (AnxA5) from an endotoxin-producing host cell with a cell wall, wherein the process comprises releasing the intracellular protein from the host cell,
   characterised in that the step of releasing the intracellular AnxA5 protein is conducted in the presence of a homogenisation buffer comprising non-ionic detergent, and
   wherein the endotoxin-producing host cell is cultured in a volume of at least 100 L.

2. The process of claim 1, wherein the process is further characterised by one or more features selected from the group consisting of:
   (a) the non-ionic detergent is a polysorbate,
   (b) the non-ionic detergent is a polysorbate selected from the group consisting of polysorbate 20 and polysorbate 80,
   (c) the non-ionic detergent is polysorbate 80.

3. The process of claim 1, wherein the process is further characterised by one or more features selected from the group consisting of:
   (a) at the time of releasing the intracellular AnxA5 protein from the host cell, or after releasing the intracellular AnxA5 protein from the host cell but before any further chromatographic purification occurs, the homogenisation buffer has a free calcium ion concentration that is a concentration selected from the group consisting of: lower than 10 mM, lower than 5 mM, lower than 1 mM, lower than 500 µM, or zero;
   (b) the homogenisation buffer comprises, or is modified after releasing the intracellular AnxA5 protein to include, a calcium metal ion chelator;
   (c) the homogenisation buffer comprises, or is modified after releasing the intracellular AnxA5 protein to include, a calcium metal ion chelator selected from the group consisting of EDTA or salt thereof, or EGTA or salt thereof;
   (d) the homogenisation buffer comprises, or is modified after releasing the intracellular AnxA5 protein to include, EDTA.

4. The process of claim 1, wherein the volume is selected from the group consisting of at least 500 L, at least 1,000 L, at least 5,000 L, or at least 10,000 L.

5. The process of claim 1, further comprising the step of subjecting the released AnxA5 protein to an anion exchange resin in order to perform a first anion exchange step, and thereby produce a first anion exchange product which comprises the released AnxA5 protein.

6. The process of claim 5, wherein the AnxA5 protein is bound during the anion exchange step, and the first anion exchange product which comprises the released AnxA5 protein is produced by applying a wash solution and/or an elution buffer to the anion exchange resin to release the bound AnxA5 protein.

7. The process of claim 6, further comprising the step of subjecting the released AnxA5 protein to an affinity chromatography step, thereby to produce a first affinity chromatography product which comprises the released AnxA5 protein.

8. The process of claim 7 wherein the affinity chromatography step comprises the binding of the AnxA5 protein to immobilised heparin, and optionally wherein:
(a) the binding is promoted by the presence of calcium ions; and/or
(b) the AnxA5 protein is eluted from the immobilised heparin using an elution buffer containing a calcium ion chelator.

9. The process of claim 8, wherein the calcium ion chelator is EDTA.

10. The process of any claim 7, wherein the first affinity chromatography product is an affinity chromatography product selected from the group consisting of:
(a) a first affinity chromatography product that comprises the released AnxA5 protein and a calcium ion chelator,
(b) a first affinity chromatography product that comprises the released AnxA5 protein and EDTA;
(c) a first affinity chromatography product that comprises the released AnxA5 protein and EGTA;
(d) a first affinity chromatography product that comprises the released AnxA5 protein and EDTA in a range selected from the group consisting of 0.1 to 500 mM, or about 10 mM; and
(e) a first affinity chromatography product that comprises the released AnxA5 protein and EGTA in a range selected from the group consisting of 0.1 to 500 mM, or about 10 mM.

11. The process of claim 1, comprising steps wherein:
(a) releasing the intracellular AnxA5 protein to create a biomass homogenate comprising the released AnxA5 protein,
(b) subjecting said biomass homogenate to a step of clarifying the biomass homogenate and thereby producing a clarified product comprising the released AnxA5 protein,
(c) subjecting the AnxA5 protein in the clarified product to an anion exchange resin in order to perform a first anion exchange step, and thereby produce a first anion exchange product which comprises the AnxA5 protein, wherein the AnxA5 protein is bound during the anion exchange step, and the first anion exchange product which comprises the released AnxA5 protein is produced by applying a wash solution and/or an elution buffer to the anion exchange resin to release the bound AnxA5 protein, and
(d) subjecting the AnxA5 protein in the first anion exchange product to an affinity chromatography step, thereby to produce a first affinity chromatography product which comprises the released AnxA5 protein.

12. A process for the recovery and/or purification of a protein comprising the sequence of Annexin A5 (AnxA5), from a solution comprising the AnxA5 protein and one or more impurities, the method comprising
subjecting the solution comprising the AnxA5 protein and one or more impurities to a heparin affinity chromatography step in the presence of polysorbate 80, thereby to produce a first affinity chromatography product which comprises the released AnxA5 protein.

13. The process of claim 12, wherein polysorbate 80 is 0.1% polysorbate 80.

14. A process for the recovery and/or purification of a protein comprising the sequence of Annexin A5 (AnxA5) from a composition that comprises the AnxA5 protein and a calcium metal ion chelator selected from EDTA and/or EGTA,
characterised in that the process comprises subjecting the composition to an anion exchange resin in order to perform an anion exchange step and thereby recover and/or purify the AnxA5 protein from the composition, and
further characterised in that the anion exchange step is conducted in the presence of selected divalent metal cations,
wherein the selected divalent metal cations are selected such that the calcium metal ion chelator has a binding affinity for the selected divalent metal cations that is greater than its binding affinity for the anion exchange resin, but less than its binding affinity for calcium ions.

15. The process of claim 14, wherein the calcium metal ion chelator is present in the composition in an excess and/or at a concentration of about, or at least, 0.1 mM, 0.5 mM, 1 mM, 5 mM, 10 mM, 15 mM, 20 mM or more.

16. The process of claim 14, wherein the selected divalent metal cations are $Mg^{2+}$ ions.

17. The process of claim 14, wherein
the composition that comprises the AnxA5 protein and a calcium metal ion chelator and which is subjected to the anion exchange resin is
the direct, or indirect, product of a preceding process that comprises the step of subjecting the AnxA5 protein to an affinity chromatography step and eluting the AnxA5 protein with a calcium ion chelator, thereby producing an affinity chromatography product which is a composition that comprises the AnxA5 protein and a calcium metal ion chelator, and
optionally, wherein the preceding affinity chromatography step comprises the binding of the AnxA5 protein to immobilised heparin, and further optionally wherein the binding is promoted by the presence of calcium ions.

18. A process for the recovery and/or purification of a recombinantly expressed intracellular protein comprising the sequence of Annexin A5 (AnxA5) from an endotoxin-producing host cell with a cell wall, wherein:
(a) the process comprises releasing the intracellular protein from the endotoxin-producing host cell with a cell wall, in the presence of a homogenisation buffer comprising non-ionic detergent, wherein the endotoxin-producing host cell is cultured in volume of at least 100 L;
(b) wherein the process further comprises the step of subjecting the released AnxA5 protein directly or indirectly to an anion exchange resin, optionally in the presence of a calcium ion chelator, in order to perform a first anion exchange step, and thereby produce a first anion exchange product which comprises the released AnxA5 protein; and
(c) wherein the process further comprises the step of subjecting the released AnxA5 protein directly or indirectly to an affinity chromatography step;
(d) wherein the product of the affinity chromatography step is a composition that comprises the AnxA5 protein and a calcium metal ion chelator; and
(e) wherein the direct, or indirect, product of the affinity chromatography step that comprises the AnxA5 protein and the calcium metal ion chelator is subjected to anion exchange step.

19. The process of claim 18, wherein the process comprises, at the end of the process, one or more further steps selected from the group consisting of concentration, buffer change, conditioning and filtration, and optionally a final step of storing the AnxA5 protein-containing product in a sterile container.

20. The process of claim 19, wherein:
(a) one of the further steps is diafiltration, optionally wherein the product of the diafiltration step contains the AnxA5 protein at a concentration of at least about 1 mg/mL, 5 mg/mL, 10 mg/mL, 15 mg/mL, 20 mg/mL, 50 mg/mL, 100 mg/mL or greater; and
(b) the filtration uses a 0.45-0.2 μm filter or a 0.22 μm filter.

21. The process of claim 19, wherein the filtration is sterile filtration.

22. The process of claim 20, wherein the filtration is sterile filtration and the final purification step prior to storing the AnxA5 protein-containing product in a sterile container.

* * * * *